(12) United States Patent
Minai et al.

(10) Patent No.: US 8,050,738 B2
(45) Date of Patent: Nov. 1, 2011

(54) POSITION DETECTING APPARATUS USING THE MAGNETIC FIELD DIRECTION OF THE EARTH'S MAGNETIC FIELD

(75) Inventors: Tetsuo Minai, Tokyo (JP); Takeshi Mori, Tokyo (JP)

(73) Assignee: Olympus Corporation, Tokyo (JP)

( * ) Notice: Subject to any disclaimer, the term of this patent is extended or adjusted under 35 U.S.C. 154(b) by 1001 days.

(21) Appl. No.: 11/728,804

(22) Filed: Mar. 27, 2007

(65) Prior Publication Data

US 2007/0238987 A1     Oct. 11, 2007

Related U.S. Application Data

(63) Continuation-in-part of application No. 11/661,619, filed on Apr. 9, 2007.

(30) Foreign Application Priority Data

| Aug. 30, 2004 | (JP) | 2004-251023 |
| Sep. 8, 2004 | (JP) | 2004-261666 |
| Sep. 13, 2004 | (JP) | 2004-266067 |

(51) Int. Cl.
*A61B 5/05* (2006.01)

(52) U.S. Cl. ........ 600/424; 600/117; 600/118; 600/407; 128/899; 702/150; 702/153

(58) Field of Classification Search .................. 600/117, 600/118, 145, 407, 424; 128/899; 324/207.11, 324/207.13, 207.22–24; 702/150–153
See application file for complete search history.

(56) References Cited

U.S. PATENT DOCUMENTS

| 4,317,078 A | * | 2/1982 | Weed et al. | ............... 324/207.26 |
| 5,711,299 A | * | 1/1998 | Manwaring et al. | ........... 600/417 |
| 5,729,129 A | * | 3/1998 | Acker | ....................... 324/207.12 |
| 6,263,230 B1 | * | 7/2001 | Haynor et al. | ................. 600/424 |
| 6,618,612 B1 | * | 9/2003 | Acker et al. | .................... 600/424 |

(Continued)

FOREIGN PATENT DOCUMENTS

JP     56-035009     4/1981

(Continued)

OTHER PUBLICATIONS

U.S. Office Action issued Jul. 12, 2010, in related U.S. Appl. No. 11/661,619.

(Continued)

*Primary Examiner* — Ruth S Smith
*Assistant Examiner* — Rajeev Siripurapu
(74) *Attorney, Agent, or Firm* — Scully, Scott, Murphy & Presser, P.C.

(57) ABSTRACT

A position detecting apparatus includes a linear magnetic-field generator that generates a linear magnetic field in an area inside the subject; a diffuse magnetic-field generator that generates a diffuse magnetic field having position dependency on magnetic field direction in the area; a magnetic-field line orientation database in which a correspondence between magnetic field direction and position of the diffuse magnetic field in a reference coordinate axis is recorded; an orientation calculator that calculates orientation information of a body-insertable device introduced into a subject in the reference coordinate axis based on linear magnetic-field information and the earth magnetism direction; and a position calculator that calculates a magnetic field direction of the diffuse magnetic field at the position of the body-insertable device based on the linear magnetic-field information, orientation information, and diffuse magnetic-field information, and calculates the position of the body-insertable device based on the magnetic field direction and correspondence recorded.

5 Claims, 48 Drawing Sheets

U.S. PATENT DOCUMENTS

| | | |
|---|---|---|
| 2002/0173718 A1 | 11/2002 | Frisch et al. |
| 2002/0198439 A1 | 12/2002 | Mizuno |
| 2003/0229268 A1 | 12/2003 | Uchiyama et al. |
| 2004/0111011 A1 | 6/2004 | Uchiyama et al. |

FOREIGN PATENT DOCUMENTS

| | | |
|---|---|---|
| JP | 04-112305 | 4/1992 |
| JP | 09-047989 | 2/1997 |
| JP | 09-072192 | 3/1997 |
| JP | 2003-019111 | 1/2003 |
| JP | 2003-70728 | 3/2003 |
| JP | 2004-41709 | 2/2004 |
| JP | 2004-521662 | 7/2004 |
| JP | 2004-535878 | 12/2004 |
| JP | 2005-245941 | 9/2005 |
| WO | WO 96/41119 A | 12/1996 |
| WO | WO 01/87377 A2 | 11/2001 |
| WO | WO 03/009739 | 2/2003 |

OTHER PUBLICATIONS

U.S. Office Action issued Jul. 9, 2010, in related U.S. Appl. No. 11/728,697.

U.S. Office Action mailed Feb. 4, 2011 in related U.S. Appl. No. 11/728,697.

* cited by examiner

POSITION DETECTING APPARATUS USING THE MAGNETIC FIELD DIRECTION OF THE EARTH'S MAGNETIC FIELD

CROSS-REFERENCE TO RELATED APPLICATIONS

This is a continuation-in-part of co-pending application Ser. No. 11/661,619, filed Apr. 9, 2007.

BACKGROUND OF THE INVENTION

1. Field of the Invention

The present invention relates to a position detecting apparatus that uses a position detecting magnetic field having position dependency regarding strength to detect a position of a detected object, at least at a first time instant and a second time instant when a predetermined time has passed since the first time instant, and a body-insertable apparatus system.

2. Description of the Related Art

Recently, in the field of endoscope, a swallowable capsule endoscope has been proposed. The capsule endoscope is provided with an imaging function and a radio communication function. This capsule endoscope has a function of moving in a body cavity, for example, internal organs such as a stomach and a small intestine with peristalsis thereof, during a period after it is swallowed from a mouth of the subject for observation (examination) until it is naturally discharged from the subject, and of sequentially imaging intra-subject images.

While the endoscope is moving in the body cavity, image data imaged in the body by the capsule endoscope is sequentially transmitted to the outside by radio communications, and stored in a memory provided in an external device. If the subject carries a receiving device having the radio communication function and the memory function, the subject swallows the capsule endoscope and then can freely move until the endoscope is discharged. After the capsule endoscope is discharged, a doctor or a nurse can perform diagnosis by displaying the images of the internal organs based on the image data stored in the memory (see, for example, Japanese Patent Application Laid-open No. 2003-19111).

Further, in the conventional capsule endoscope system, one having a mechanism for detecting the position of the capsule endoscope in the body cavity has been proposed. For example, a magnetic field is generated, which has the position dependency regarding strength inside the subject into which the capsule endoscope is introduced, and the position of the capsule endoscope in the subject can be detected based on the magnetic field strength detected by a magnetic field sensor incorporated in the capsule endoscope. In such a capsule endoscope system, a configuration in which a predetermined coil is arranged outside the subject is adopted to generate the magnetic field, and by allowing predetermined electric current to flow to the coil, the magnetic field is generated inside the subject. Since it is difficult to detect the position of the capsule endoscope beforehand, the magnetic field to be generated needs to be generated so that the capsule endoscope has detectable strength in all areas where the capsule endoscope can be present inside the subject. Specifically, in the conventional capsule endoscope system, a magnetic field capable of detecting the capsule endoscope is generated in all the digestive organs from an oral cavity to an anus.

However, the conventional capsule endoscope system including a position detecting mechanism has a problem in that power consumption greatly increases. That is, to generate the magnetic field having the position dependency regarding the strength in the subject, large current needs to be continuously supplied to the coil over several to ten and odd hours, during which the capsule endoscope stays in the subject. Particularly, in the conventional capsule endoscope system, since the magnetic field having the strength capable of detecting the capsule endoscope is generated with respect to all the digestive organs in the subject, the power required for generating the magnetic field becomes huge, which is not appropriate from the standpoint of reducing the power consumption.

Further, the conventional capsule endoscope system including the position detecting mechanism has another problem in that the power consumption in at least the capsule endoscope increases. Specifically, in the conventional capsule endoscope system, position detection is performed at a constant time interval, and the power consumption increases by a portion of the magnetic field sensor incorporated in a capsule endoscope 2 and driving power of a transmitting mechanism for wirelessly transmitting a detection result of the magnetic field sensor.

Particularly, there is an assumption that it is preferable to form the capsule endoscope as small as possible, to reduce a burden on the subject. Therefore, a small battery or the like incorporated in the capsule endoscope is used, and there is generally a limitation on electric energy to be held. Accordingly, the influence due to an increase of power consumption in the capsule endoscope is larger than in the general electronic equipment, and suppression of increase in power consumption is quite important in the capsule endoscope system.

SUMMARY OF THE INVENTION

A position detecting apparatus according to one aspect of the present invention detects a position of a body-insertable device that is introduced into a subject to acquire intra-subject information while moving inside the subject. The position detecting apparatus includes a linear magnetic-field generator that generates a linear magnetic field in an area inside the subject, the area including the position of the body-insertable device; a diffuse magnetic-field generator that generates a diffuse magnetic field having position dependency on magnetic field direction, in the area inside the subject; a magnetic-field line orientation database in which a correspondence between magnetic field direction and position of the diffuse magnetic field in a reference coordinate axis is recorded; an orientation calculator that acquires linear magnetic-field information and earth magnetism direction at a position of the body-insertable device, and calculates orientation information of the body-insertable device in the reference coordinate axis based on the linear magnetic-field information and the earth magnetism direction; and a position calculator that acquires the linear magnetic-field information, the orientation information, and diffuse magnetic-field information of the diffuse magnetic field at the position of the body-insertable device, calculates a magnetic field direction of the diffuse magnetic field at the position of the body-insertable device based on the linear magnetic-field information, the orientation information, and the diffuse magnetic-field information, and calculates the position of the body-insertable device based on the magnetic field direction and the correspondence recorded in the magnetic-field line orientation database.

A position detecting apparatus according to another aspect of the present invention detects a position of a body-insertable device that is introduced into a subject to acquire intra-subject information while moving inside the subject. The position detecting apparatus includes a linear magnetic-field generator that generates a plurality of linear magnetic fields each having a different magnetic component in magnetic direction, in an area inside the subject, the area including the position of the body-insertable device; a diffuse magnetic-field generator that generates a diffuse magnetic field having position dependency on magnetic field direction, in the area inside the subject; a magnetic-field line orientation database in which a correspondence between magnetic field direction and position of the diffuse magnetic field in a reference coordinate axis is recorded; an orientation calculator that acquires linear magnetic-field information of the plurality of linear magnetic fields at a position of the body-insertable device, and calculates orientation information of the body-insertable device in the reference coordinate axis based on the linear magnetic-field information; and a position calculator that acquires the orientation information, a piece of the linear magnetic-field information, and diffuse magnetic-field information of the diffuse magnetic field at the position of the body-insertable device, calculates a magnetic field direction of the diffuse magnetic field at the position of the body-insertable device based on the piece of the linear magnetic-field information, the orientation information, and the diffuse magnetic-field information, and calculates the position of the body-insertable device based on the magnetic field direction and the correspondence recorded in the magnetic-field line orientation database.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A position detecting apparatus and a body-insertable apparatus system according to best modes for carrying out the present invention (hereinafter, simply "embodiments") will be explained below. Note that the drawings are schematic, and that a relationship between a thickness and a width of each part, and a rate of a thickness of each part are different from actual products. Needless to mention, in some parts, a size relationship and rates are different between the drawings. In the explanations below, a technique using a first linear magnetic field, a second linear magnetic field, and a diffuse magnetic field as a mechanism for position detection is explained. However, it is needless to mention that the present invention is not limited to such a configuration, and the present invention is applicable to a position detecting apparatus of a detected object, which uses a position detecting magnetic field having position dependency over a plurality of time instants. In the embodiments described below, the second linear magnetic field is explained as an example of the position detecting magnetic field in the claims, and a second linear magnetic field generating unit that generates the second linear magnetic field is explained as a magnetic field generating unit in the claims. However, as described below, the present invention is also applicable to other magnetic fields and other magnetic field generating units.

A body-insertable apparatus system according to a first embodiment is explained first. In the first embodiment, an overall configuration and respective components of the body-insertable apparatus system are explained, and a position detection mechanism is explained. A control mechanism relating to strength of the position detecting magnetic field used for position detections is then explained.

Figure 1:
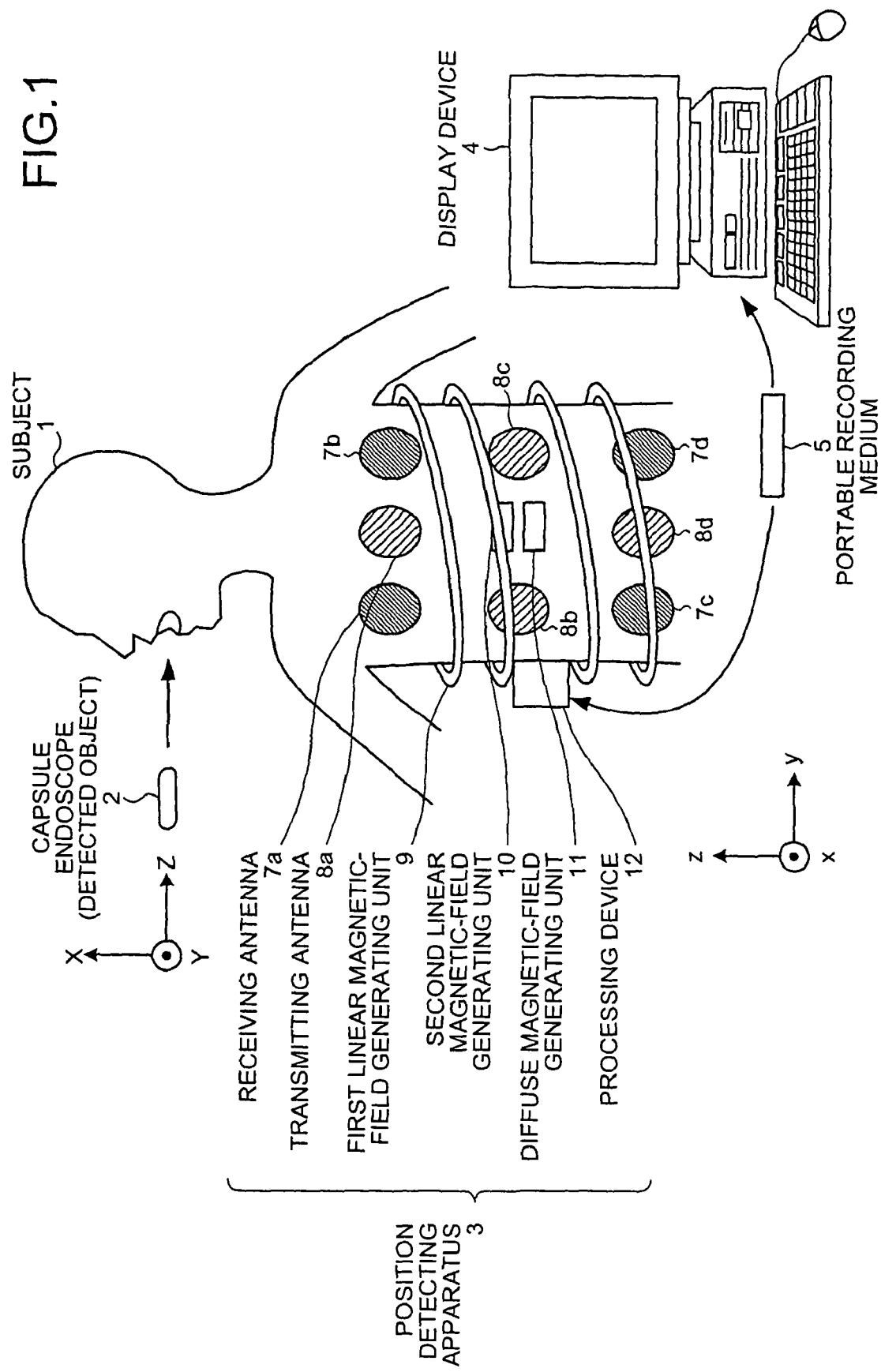
FIG. 1 is a schematic diagram of an overall configuration of a body-insertable apparatus system according to a first embodiment.

FIG. 1 is a schematic diagram of an overall configuration of the body-insertable apparatus system according to the first embodiment. As shown in FIG. 1, the body-insertable apparatus system according to the first embodiment includes a capsule endoscope 2, which is introduced into a subject 1 and moves along a passage route, a position detecting apparatus 3 that performs radio configuration with the capsule endoscope 2 and detects a positional relationship between a target coordinate axis fixed to the capsule endoscope 2 and a reference coordinate axis fixed to the subject 1, a display device 4 that displays a content of a radio signal transmitted from the capsule endoscope 2 and received by the position detecting apparatus 3, and a portable recording medium 5 for transferring information between the position detecting apparatus 3 and the display device 4. As shown in FIG. 1, in the first embodiment, the target coordinate axis, which is a coordinate axis formed of X-axis, Y-axis, and Z-axis and fixed to the capsule endoscope 2, and the reference coordinate axis, which is a coordinate axis formed of x-axis, y-axis, and z-axis, and is set regardless of the movement of the capsule endoscope 2, and specifically, is fixed to the subject 1 are set, to detect the position relationship of the target coordinate axis with respect to the reference coordinate axis by using a mechanism explained below.

The display device 4 displays an intra-subject image and the like imaged by the capsule endoscope 2 and received by the position detecting apparatus 3, and has a configuration like a workstation that displays an image based on data obtained by the portable recording medium 5. Specifically, the display device 4 can have a configuration of directly displaying the image and the like by a CRT display, a liquid crystal display, or the like, or a configuration of outputting the image and the like to another medium like a printer.

The portable recording medium 5 is detachable to a processing device 12 and the display device 4, and has a structure capable of outputting and recording information, when it is set in the processing device 12 and the display device 4. Specifically, the portable recording medium 5 is set in the processing device 12 to store the intra-subject images and the position of the target coordinate axis relative to the reference coordinate axis, when the capsule endoscope 2 is moving in a body cavity of the subject 1. After the capsule endoscope 2 is discharged from the subject 1, the portable recording medium 5 is taken out from the processing device 12 and set in the display device 4, and the recorded data is read by the display device 4. Since transfer of data between the processing device 12 and the display device 4 is performed by the portable recording medium 5 such as a CompactFlash® memory, the subject 1 can freely move even while the capsule endoscope 2 is moving in the subject 1, different from a case where the processing device 12 and the display device 4 are connected with each other by wire.

The capsule endoscope 2 is explained next. The capsule endoscope 2 functions as an example of a detected object in the claims. Specifically, the capsule endoscope 2 is introduced into the subject 1, moves along the passage route to acquire the intra-subject information, and transmits a radio signal including the acquired intra-subject information to the outside. The capsule endoscope 2 has a magnetic-field detecting function for detecting the position relationship, and is supplied with a driving power from outside. Specifically, the capsule endoscope 2 has functions of receiving the radio signal transmitted from outside, and reproducing the received radio signal as the driving power.

Figure 2:
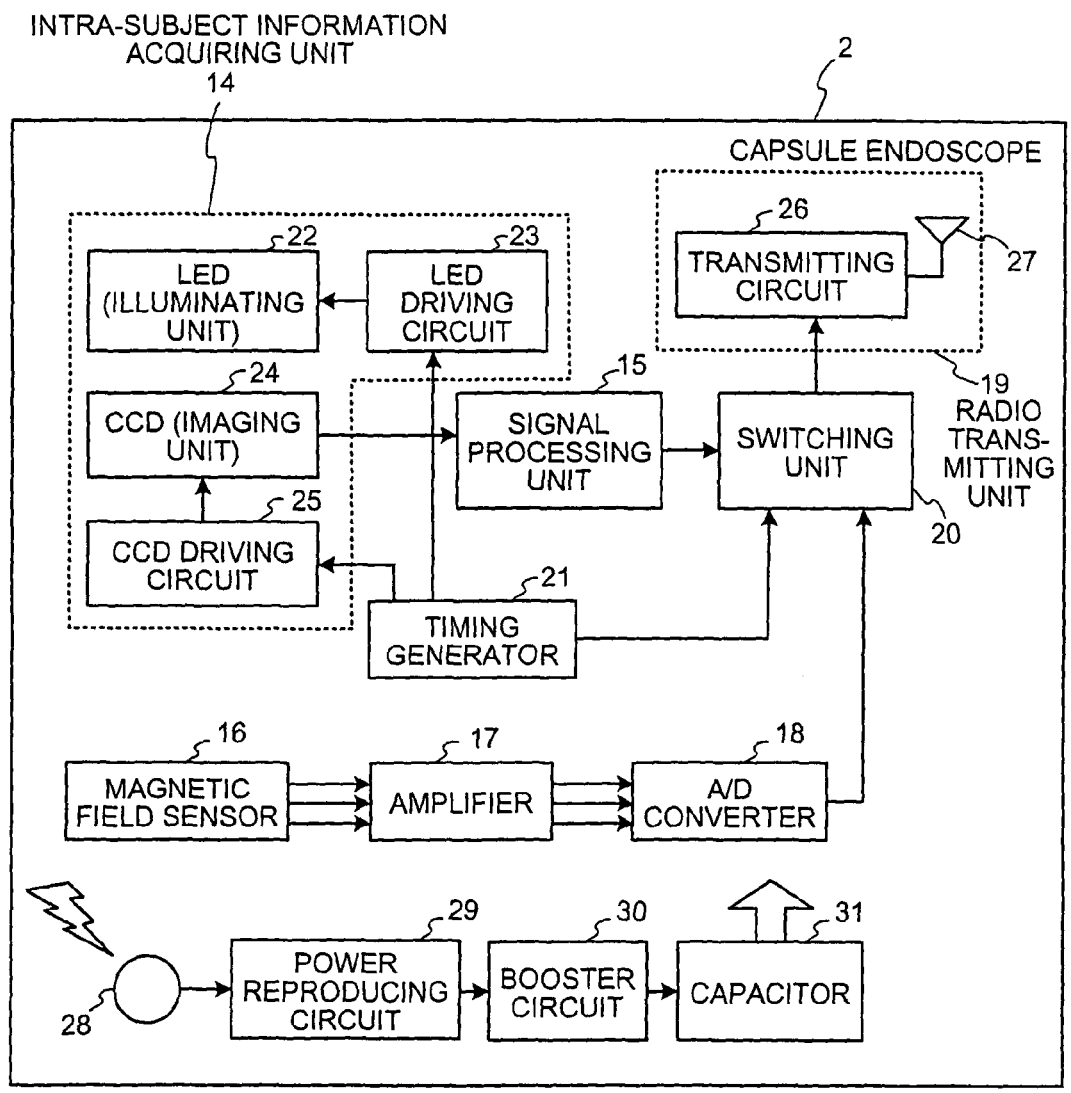
FIG. 2 is a schematic block diagram of a configuration of a capsule endoscope included in the body-insertable apparatus system.

FIG. 2 is a block diagram of a configuration of the capsule endoscope 2. As shown in FIG. 2, the capsule endoscope 2 includes an intra-subject information acquiring unit 14 that acquires the intra-subject information as a mechanism for acquiring the intra-subject information and a signal processing unit 15 that performs predetermined processing to the acquired intra-subject information. The capsule endoscope 2 also includes a magnetic field sensor 16 that detects the magnetic field as a magnetic field detecting mechanism and outputs an electric signal corresponding to the detected magnetic field, an amplifier 17 that amplifies the output electric signal, and an A/D converter 18 that converts the electric signal output from the amplifier 17 to a digital signal.

The intra-subject information acquiring unit 14 acquires the intra-subject information, and in the first embodiment, for acquiring intra-subject images as the image data of the subject body. Specifically, the intra-subject information acquiring unit 14 includes an LED 22 that functions as an illuminating unit, an LED driving circuit 23 that controls driving of the LED 22, a CCD 24 that functions as an imaging unit that images at least a part of an area illuminated by the LED 22, and a CCD driving circuit 25 that controls the driving state of the CCD 24. As a specific configuration of the illuminating unit and the imaging unit, the use of the LED and the CCD are not essential, and for example, a CMOS or the like can be used as the imaging unit.

The magnetic field sensor 16 detects an orientation and strength of the magnetic field formed in a presence area of the capsule endoscope 2. Specifically, the magnetic field sensor 16 is formed by using, for example, a Magneto-Impedance (MI) sensor. The MI sensor has, for example, a configuration in which a FeCoSiB amorphous wire is used as a magneto-sensitive medium, and the magnetic field strength is detected by using such an MI effect that when high-frequency electric current is supplied to the magneto-sensitive medium, a magnetic impedance of the magneto-sensitive medium largely changes due to an external magnetic field. The magnetic field sensor 16 can be constituted by using, for example, a magneto-resistance effect (MRE) element, or a giant magneto-resistance effect (GMR) magnetic sensor, other than the MI sensor.

As shown in FIG. 1, in the first embodiment, the target coordinate axis specified by X-axis, Y-axis, and Z-axis is assumed as the coordinate axis of the capsule endoscope 2, which is the detected object. The magnetic field sensor 16 has functions of detecting the magnetic field strength of an X-direction component, a Y-direction component, and a Z-direction component, regarding the magnetic field generated in an area where the capsule endoscope 2 is positioned, corresponding to the target coordinate axis, and outputting an electric signal corresponding to the magnetic field strength in the respective directions. The magnetic field strength components in the target coordinate axis detected by the magnetic field sensor 16 is transmitted to the position detecting apparatus 3 via a radio transmitting unit 19, and the position detecting apparatus 3 calculates the position relationship between the target coordinate axis and the reference coordinate axis based on a value of the magnetic field component detected by the magnetic field sensor 16.

The capsule endoscope 2 also includes a transmitting circuit 26 and a transmitting antenna 27, as well as a radio transmitting unit 19 for performing radio transmission to the outside, and a switching unit 20 that appropriately switches the signal to be output to the radio transmitting unit 19 between the signal output from the signal processing unit 15 and the signal output from the A/D converter 18. The capsule endoscope 2 further includes a timing generator 21 for synchronizing the drive timing of the intra-subject information acquiring unit 14, the signal processing unit 15, and the switching unit 20.

The capsule endoscope 2 further includes a receiving antenna 28 as a mechanism for receiving a radio signal for feeding power from outside, an power reproducing circuit 29 that reproduces power from the radio signal received via the receiving antenna 28, a booster circuit 30 that boosts a voltage of a power signal output from the power reproducing circuit 29, and a capacitor 31 that accumulates the power signals changed to a predetermined voltage by the booster circuit 30 and supplies the power signals as the driving power for the other components.

The receiving antenna 28 is formed, for example, by using a loop antenna. The loop antenna is fixed at a predetermined position in the capsule endoscope 2, and specifically, is arranged so as to have predetermined position and orientation in the target coordinate axis fixed to the capsule endoscope 2.

The position detecting apparatus 3 is explained next. The position detecting apparatus 3 includes, as shown in FIG. 1, receiving antennas 7a to 7d for receiving the radio signal transmitted from the capsule endoscope 2, transmitting antennas 8a to 8d for transmitting the radio signal for feeding power to the capsule endoscope 2, a first linear magnetic-field generating unit 9 that generates a first linear magnetic field, a second linear magnetic-field generating unit 10 that generates a second linear magnetic field, a diffuse magnetic-field generating unit 11 that generates a diffuse magnetic field, and the processing device 12 that performs predetermined processing to the radio signal and the like received via the receiving antennas 7a to 7d.

The receiving antennas 7a to 7d receive the radio signal transmitted from the radio transmitting unit 19 included in the capsule endoscope 2. Specifically, the receiving antennas 7a to 7d are formed of a loop antenna or the like, and have a function of transmitting the received radio signal to the processing device 12.

The transmitting antennas 8a to 8d transmit the radio signal generated by the processing device 12 to the capsule endoscope 2. Specifically, the transmitting antennas 8a to 8d are formed of a loop antenna or the like electrically connected to the processing device 12.

It should be noted that the specific configuration of the receiving antennas 7a to 7d, the transmitting antennas 8a to 8d, and the first linear magnetic field generating unit 9 is not limited to the one shown in FIG. 1. That is, FIG. 1 shows these components only schematically, and the number of the receiving antennas 7a to 7d is not limited to the one shown in FIG. 1. The arrangement positions and the specific shape are not limited to those shown in FIG. 1, and an optional configuration can be adopted.

The first linear magnetic field generating unit 9 forms a linear magnetic field in a predetermined direction in the subject 1. The "linear magnetic field" stands for a magnetic field formed of a magnetic field component substantially only in one direction, in at least a predetermined spatial area, in the first embodiment, a spatial area in which the capsule endoscope 2 in the subject 1 can be positioned. Specifically, the first linear magnetic field generating unit 9 includes, as shown in FIG. 1, a coil formed so as to cover a body of the subject 1, and a current source (not shown) that supplies a predetermined electric current to the coil, and has a function of forming the linear magnetic field in the spatial area in the subject 1 by allowing the predetermined electric current to flow to the coil. An optional direction can be selected as a moving direction of the first linear magnetic field, however, in the first embodiment, the first linear magnetic field is a linear magnetic field moving in a z-axis direction in the reference coordinate axis fixed to the subject 1.

Figure 3:
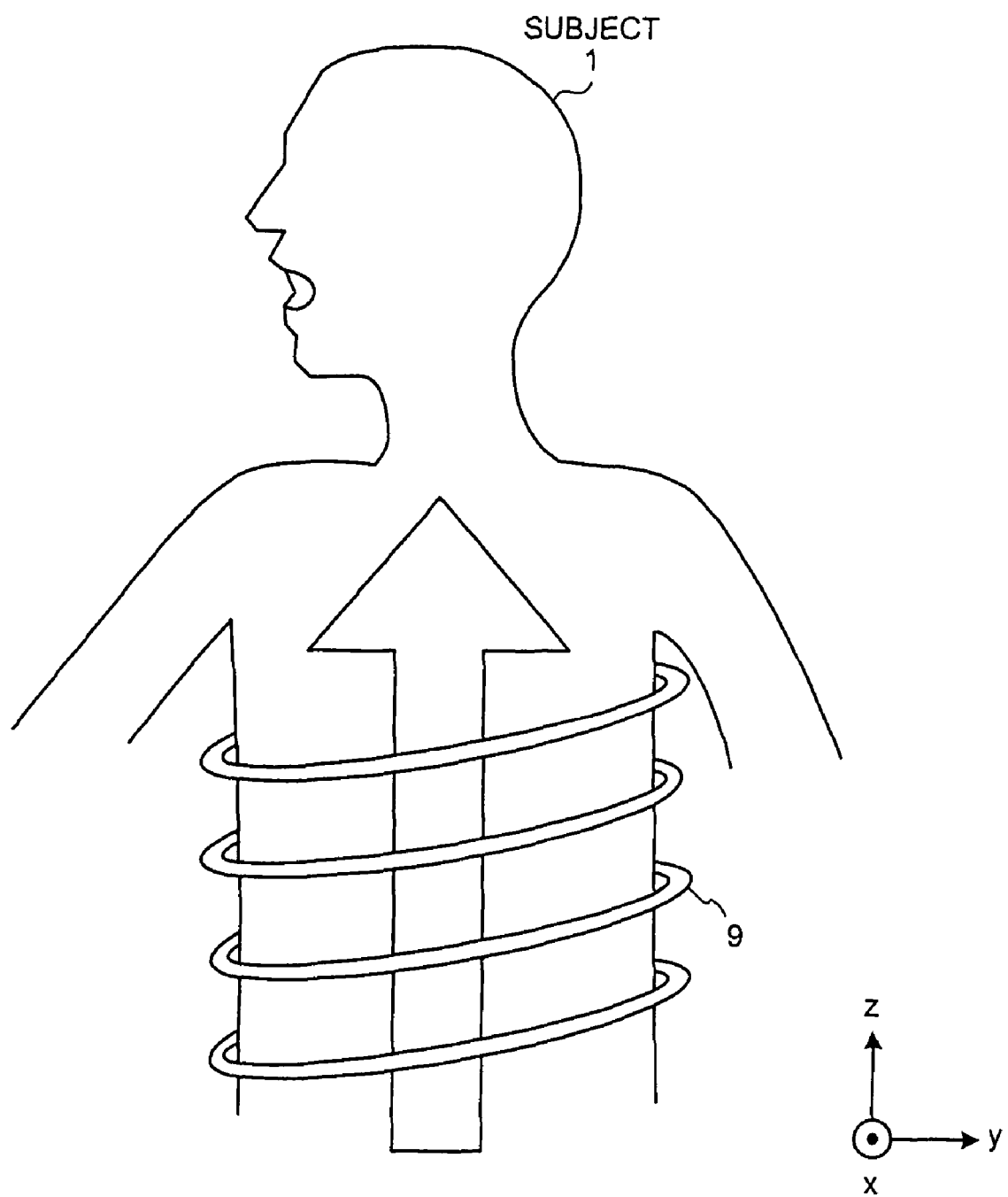
FIG. 3 is a schematic diagram of a first linear magnetic field generated by a first linear magnetic field generating unit included in a position detecting apparatus.

FIG. 3 is a schematic diagram of the first linear magnetic field generated by the first linear magnetic field generating unit 9. As shown in FIG. 3, the coil forming the first linear magnetic field generating unit 9 is formed so as to surround the body of the subject 1, and extends in the z-axis direction in the reference coordinate axis. Accordingly, as shown in FIG. 3, a magnetic-field line moving in the z-axis direction in the reference coordinate axis is formed in the first linear magnetic field generated inside the subject 1 by the first linear magnetic field generating unit 9.

The second linear magnetic-field generating unit 10 and the diffuse magnetic-field generating unit 11 are explained next. The second linear magnetic-field generating unit 10 and the diffuse magnetic-field generating unit 11 respectively function as one example of a magnetic field generating unit in the claims, and the second linear magnetic field and the diffuse magnetic field to be generated function as one example of the position detecting magnetic field in the claims. In the explanation below, the second linear magnetic-field generating unit 10 is explained as an example of the magnetic field generating unit, particularly relating to a specific example. However, as is obvious from the explanation, the diffuse magnetic-field generating unit 11 can be similarly used as the magnetic field generating unit.

The second linear magnetic-field generating unit 10 generates the second linear magnetic field, which is a linear magnetic field moving in a direction different from that of the first linear magnetic field. The diffuse magnetic-field generating unit 11 is different from the first linear magnetic-field generating unit 9 and the second linear magnetic-field generating unit 10, and generates a diffuse magnetic field in which the direction of the magnetic field has position dependency, and in the first embodiment, for generating a magnetic field that diffuses as being away from the diffuse magnetic-field generating unit 11.

Figure 4:
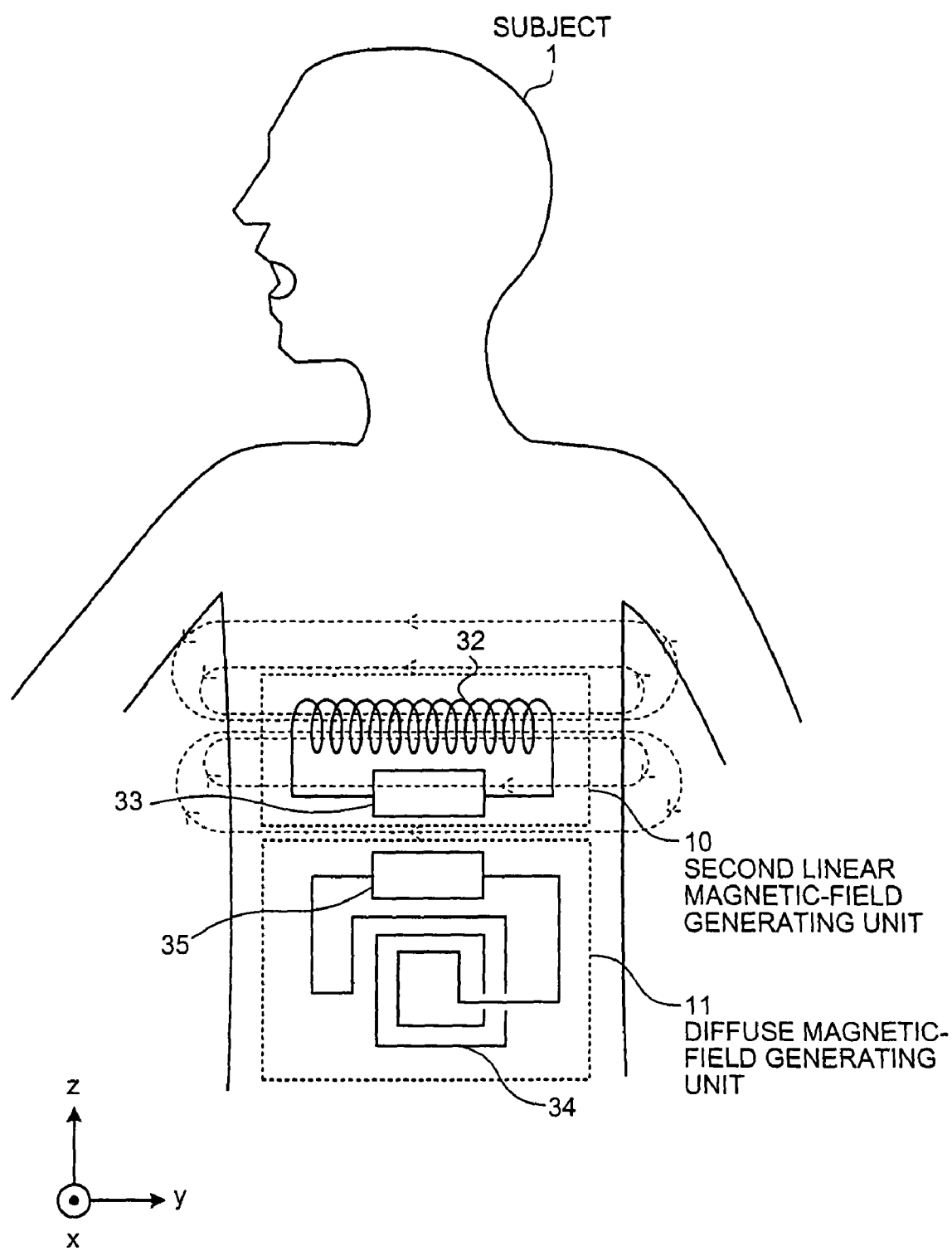
FIG. 4 is a schematic diagram of a configuration of a second linear magnetic field generating unit and a diffuse magnetic-field generating unit included in the position detecting apparatus, and a mode of the second linear magnetic field generated by the second linear magnetic field generating unit.

FIG. 4 is a schematic diagram of a configuration of the second linear magnetic-field generating unit 10 and the diffuse magnetic-field generating unit 11, and a mode of the second linear magnetic field generated by the second linear magnetic-field generating unit 10. As shown in FIG. 4, the second linear magnetic-field generating unit 10 includes a coil 32 extending in the y-axis direction in the reference coordinate axis, and is formed so that a coil section becomes parallel to an xz-plane, and a current source 33 for supplying electric current to the coil 32. Therefore, the second linear magnetic field formed by the coil 32 becomes a linear magnetic field at least in the subject 1, as shown in FIG. 4, and has a characteristic such that the strength gradually attenuates as the second linear magnetic field is away from the coil 32, that is, the position dependency regarding the strength.

The diffuse magnetic-field generating unit 11 also includes a coil 34 and a current source 35 for supplying electric current to the coil 34. The coil 32 is arranged so as to form the magnetic field having a moving direction in a predetermined direction. In the first embodiment, the coil 32 is arranged so that the moving direction of the linear magnetic field formed by the coil 32 becomes the y-axis direction in the reference coordinate axis. Further, the coil 34 is fixed at a position forming the same diffuse magnetic field as the magnetic field direction stored in a magnetic-field line orientation database 42.

In the first embodiment, the second linear magnetic-field generating unit 10 and the diffuse magnetic-field generating unit 11 respectively have a function of adjusting the strength of the formed magnetic field, according to the control of a magnetic-field strength controller 50. Specifically, the second linear magnetic-field generating unit 10 and the diffuse magnetic-field generating unit 11 respectively have a function of adjusting the strength of the magnetic field by adjusting a value of the electric current supplied by the current sources 33 and 35 with respect to the control of the magnetic-field strength controller 50.

Figure 5:
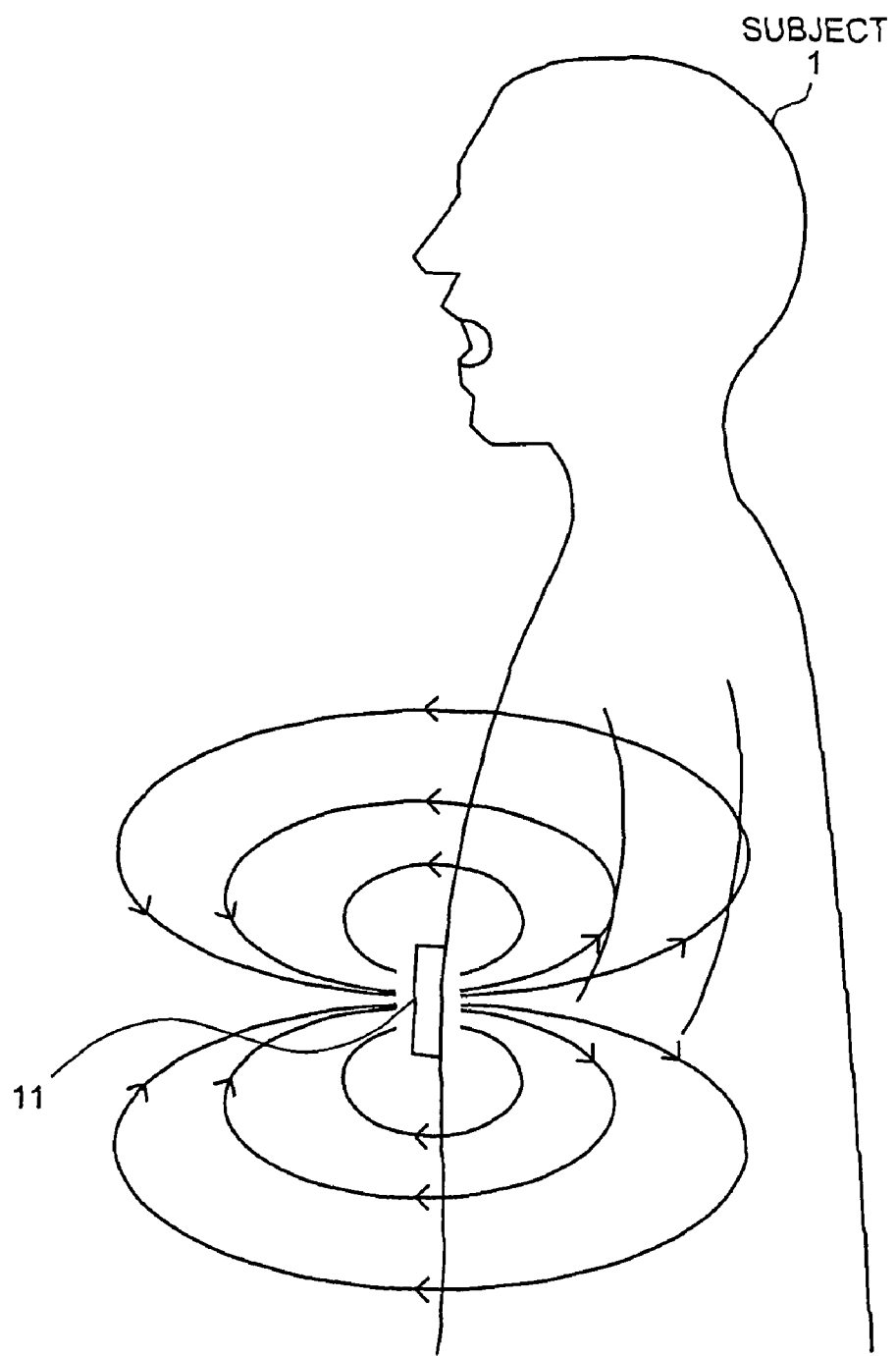
FIG. 5 is a schematic diagram of a mode of the diffuse magnetic field generated by the diffuse magnetic-field generating unit.

FIG. 5 is a schematic diagram of a mode of the diffuse magnetic field generated by the diffuse magnetic-field generating unit. As shown in FIG. 5, the coil 34 included in the diffuse magnetic-field generating unit 11 is formed in a coiled shape on the surface of the subject 1, and the diffuse magnetic field generated by the diffuse magnetic-field generating unit 11 is, as shown in FIG. 5, such that the magnetic-field line radially diffuses once and enters in the coil 34 again, in the magnetic field formed by the coil 34 (not shown in FIG. 5).

In the first embodiment, it is assumed that the first linear magnetic-field generating unit 9, the second linear magnetic-field generating unit 10, and the diffuse magnetic-field generating unit 11 generate the magnetic field at respectively different time instants. In other words, in the first embodiment, the first linear magnetic-field generating unit 9 and the like do not generate the magnetic field simultaneously, but generate the magnetic field according to a predetermined order, and the magnetic field sensor 16 included in the capsule endoscope 2 detects the first linear magnetic field, the second linear magnetic field, and the diffuse magnetic field separately and independently.

Figure 6:
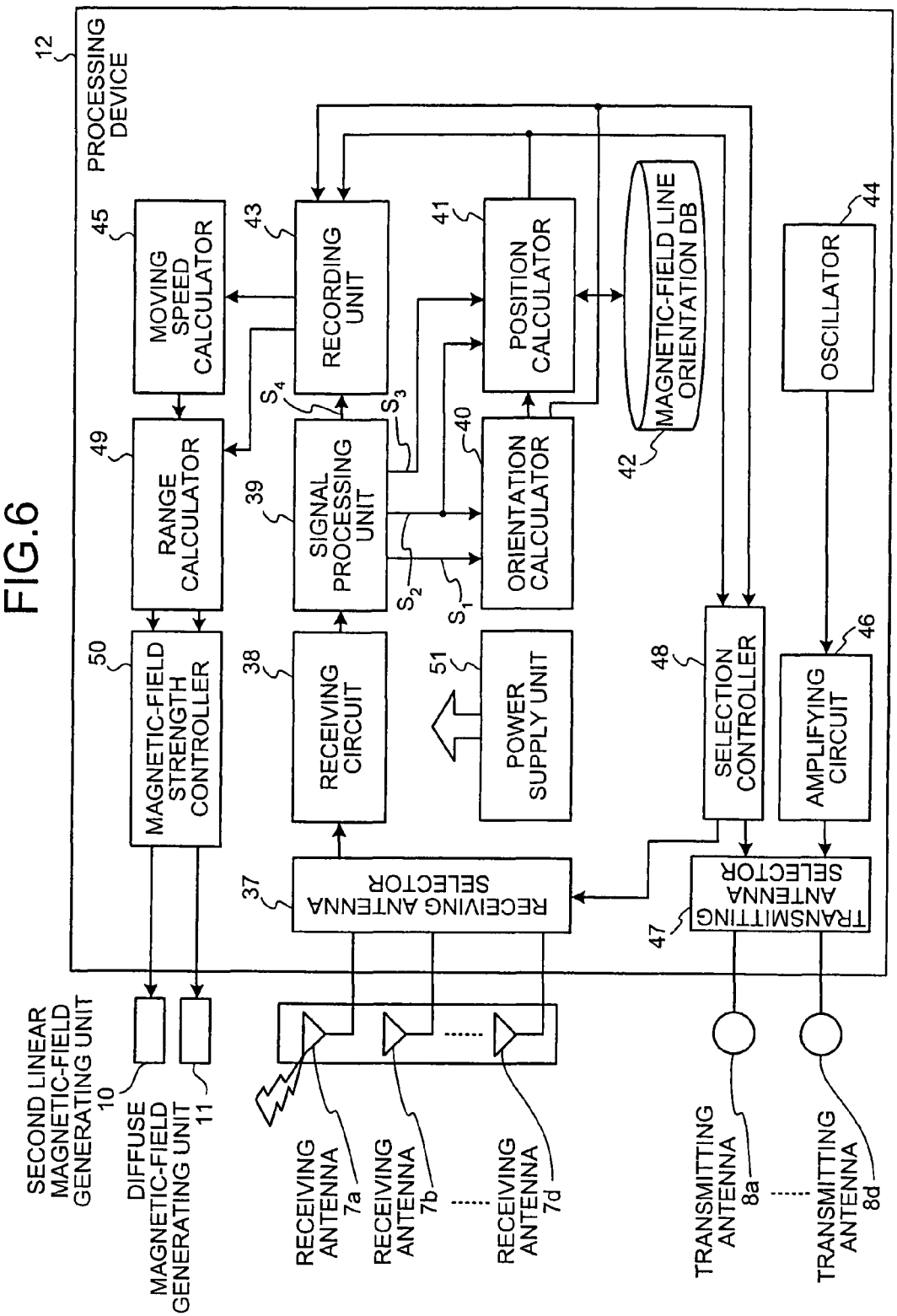
FIG. 6 is a schematic block diagram of a configuration of a processing device included in the position detecting apparatus.

The configuration of the processing device 12 is explained next. FIG. 6 is a schematic block diagram of a configuration of the processing device 12. The processing device 12 has a function of performing receiving processing of the radio signal transmitted by the capsule endoscope 2, and has a receiving antenna selector 37 that selects any one of the receiving antennas 7a to 7d, a receiving circuit 38 that performs demodulation or the like with respect to the radio signal received via the selected receiving antenna to extract an original signal included in the radio signal, and a signal processing unit 39 that reconstructs an image signal and the like by processing the extracted original signal, corresponding to the function.

Specifically, the signal processing unit 39 has a function of reconstructing magnetic field signals S1 to S3 and an image signal S4 based on the extracted original signal, and outputting these signals to an appropriate component respectively. The magnetic field signals S1 to S3 correspond to the first linear magnetic field, the second magnetic field, and the diffusion magnetic field, respectively, detected by the magnetic field sensor 16. The image signal S4 corresponds to the intra-subject image acquired by the intra-subject information acquiring unit 14. The specific mode of the magnetic field signals $S_1$ to $S_3$ is expressed by a direction vector corresponding to the detected magnetic field strength in the target coordinate axis fixed relative to the capsule endoscope 2, and includes information of the moving direction of the magnetic field and the magnetic field strength in the target coordinate axis. The image signal S4 is output to a recording unit 43. The recording unit 43 outputs input data to the portable recording medium 5, and has a function of recording results of position detection and the like as well as the image signal S4 on the portable recording medium 5.

The processing device 12 also has a function of detecting the position of the capsule endoscope 2 in the subject 1 based on the magnetic field strength or the like detected by the capsule endoscope 2, and a function of detecting an orientation of the target coordinate axis fixed to the capsule endoscope 2 relative to the reference coordinate axis fixed to the subject 1. Specifically, the processing device 12 includes an orientation calculator 40 that calculates the orientation of the target coordinate axis relative to the reference coordinate axis based on the magnetic field signals $S_1$ and $S_2$ corresponding to the detected strength of the first linear magnetic field and the second linear magnetic field, of the signals transmitted by the capsule endoscope 2 and output by the signal processing unit 39, a position calculator 41 that calculates the position of the capsule endoscope 2 by using the magnetic field signal $S_3$ corresponding to the detected strength of the diffuse magnetic field, the magnetic field signal $S_2$, and a calculation result of the orientation calculator 40, and the magnetic-field line orientation database 42 in which the correspondence between the moving direction and the position of the magnetic-field line constituting the diffuse magnetic field is recorded at the time of calculating the position by the position calculator 41. Orientation calculation and position calculation by these components will be explained later in detail.

The processing device 12 has a function of wirelessly transmitting driving power to the capsule endoscope 2, and includes an oscillator 44 that specifies the frequency of the transmitted radio signal, an amplifying circuit 46 that amplifies the strength of the radio signal output from the oscillator 44, and a transmitting antenna selector 47 that selects a transmitting antenna used for transmission of the radio signal. The radio signal is received by the receiving antenna 28 included in the capsule endoscope 2, and functions as the driving power of the capsule endoscope 2.

The processing device 12 includes a selection controller 48 that controls an antenna selection mode by the receiving antenna selector 37 and the transmitting antenna selector 47. The selection controller 48 has a function of selecting the transmitting antenna 8 and the receiving antenna 7 most suitable for the transfer with respect to the capsule endoscope 2, based on the orientation and position of the capsule endoscope 2, respectively, calculated by the orientation calculator 40 and the position calculator 41.

The processing device 12 also has a function of controlling the strength of the magnetic field generated by the second linear magnetic-field generating unit 10 and the diffuse magnetic-field generating unit 11. Specifically, the processing device 12 includes a moving speed calculator 45 that calculates moving speed of the capsule endoscope 2 based on a history of the position of the capsule endoscope 2 recorded in the recording unit 43, a range calculator 49 that calculates a range in which the capsule endoscope 2 is positioned based on the calculated moving speed and the past positions of the capsule endoscope 2, and a magnetic-field strength controller 50 that controls the strength of the magnetic field generated by the second linear magnetic-field generating unit 10 and the diffuse magnetic-field generating unit 11 based on the calculated range. The functions of the moving speed calculator 45 and the range calculator 49 will be explained later in detail. The processing device 12 further includes a power supply unit 51 for supplying the driving power to these components.

An operation of the body-insertable apparatus system according to the first embodiment is explained next. After a position detection mechanism of the capsule endoscope 2 as the detected object is first explained, and then, a strength control mechanism of the second linear magnetic field and the diffuse magnetic field used for position calculation and the like is explained, and lastly, the operation as a whole is explained.

First, the position detection mechanism of the capsule endoscope 2 is explained. The body-insertable apparatus system according to the first embodiment has such a configuration that the position relationship is calculated between the reference coordinate axis fixed to the subject 1 and the target coordinate axis fixed to the capsule endoscope 2. Specifically, after the orientation of the target coordinate axis relative to the reference coordinate axis is calculated, the position of an origin of the target coordinate axis relative to the reference coordinate axis, that is, the position of the capsule endoscope 2 inside the subject 1 is calculated. Therefore, after the orientation calculation mechanism is first explained, the position calculation mechanism using the calculated orientation is explained in the following explanation. However, it is a matter of course that the application of the present invention is not limited to a system having such a position detection mechanism.

Figure 7:
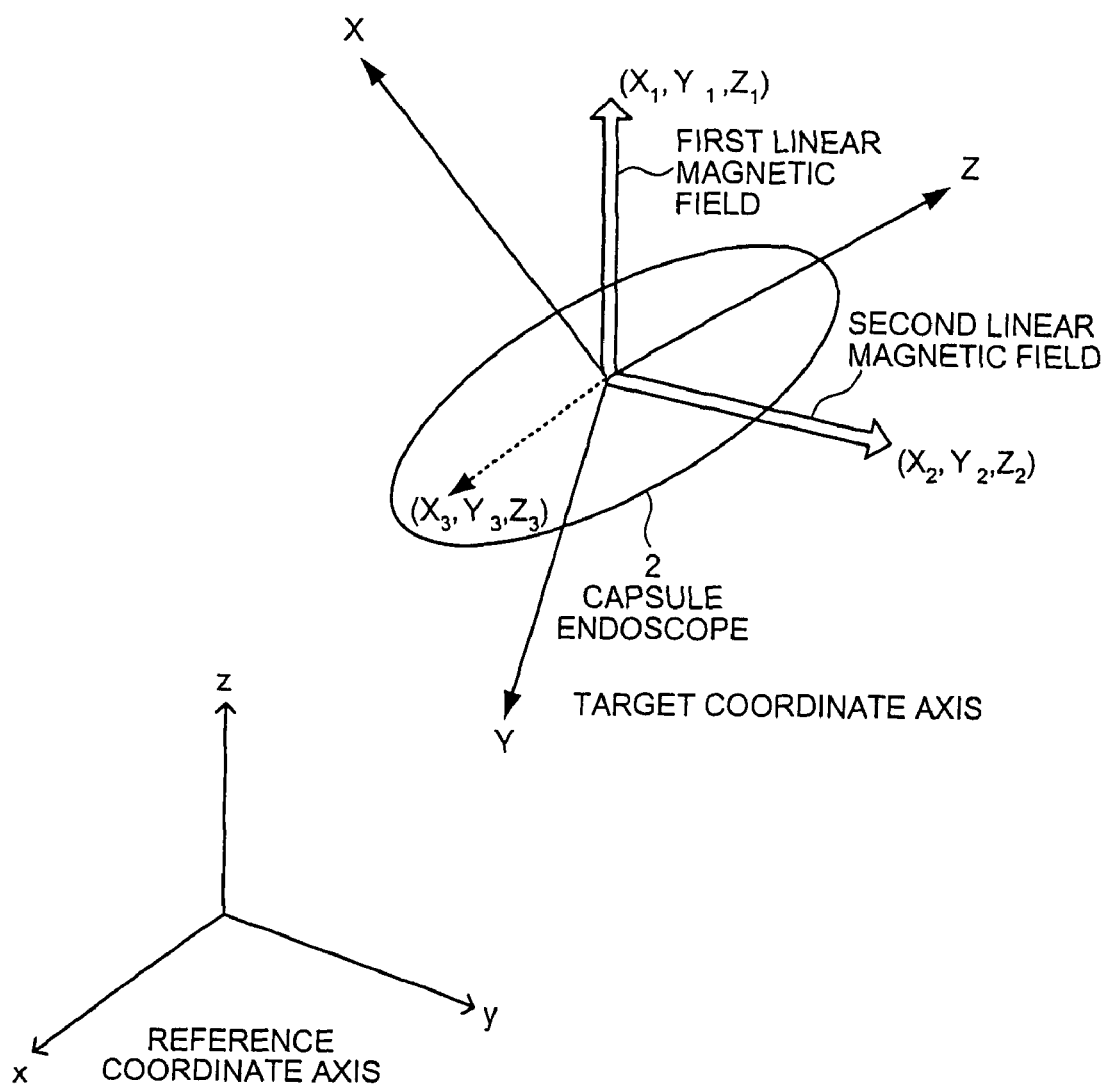
FIG. 7 is a schematic diagram of a relationship between a reference coordinate axis and a target coordinate axis.

The orientation calculation mechanism performed by the orientation calculator 40 is explained. FIG. 7 is a schematic diagram of a relationship between the reference coordinate axis and the target coordinate axis when the capsule endoscope 2 is moving in the subject 1. As explained above, the capsule endoscope 2 is rotating by a predetermined angle, designating the moving direction as an axis, while moving along the passage route in the subject 1. Accordingly, the target coordinate axis fixed to the capsule endoscope 2 generates a deviation of the orientation as shown in FIG. 7, relative to the reference coordinate axis fixed to the subject 1.

On the other hand, the first linear magnetic-field generating unit 9 and the second linear magnetic-field generating unit 10 are fixed, respectively, relative to the subject 1. Therefore, the first and the second linear magnetic fields generated by the first linear magnetic-field generating unit 9 and the second linear magnetic-field generating unit 10 travel in a fixed direction relative to the reference coordinate axis, more specifically, the first linear magnetic field travels in the z-axis direction, and the second linear magnetic field travels in the y-axis direction in the reference coordinate axis.

Orientation calculation in the first embodiment is performed by using the first linear magnetic field and the second linear magnetic field. Specifically, the moving direction of the first linear magnetic field and the second linear magnetic field supplied in a time sharing manner is detected by the magnetic field sensor 16 included in the capsule endoscope 2. The magnetic field sensor 16 is configured so as to detect the magnetic field components in the X-axis direction, the Y-axis direction, and the Z-axis direction in the target coordinate axis, and information of the moving direction of the detected first and second linear magnetic fields in the target coordinate axis is transmitted to the position detecting apparatus 3 via the radio transmitting unit 19.

The radio signal transmitted by the capsule endoscope 2 is output as magnetic field signals $S_1$ and $S_2$ through the processing by the signal processing unit 39 and the like. For example, in the example shown in FIG. 7, the magnetic field signal $S_1$ includes information of a coordinate $(X_1, Y_1, Z_1)$ as the moving direction of the first linear magnetic field, and the magnetic field signal $S_2$ includes information of a coordinate $(X_2, Y_2, Z_2)$ as the moving direction of the second linear magnetic field. On the other hand, the orientation calculator 40 calculates the orientation of the target coordinate axis relative to the reference coordinate axis, upon reception of inputs of these magnetic field signals $S_1$ and $S_2$. Specifically, the orientation calculator 40 ascertains that a coordinate ($X_3$, $Y_3$, $Z_3$) in which a value of an inner product with respect to both ($X_1$, $Y_1$, $Z_1$) and ($X_2$, $Y_2$, $Z_2$) in the target coordinate axis becomes zero corresponds to the direction of the z-axis in the reference coordinate axis. The orientation calculator 40 then performs predetermined coordinate conversion processing based on the above correspondence, to calculate the coordinate in the reference coordinate axis of the X-axis, the Y-axis, and the Z-axis in the target coordinate axis, and outputs such a coordinate as the orientation information. This is the orientation calculation mechanism by the orientation calculator 40.

The position calculation mechanism of the capsule endoscope 2 by the position calculator 41 is explained next. The position calculator 41 has a configuration such that magnetic field signals $S_2$ and $S_3$ are input from the signal processing unit 39, the orientation information is input from the orientation calculator 40, and information stored in the magnetic-field line orientation database 42 is input. The position calculator 41 calculates the position of the capsule endoscope 2 in the following manner, based on these pieces of input information.

Figure 8:
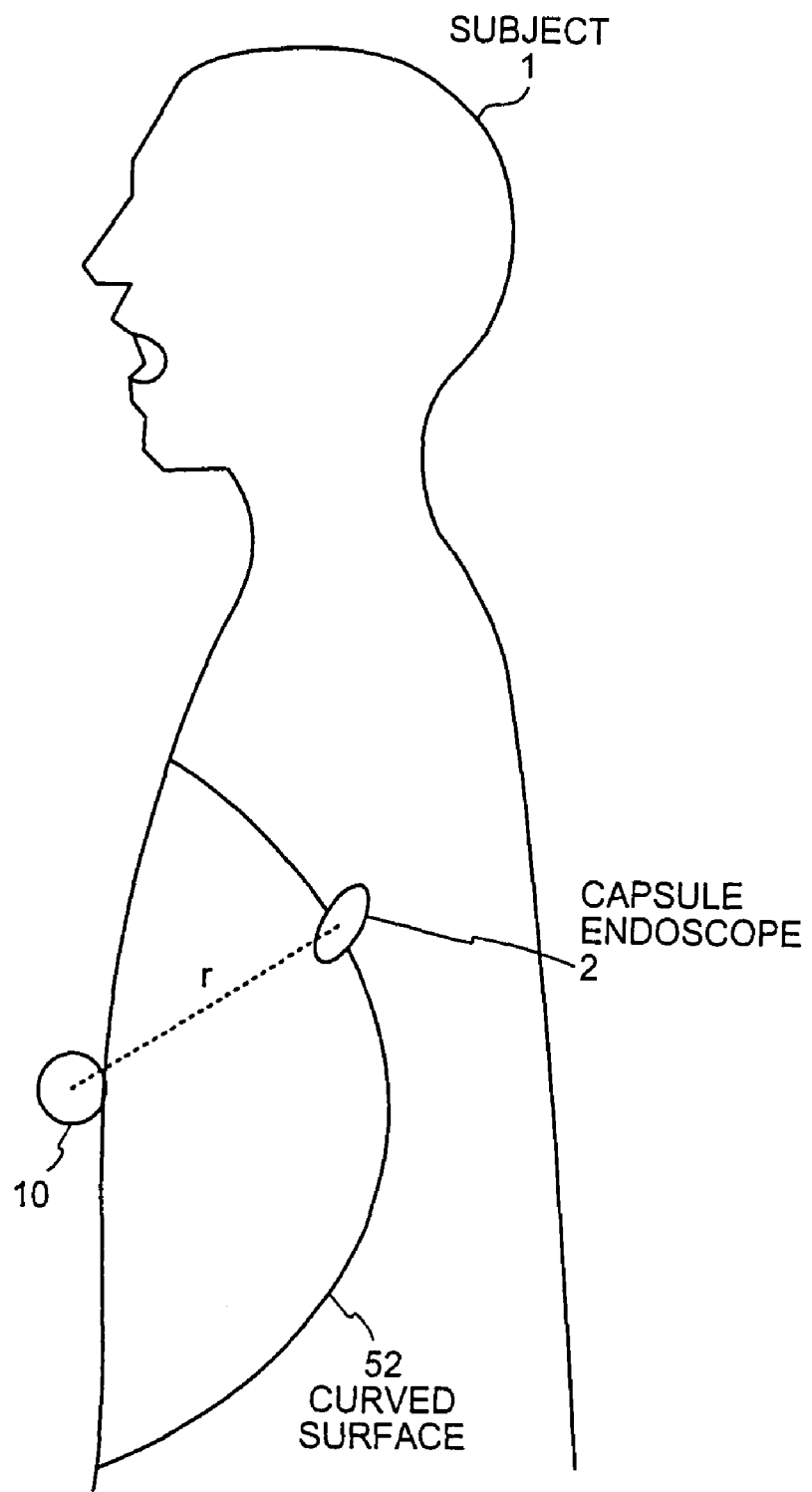
FIG. 8 is a schematic diagram of a use mode of the second linear magnetic field at the time of position calculation.

At first, the position calculator 41 calculates the distance between the second linear magnetic-field generating unit 10 and the capsule endoscope 2 by using the magnetic field signal $S_2$. The magnetic field signal $S_2$ corresponds to the detection result of the second linear magnetic field in the area where the capsule endoscope 2 is present. The second linear magnetic field has a such characteristic that the strength thereof gradually attenuates as the second linear magnetic field is away from the second linear magnetic-field generating unit 10, corresponding to the second linear magnetic-field generating unit 10 being arranged outside of the subject 1. By using such a characteristic, the position calculator 41 compares the strength of the second linear magnetic field near the second linear magnetic-field generating unit 10 (obtained from a current value of the current allowed to flow to the second linear magnetic-field generating unit 10) with the strength of the second linear magnetic field in the area where the capsule endoscope 2 is present obtained from the magnetic field signal $S_2$, to calculate a distance r between the second linear magnetic-field generating unit 10 and the capsule endoscope 2. As a result of calculation of the distance r, as shown in FIG. 8, it becomes obvious that the capsule endoscope 2 is positioned on a curved surface 52, which is an aggregate of points away from the second linear magnetic-field generating unit 10 by the distance r.

Figure 9:
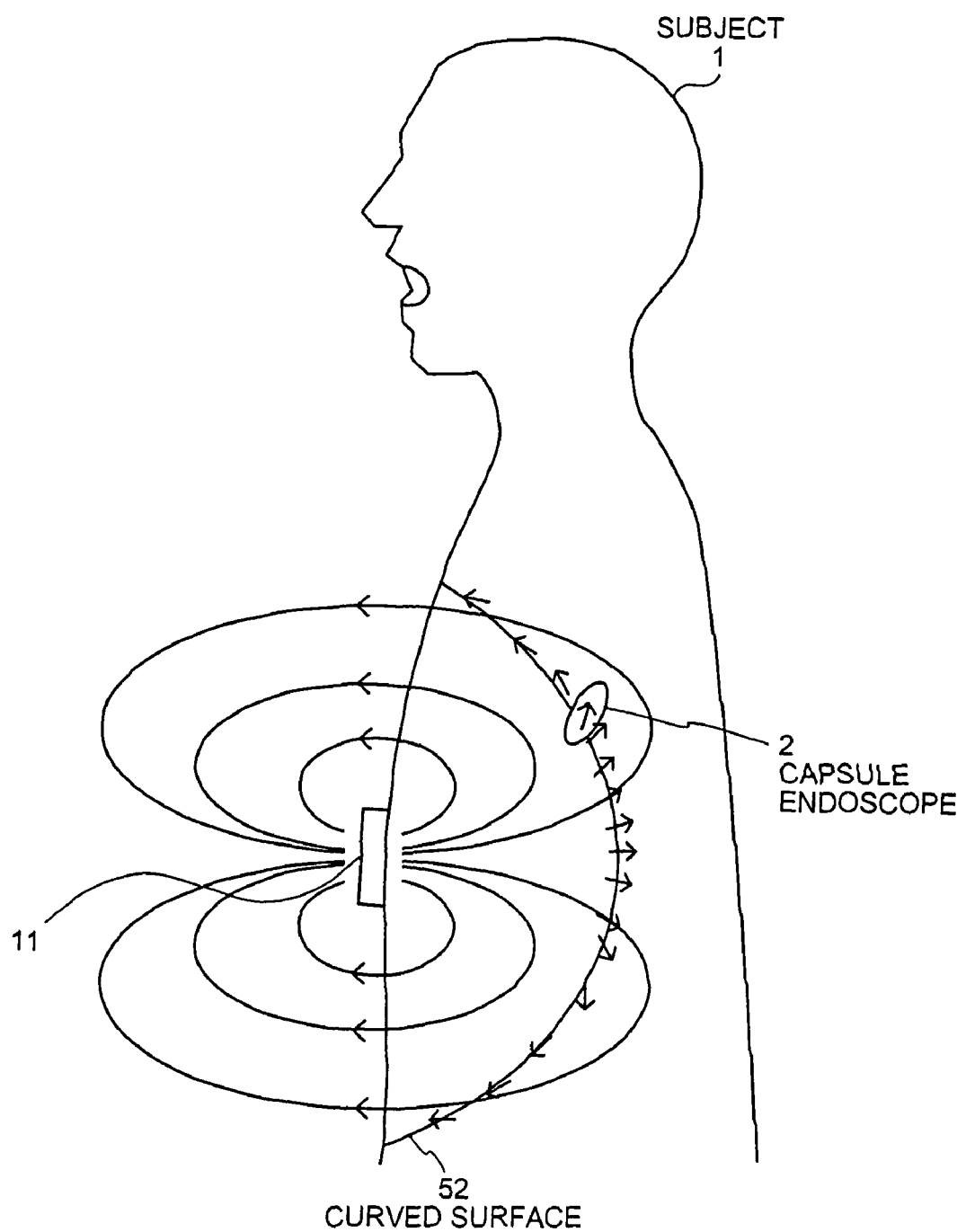
FIG. 9 is a schematic diagram of a use mode of the diffuse magnetic field at the time of position calculation.

The position calculator 41 then calculates the position of the capsule endoscope 2 on the curved surface 52 based on the magnetic field signal $S_3$, the orientation information calculated by the orientation calculator 40, and the information stored in the magnetic-field line orientation database 42. Specifically, the moving direction of the diffuse magnetic field at the present position of the capsule endoscope 2 is calculated based on the magnetic field signal $S_3$ and the orientation information. Since the magnetic field signal $S_3$ is a signal corresponding to the detection result of the diffuse magnetic field based on the target coordinate axis, the moving direction of the diffuse magnetic field in the reference coordinate axis at the present position of the capsule endoscope 2 is calculated, by applying the coordinate conversion processing from the target coordinate axis to the reference coordinate axis by using the orientation information, with respect to the moving direction of the diffuse magnetic field based on the magnetic field signal $S_3$. The magnetic-field line orientation database 42 stores the correspondence between the moving direction and the position of the diffuse magnetic field in the reference coordinate axis. Therefore, the position calculator 41 calculates, as shown in FIG. 9, the position corresponding to the moving direction of the diffuse magnetic field calculated by referring to the information stored in the magnetic-field line orientation database 42, and specifies the calculated position as the position of the capsule endoscope 2. This is the position calculation mechanism by the position calculator 41.

The strength control of the second linear magnetic field and the diffuse magnetic field is explained next. This control of the magnetic field strength is performed to reduce the consumption of power required for forming the second linear magnetic field and the like used as the position detecting magnetic field. More specifically, the magnetic-field strength control in the first embodiment is performed to reduce the strength of the formed magnetic field so long as the position of the capsule endoscope 2 can be predicted to some extent at the time of position detection, and can be detected by the magnetic field sensor 16 included in the capsule endoscope 2 in the predicted range.

In the first embodiment, the magnetic-field strength control is performed roughly according to the following processes, that is, calculation of the moving speed of the capsule endoscope 2 by the moving speed calculator 45, calculation of the possible existence range of the capsule endoscope 2 by the range calculator 49, and control of the second linear magnetic-field generating unit 10 and the diffuse magnetic-field generating unit 11 based on the possible existence range by the magnetic field controller 50. The calculation of the moving speed, the calculation of the possible existence range, and the control of the second linear magnetic-field generating unit 10 and the like are respectively explained below.

In the following explanation and in FIG. 10, time instant t stands for the time when the position detection is performed, and time instants $t_{-1}$, $t_0$, and $t_1$ of the time instants t are time instants when the position detection has been already performed, that is, the past time instants, and time instant $t_2$ is a time instant corresponding to the position detection to be performed next, and the magnetic-field strength control is performed with respect to the position detection at time instant $t_2$. In other words, in the first embodiment, the "first time instant" in the claims corresponds to time instant $t_1$, and the "second time instant" corresponds to time instant $t_2$, and the "plurality of past time instants" corresponds to time instants $t_{-1}$, $t_0$, and $t_1$.

Figure 10:
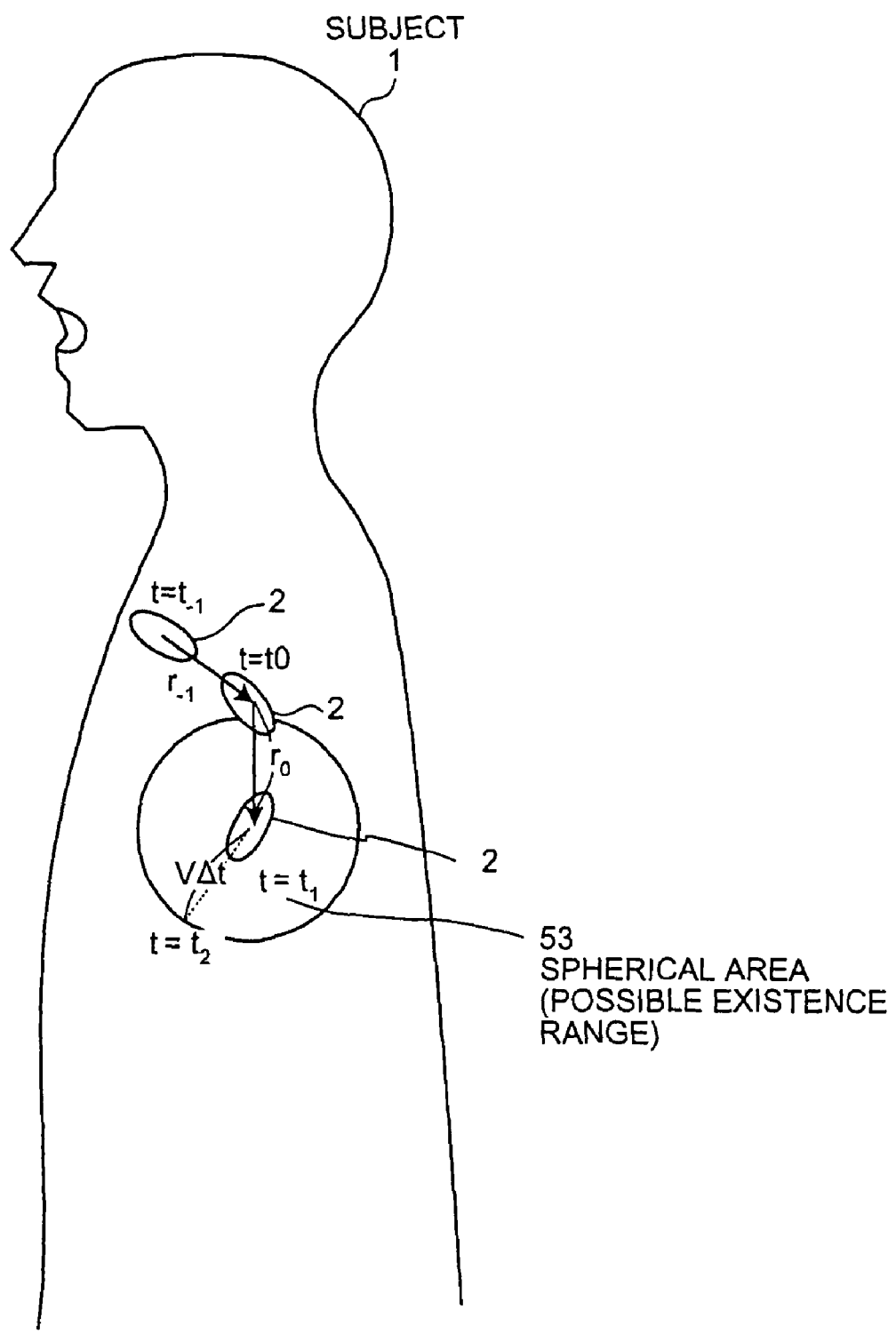
FIG. 10 is a schematic diagram for explaining a calculation mode of a moving speed and a possible existence range using the moving speed.

FIG. 10 is a schematic diagram for explaining a calculation mechanism of the moving speed and the possible existence range. At first, the moving speed calculator 45 calculates a moving distance $r_{-1}$ at time instants $t_{-1}$ to $t_0$ and a moving distance $r_0$ at time instants $t_0$ to $t_1$ based on the positions at different time instants $t_{-1}$, $t_0$, and $t_1$ recorded in the recording unit 43, to calculate an average moving speed in the past. Specifically, for example, by using an average speed $v_{-1}$ at time instants $t_{-1}$ to $t_0$ and an average speed $v_0$ at time instants $t_0$ to $t_1$, an average value v of the moving speed at time instants $t_1$ to $t_2$ is calculated.

$$v = (v_{-1} + v_0)/2 = (1/2)\{r_{-1}/(t_0 - t_{-1})\} + \{r_0/(t_1 - t_0)\} \quad (1)$$

In the first embodiment, the moving speed at time instants $t_1$ to $t_2$ can be a value other than the one shown in equation (1), so long as it is calculated based on the positions detected at a plurality of past time instants, and for example, as the simplest configuration, the moving speed at time instants $t_1$ to $t_2$ can be calculated, designating v as $v = v_0$.

The range calculator 49 calculates the possible existence range of the capsule endoscope 2 at time instant $t_2$ based on the moving speed calculated by the moving speed calculator

45. The range calculator 49 then calculates the possible existence range, as shown in FIG. 10, as a spherical area 53 whose radius has a value obtained by multiplying the calculated moving speed by elapsed time $\Delta t$ ($=t_2-t_1$) from time instant $t_1$ to time instant $t_2$, centering on the position of the capsule endoscope 2 detected at time instant $t_1$. That is, in the first embodiment, the range calculator 49 presumes that the capsule endoscope 2 is present within the spherical area 53 shown in FIG. 11 at time instant $t_2$.

Figure 11:
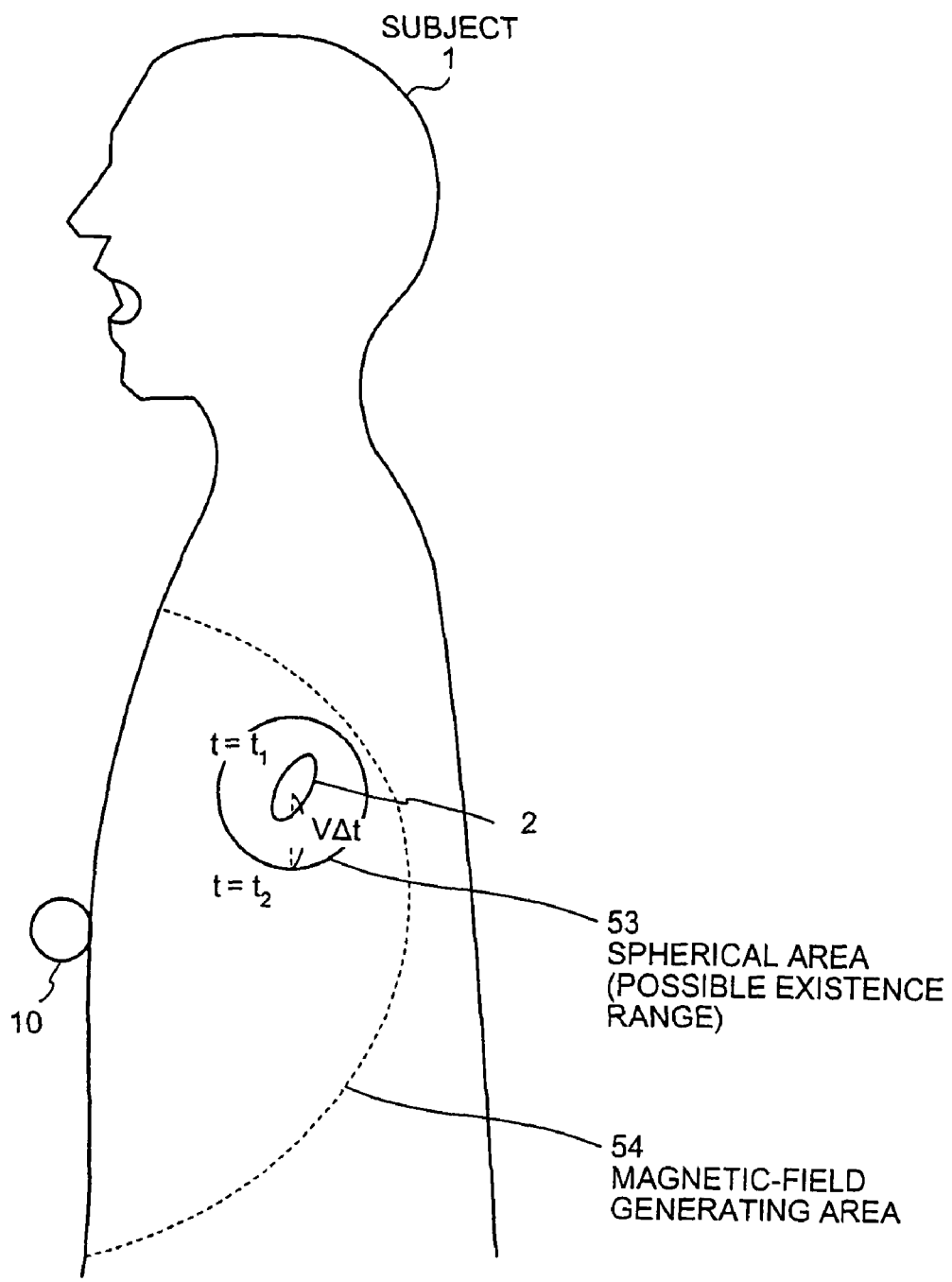
FIG. 11 is a schematic diagram for explaining a magnetic field generating area determined based on the calculated possible existence range.

After the possible existence range is calculated, the magnetic-field strength controller 50 adjusts the strength of the magnetic field generated by the second linear magnetic-field generating unit 10 and the diffuse magnetic-field generating unit 11 so as to cover such an area. FIG. 11 is a schematic diagram of the magnetic-field strength control regarding the second linear magnetic-field generating unit 10, as an example of the control by the magnetic-field strength controller 50. In FIG. 11, the "magnetic-field generating area" stands for an area where a significant magnetic field regarding the position detection is generated, and specifically, stands for an area in which a magnetic field detectable by the magnetic field sensor 16 included in the capsule endoscope 2 is generated. The second linear magnetic-field generating unit 10 generates the magnetic field so that the power consumption becomes the minimum, under a condition that the magnetic-field generating area 54 includes the spherical area 53, under the control of the magnetic-field strength controller 50. Specifically, since the second linear magnetic field has such a characteristic that the strength thereof attenuates gradually as the second linear magnetic field is away from the second linear magnetic-field generating unit 10, the second linear magnetic-field generating unit 10 generates the magnetic field so that the farthest portion of the spherical area 53 overlaps on a margin of the magnetic-field generating area 54. This is the magnetic-field strength control by the magnetic-field strength controller 50.

Figure 12:
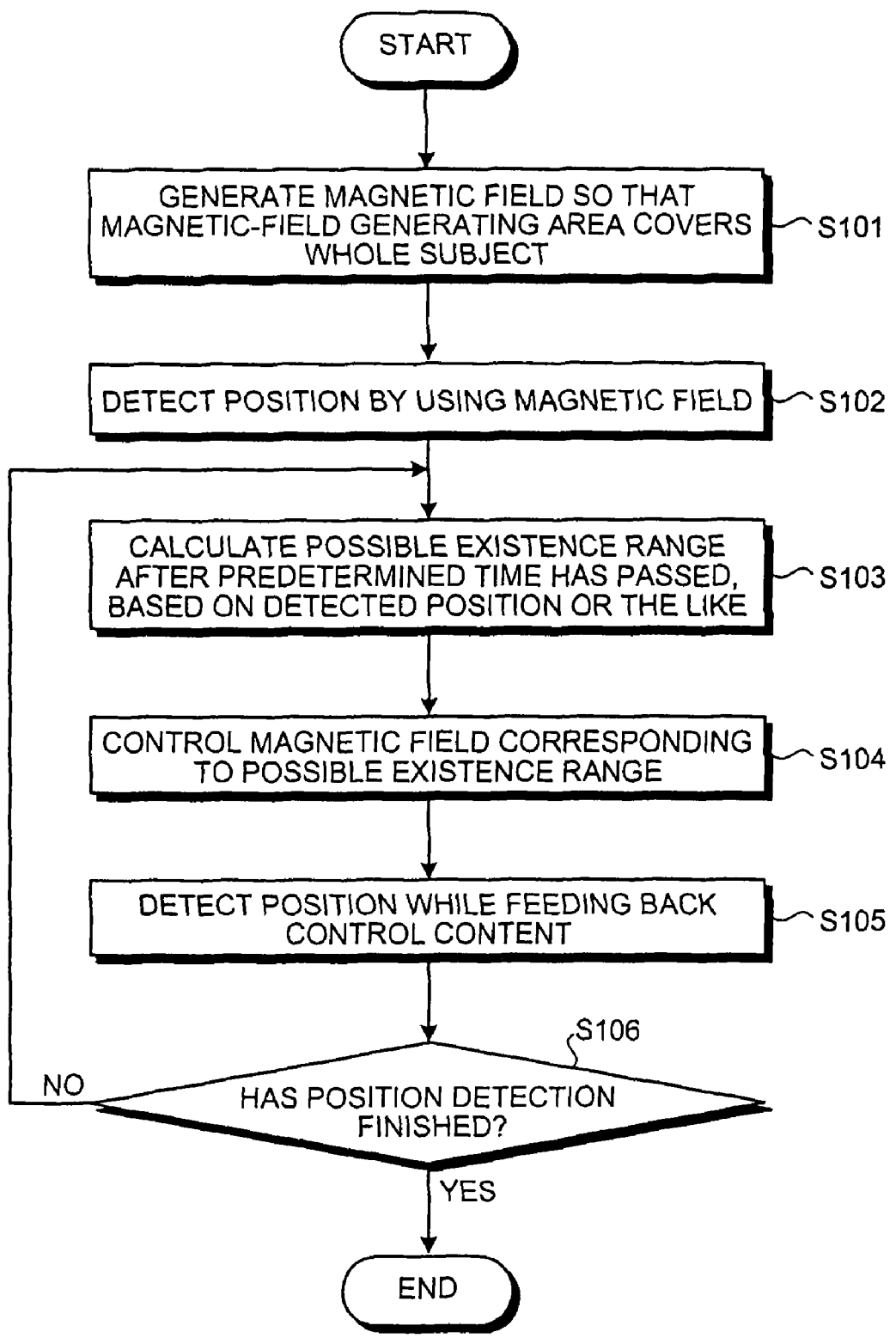
FIG. 12 is a flowchart for explaining an operation of the processing device.

The processing device 12 operates according to a flowchart shown in FIG. 12, by using the position detection mechanism and the magnetic-field strength control mechanism. At first, the magnetic-field strength controller 50 controls the second linear magnetic-field generating unit 10 and the like so that the magnetic-field generating area covers the whole subject 1 to perform the first position detection, and the magnetic field corresponding to such a control is generated (step S101). By using the generated magnetic field, position calculation is performed according to the above mechanisms (step S102), to calculate the possible existence range of the capsule endoscope 2 after the predetermined time ($=\Delta t$) since the position detection at step S102 based on the detected position and the like (step S103).

Thereafter, the magnetic-field strength controller 50 sets the magnetic-field generating area corresponding to the possible existence range, controls the second linear magnetic-field generating unit 10 and the like so as to achieve such a magnetic-field generating area (step S104), and calculates the position of the capsule endoscope 2 after lapse of a predetermined time, while feeding back the control content (step S105). The magnetic-field strength controller 50 then determines whether the position detection finishes (step S106), and when the position detection does not finish (step S106, No), returns to step S103 to repeat the above processing. The processing device 12 performs reconfiguration and recording of the intra-subject image data based on the radio signal transmitted from the capsule endoscope 2 and transmission of the driving power to the capsule endoscope 2, corresponding to the above operations. However, since these operations are not the characteristic part of the present invention, the explanation thereof is omitted.

The reason why the magnetic-field generating area is set so as to cover the whole subject at step S101 is that it is difficult to calculate the possible existence range by the above mechanisms at the time of first position detection. That is, in the above mechanisms, since the possible existence range is calculated by using the positions detected in the past, position detection is performed according to the conventional mechanism, regarding the first position detection.

The reason why position calculation by the position calculator 41 is performed while feeding back the control content by the magnetic-field strength controller 50 at step S105 is as follows. That is, in calculation of the distance r between the second linear magnetic-field generating unit 10 and the capsule endoscope 2 shown in FIG. 8, of position calculation operations, such a characteristic that the strength of the second linear magnetic field output from the second linear magnetic-field generating unit 10 attenuates gradually as the second linear magnetic field is away from the second linear magnetic-field generating unit 10 is used. Specifically, since the position calculator 41 calculates the distance r based on a strength attenuation factor of the second linear magnetic field, the magnetic field strength near the second linear magnetic-field generating unit 10 needs to be ascertained. Therefore, at the time of position calculation at step S105, the position calculator 41 (and the orientation calculator 40 according to need) is input with the information relating to the control content from the magnetic-field strength controller 50, and performs position detection by using such information.

An advantage of the body-insertable apparatus system according to the first embodiment is explained next. The body-insertable apparatus system according to the first embodiment has an advantage in that the power consumption in the entire position detecting apparatus 3 can be reduced, by detecting the position of the capsule endoscope by using the generated magnetic field, and controlling the strength of the magnetic field used for position detection to a necessary and sufficient value.

In other words, in the body-insertable apparatus system according to the first embodiment, as shown in FIG. 11, the possible existence range is set as an area having a high possibility that the capsule endoscope 2 is present at a point in time ($=t_2$) when the position detection is performed, and the magnetic field is generated so as to cover the possible existence range. Therefore, the magnetic-field generating area can be considerably narrowed, as compared with a conventional case in which the magnetic field is generated so as to cover the whole subject 1, and the electric energy required for generation of the magnetic field can be reduced, thereby enabling realization of the body-insertable apparatus system having low power consumption.

In the body-insertable apparatus system according to the first embodiment, since the magnetic-field generating area is set narrower than in a conventional system, there is an advantage in that an influence on the peripheral equipment can be reduced than in the conventional system. In other words, by setting the magnetic-field generating area narrow, the strength of the magnetic field generated outside the subject 1 is also reduced, thereby enabling reduction of the influence on the electronic equipment positioned outside the subject 1.

Further, the body-insertable apparatus system according to the first embodiment calculates the spherical area 53, whose radius has a value obtained by multiplying the calculated moving speed v by elapsed time $\Delta t$, centering on the position of the capsule endoscope 2 detected at time instant $t_1$, as the possible existence range as shown in FIG. 11. By defining the possible existence range by the spherical area 53, a possible existence range having high reliability can be calculated.

Generally, the capsule endoscope 2 has a characteristic such that the moving speed changes corresponding to a transit area in the subject 1. Therefore, for example, when the possible existence range is uniformly defined relative to the position at time instant $t_1$, in the area such as the esophagus in which the capsule endoscope 2 passes at a high speed, there is a high probability that the capsule endoscope 2 is located at a position outside the possible existence range at time instant $t_2$, and hence reliable position detection cannot be performed. On the other hand, in the first embodiment, the moving speed is calculated based on the past detection results, and the possible existence range is set to a range reachable by the calculated moving speed. Accordingly, the problem when the possible existence range is uniformly defined does not occur, and hence the possible existence range having high reliability can be calculated. In other words, the body-insertable apparatus system according to the first embodiment has an advantage in that the power required for generating the magnetic field can be reduced, while maintaining the position detection accuracy.

A body-insertable apparatus system according to a second embodiment is explained next. The body-insertable apparatus system according to the second embodiment calculates the moving speed of the capsule endoscope 2 as a presupposition of the magnetic-field strength control by using a database in which a relationship between the position and the moving speed of the capsule endoscope 2 in the subject 1 is pre-recorded.

Figure 13:
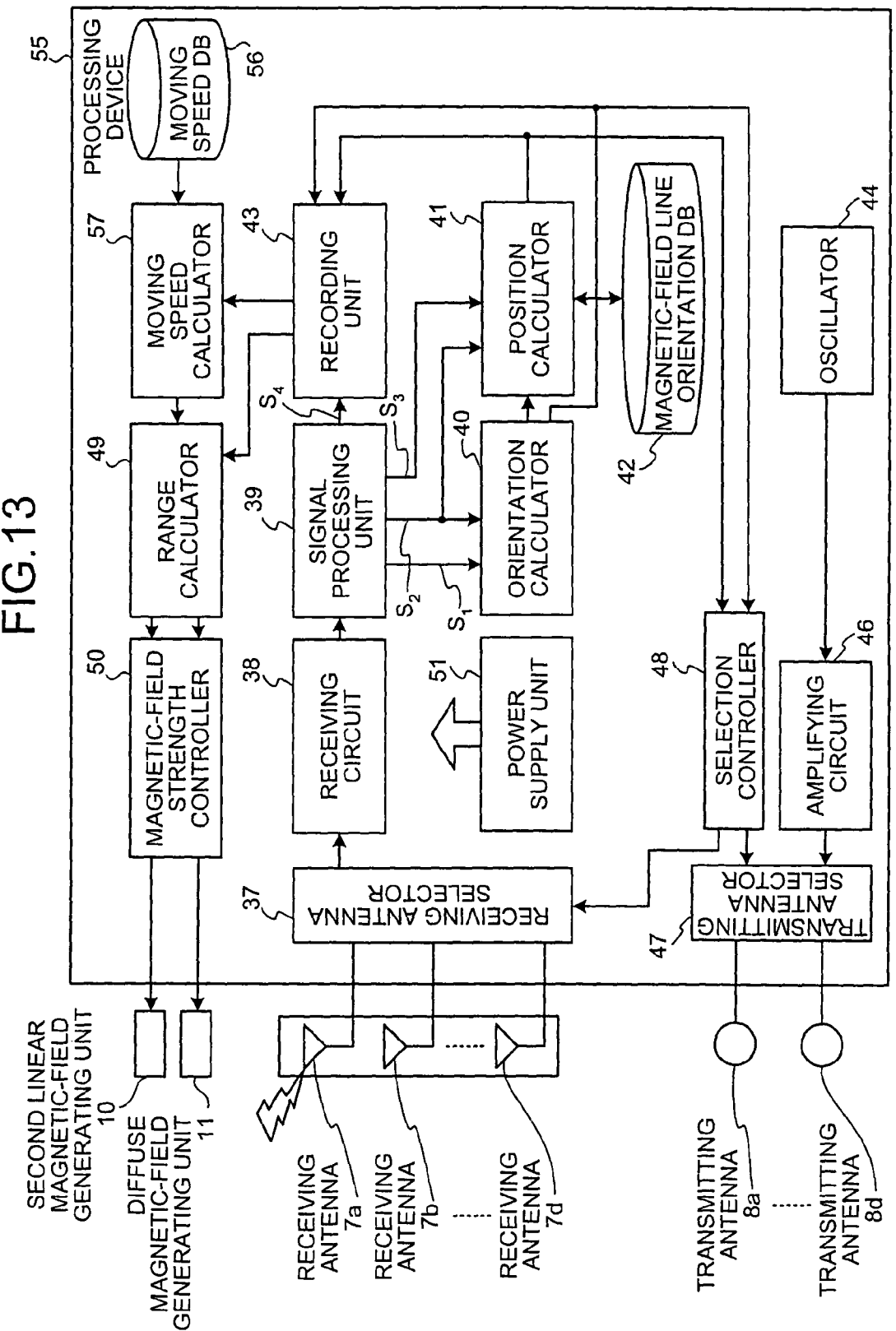
FIG. 13 is a schematic block diagram of a configuration of a processing device included in a body-insertable apparatus system according to a second embodiment.

FIG. 13 is a schematic block diagram of a configuration of a processing device 55 included in the body-insertable apparatus system according to the second embodiment. The body-insertable apparatus system according to the second embodiment basically has the same configuration as the body-insertable apparatus system according to the first embodiment, and includes the capsule endoscope 2, the display device 4, and the portable recording medium 5 as in the first embodiment, although not shown. The position detecting apparatus includes the receiving antennas 7a to 7d, the transmitting antennas 8a to 8d, the first linear magnetic-field generating unit 9, the second linear magnetic-field generating unit 10, and the diffuse magnetic-field generating unit 11 as in the first embodiment, other than the processing device 55 explained below. In the processing device 55, parts denoted by like names or reference numerals as in the processing device 12 in the first embodiment have like structures and functions as in the first embodiment, unless otherwise specified.

The processing device 55 included in the body-insertable apparatus system according to the second embodiment additionally includes a moving speed database 56 as shown in FIG. 13. The moving speed database 56 records information relating to the correspondence between the position and the moving speed of the capsule endoscope 2 in the subject 1, a moving speed calculator 57 calculates the moving speed of the capsule endoscope 2 at the second time instant based on the position of the capsule endoscope 2 at the first time instant and the information recorded in the moving speed database 56.

The moving speed of the capsule endoscope 2 does not keep a definite value in the subject 1 at all times, but normally changes due to the structure or the like of the digestive organs to be passed. For example, the capsule endoscope 2 moves at a high speed when passing through the esophagus, while the moving speed decreases when the capsule endoscope 2 passes through the small intestine. In the second embodiment, attention is given to the characteristic such that the moving speed of the capsule endoscope 2 changes depending on the position in the subject 1, and the moving speed is calculated by typifying correspondence between the positions in the subject and the moving speed beforehand, and preparing the typified correspondence as data.

Figure 14:
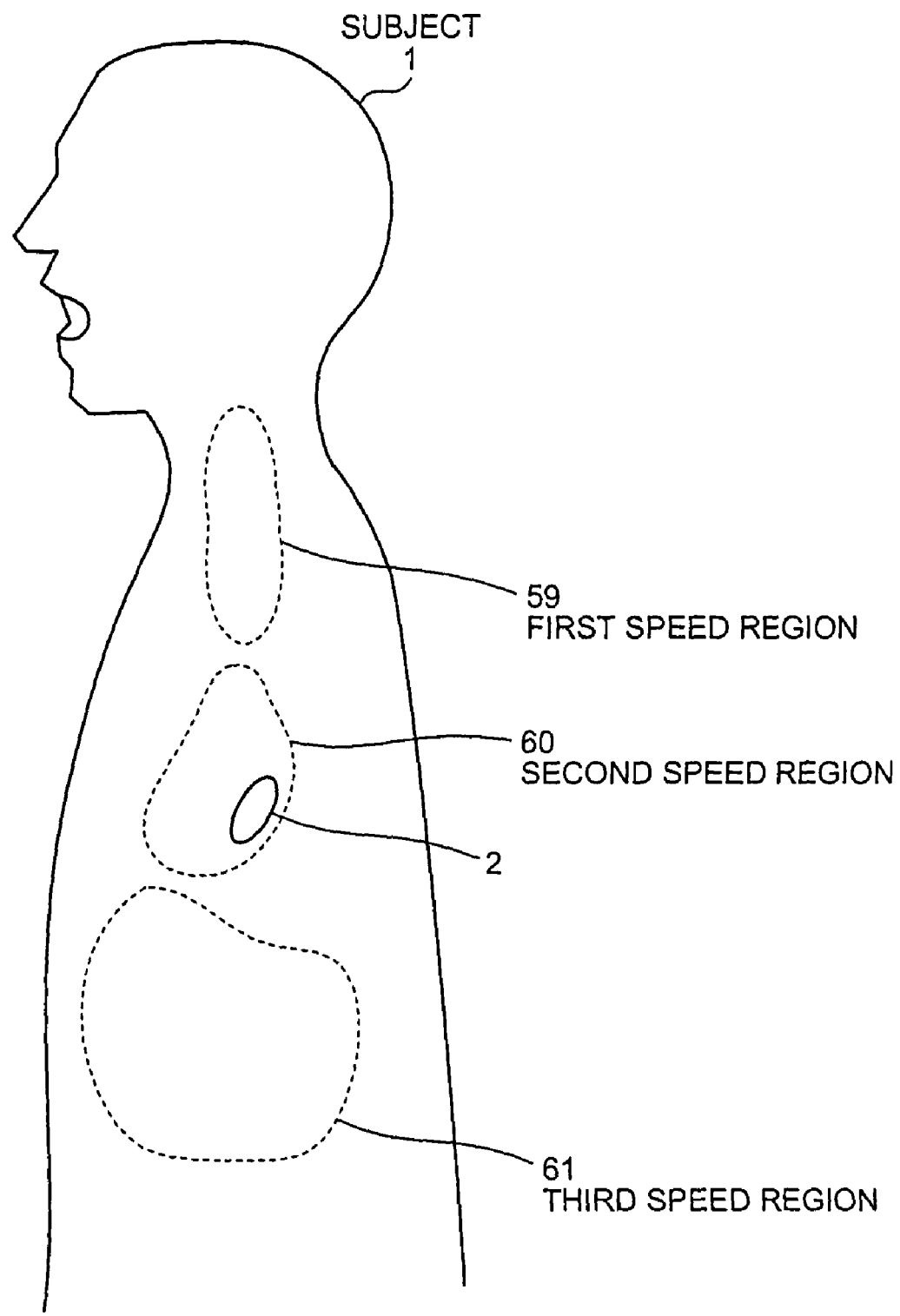
FIG. 14 is a schematic diagram of an example of a content of information stored in a moving speed database.

FIG. 14 is a schematic diagram of an example of a content of information recorded in the moving speed database 56. As shown in FIG. 14, in the moving speed database 56, the region through which the capsule endoscope 2 passes is roughly divided into three, as an example. Specifically, the moving speed database 56 stores positions of a first speed region 59 corresponding to the esophagus, a second speed region 60 corresponding to the stomach, and a third speed region 61 corresponding to the small intestine and the large intestine, and stores the maximum speed for each region.

On the other hand, the moving speed calculator 57 calculates the moving speed of the capsule endoscope 2 in the following manner. That is, the moving speed calculator 57 refers to the recording unit 43 first, to acquire the information relating to the position of the capsule endoscope 2 at the first time instant (time instant $t_1$). The moving speed calculator 57 then determines in which speed region the capsule endoscope 2 positions at the first time instant based on the acquired position of the capsule endoscope 2, to acquire the corresponding information relating to the moving speed. For example, in FIG. 14, the moving speed calculator 57 determines that the capsule endoscope 2 belongs to the second speed region 60, ascertains the speed stored as the one corresponding to the second speed range 60 in the moving speed database 56 as the moving speed of the capsule endoscope 2 at the second time instant (time instant $t_2$), and outputs the moving speed to the range calculator 49.

An advantage of the body-insertable apparatus system according to the second embodiment is explained. In the second embodiment, there is an advantage in that the moving speed is easily calculated, in addition to the advantage in the first embodiment. That is, in the second embodiment, the moving speed calculator 57 calculates the moving speed by inputting the corresponding information from the moving speed database 56 based on the detected position of the capsule endoscope 2 at the first time instant. Accordingly, in the second embodiment, arithmetic processing need not be performed at the time of calculating the moving speed, and the moving speed can be calculated quickly and easily.

A body-insertable apparatus system according to a third embodiment is explained next. The body-insertable apparatus system according to the third embodiment can calculate the possible existence range with higher reliability, by calculating not only the moving speed but also the moving direction at the time of calculating the possible existence range.

Figure 15:
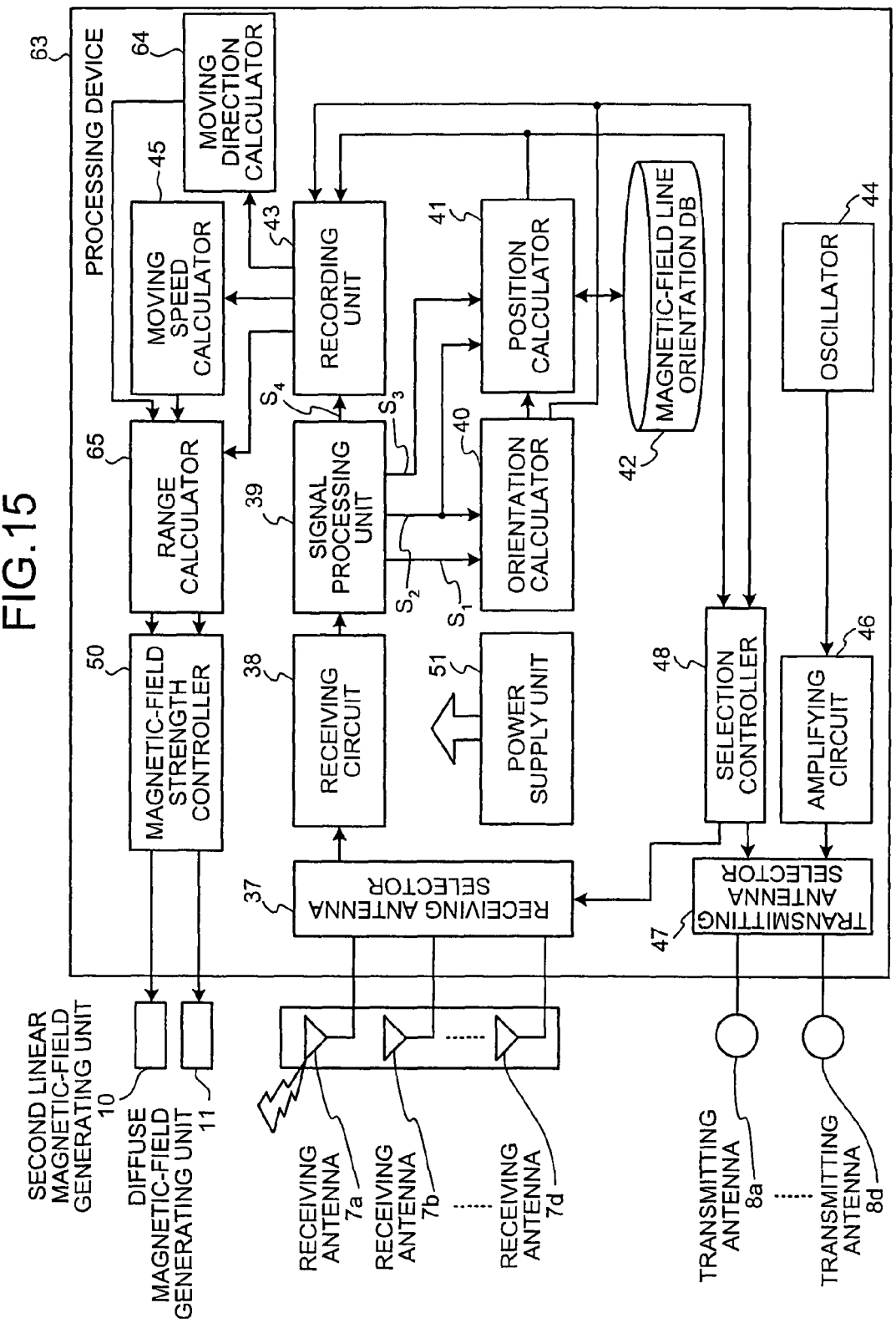
FIG. 15 is a schematic block diagram of a configuration of a processing device included in a body-insertable apparatus system according to a third embodiment.

FIG. 15 is a schematic block diagram of a configuration of a processing device 63 included in the body-insertable apparatus system according to the third embodiment. The body-insertable apparatus system according to the third embodiment includes the capsule endoscope 2, the display device 4, and the portable recording medium 5, although not shown, as in the second embodiment, and the position detecting apparatus includes the receiving antennas 7a to 7d and the like as in the first embodiment, other than the processing device 63 explained below. Parts denoted by like names or reference numerals as in the first and the second embodiments have like structures and functions as in the first and the second embodiments, unless otherwise specified.

As shown in FIG. 15, the processing device 63 further includes a moving direction calculator 64. The moving direction calculator 64 calculates the moving direction of the capsule endoscope 2 based on the orientation of the capsule endoscope 2 at the first time instant recorded in the recording unit 43, and outputs the calculated moving direction to a range calculator 65. The range calculator 65 calculates the possible existence range of the capsule endoscope 2 at the second time instant based on the position of the capsule endoscope 2 at the first time instant recorded in the recording unit 43, the moving speed calculated by the moving speed calculator 45, and the moving direction calculated by the moving direction calculator 64, corresponding to the structure in which the moving direction calculator 64 is newly provided.

Figure 16:
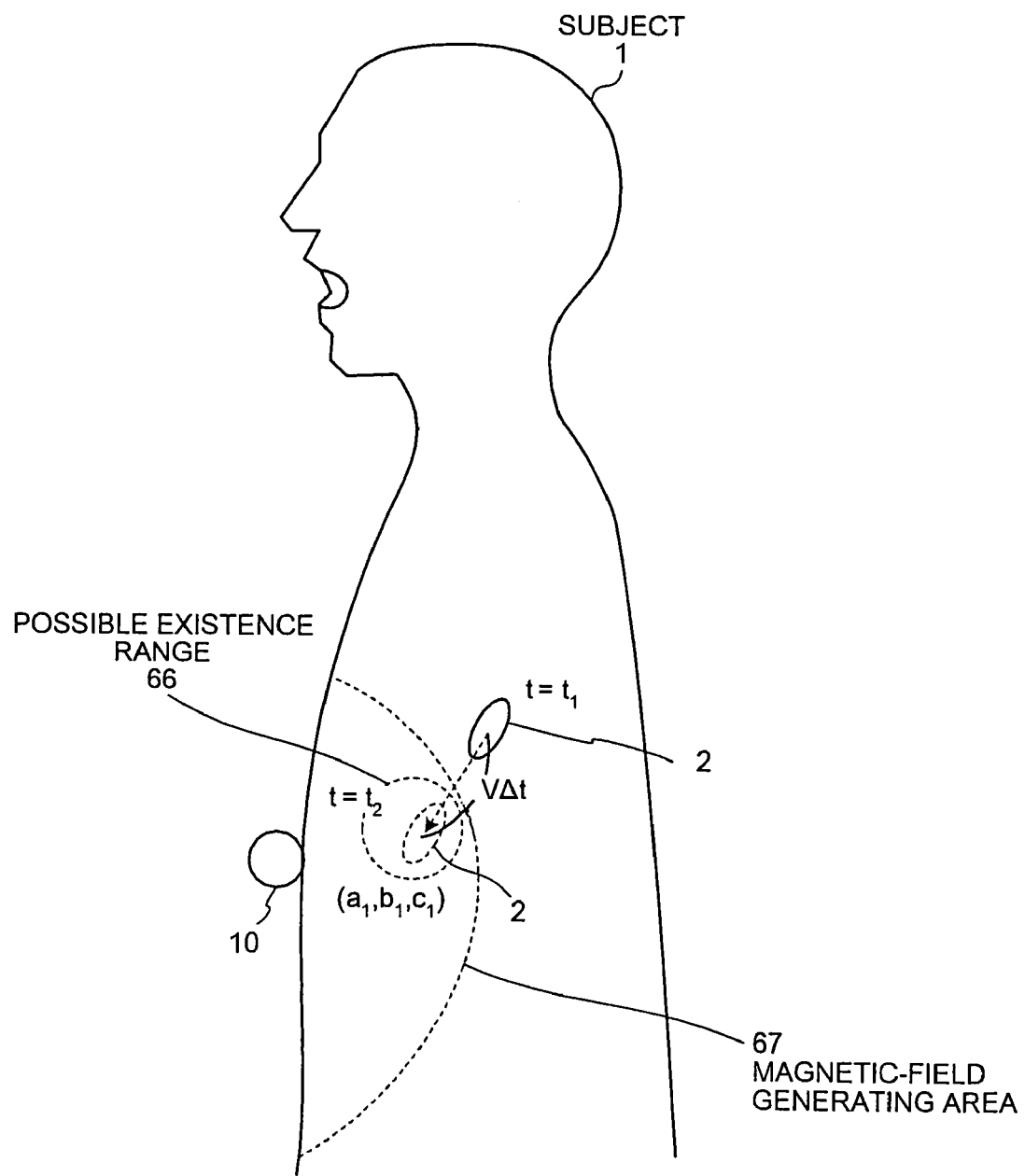
FIG. 16 is a schematic diagram for explaining a calculation mechanism of the possible existence range in the third embodiment.

FIG. 16 is a schematic diagram for explaining a calculation mechanism of the possible existence range in the third embodiment. It is assumed here that a moving speed v is calculated by the moving speed calculator 45 and moving directions $(a_1, b_1, c_1)$ are calculated by the moving direction calculator 64 with respect to the position of the capsule endoscope 2 at time instant $t_1$ (first time instant). On the other hand, since it is predicted that the capsule endoscope 2 at time instant $t_2$ (second time instant) moves to a point shifted by $v\Delta t$ in the moving direction as shown in FIG. 16, the range calculator 65 calculates a predetermined region including such a point as a possible existence range 66. The magnetic field controller 50 controls, for example, the second linear magnetic-field generating unit 10 so as to generate a magnetic-field forming range 67 including the possible existence range 66.

An advantage of the body-insertable apparatus system according to the third embodiment is explained. In the third embodiment, a configuration in which not only the moving speed but also the moving direction is used for the calculation of the possible existence range is adopted. Therefore, as compared to a case in which the moving direction is not particularly considered, and the possible existence range is calculated as the spherical area centering on the position of the capsule endoscope 2 at time instant $t_1$, the possible existence range can be narrowed. Accordingly, in the case of example shown in FIG. 16, the magnetic-field generating area can be narrowed as compared to a case in which the spherical area centering on the position of the capsule endoscope 2 at time instant $t_1$ is designated as the possible existence range, and hence there is an advantage in that the power consumption for generating the magnetic field required for the second linear magnetic-field generating unit 10 and the like can be further reduced.

A modification of the body-insertable apparatus system according to the third embodiment is explained. In the third embodiment, the moving direction calculator 64 calculates the moving direction based on the orientation of the capsule endoscope 2 at time instant $t_1$ recorded in the recording unit 43, however, in the modification, the moving direction is calculated based on the position of the capsule endoscope 2 at a plurality of past time instants.

Figure 17:
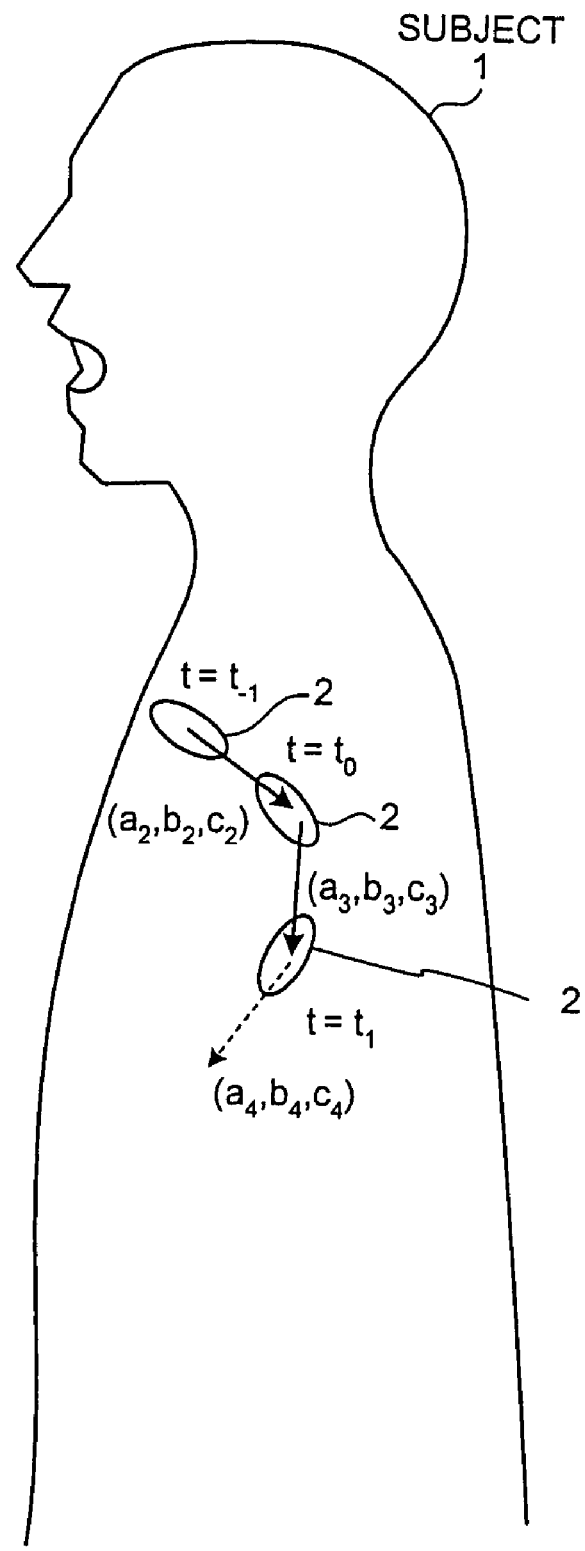
FIG. 17 is a schematic diagram for explaining a modification of the body-insertable apparatus system according to the third embodiment.

FIG. 17 is a schematic diagram for explaining the moving direction calculation mechanism in the modification. As shown in FIG. 17, in the modification, moving direction vectors $(a_4, b_4, c_4)$ from time instant $t_1$ to time instant $t_2$ are calculated based on moving direction vectors $(a_2, b_2, c_2)$ from time instant $t_{-1}$ to time instant to and moving direction vectors $(a_3, b_3, c_3)$ from time instant $t_0$ to time instant $t_1$, based on the position at the past time instants $t_{-1}, t_0,$ and $t_1$. Specifically, for example, the moving direction vector from time instant $t_1$ to time instant $t_2$ is calculated by calculating a mean value of the past moving direction vectors. It is also effective to calculate the moving direction according to such a method, and particularly, when it is applied to a position detecting apparatus, which does not have a function of calculating the orientation of the capsule endoscope 2, by adopting the configuration of the modification, the moving direction of the capsule endoscope 2 can be calculated even without having the function of calculating the orientation.

A body-insertable apparatus system according to a fourth embodiment is explained next. The body-insertable apparatus system according to the fourth embodiment has a function of detecting a position by using earth magnetism instead of the first linear magnetic field.

Figure 18:
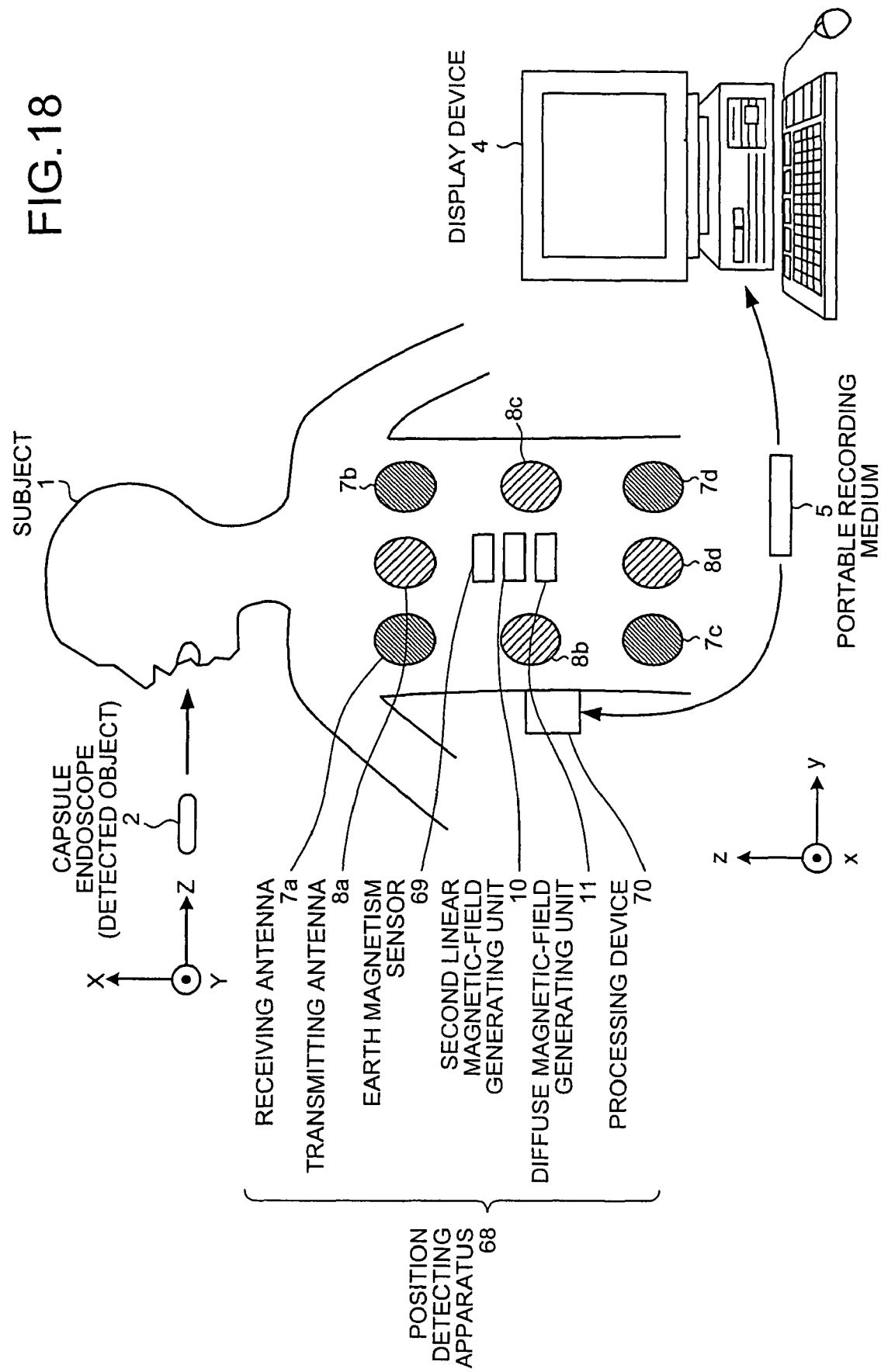
FIG. 18 is a schematic diagram of an overall configuration of a body-insertable apparatus system according to a fourth embodiment.

FIG. 18 is a schematic diagram of an overall configuration of the body-insertable apparatus system according to the fourth embodiment. As shown in FIG. 18, the body-insertable apparatus system according to the fourth embodiment includes the capsule endoscope 2, the display device 4, and the portable recording medium 5 as in the first to the third embodiment, while the configuration of a position detecting apparatus 68 is different. Specifically, the first linear magnetic-field generating unit 9 included in the position detecting apparatus in the first embodiment and the like is omitted, and an earth magnetism sensor 69 is newly included. A processing device 70 also has a configuration different from that of the first embodiment and the like.

The earth magnetism sensor 69 basically has the same configuration as that of the magnetic field sensor 16 included in the capsule endoscope 2. That is, the earth magnetism sensor 69 detects the strength of the magnetic field components in predetermined three axial directions in an area where it is arranged, and outputs an electric signal corresponding to the detected magnetic field strength. On the other hand, the earth magnetism sensor 69 is arranged on the body surface of the subject 1, which is different from the magnetic field sensor 16, and detects the strength of the magnetic field components respectively corresponding to the x-axis, y-axis, and z-axis directions in the reference coordinate axis fixed to the subject 1. In other words, the earth magnetism sensor 69 has a function of detecting the moving direction of the earth magnetism, and outputs the electric signal corresponding to the magnetic field strength detected for the x-axis direction, the y-axis direction, and the z-axis direction to the processing device 70.

Figure 19:
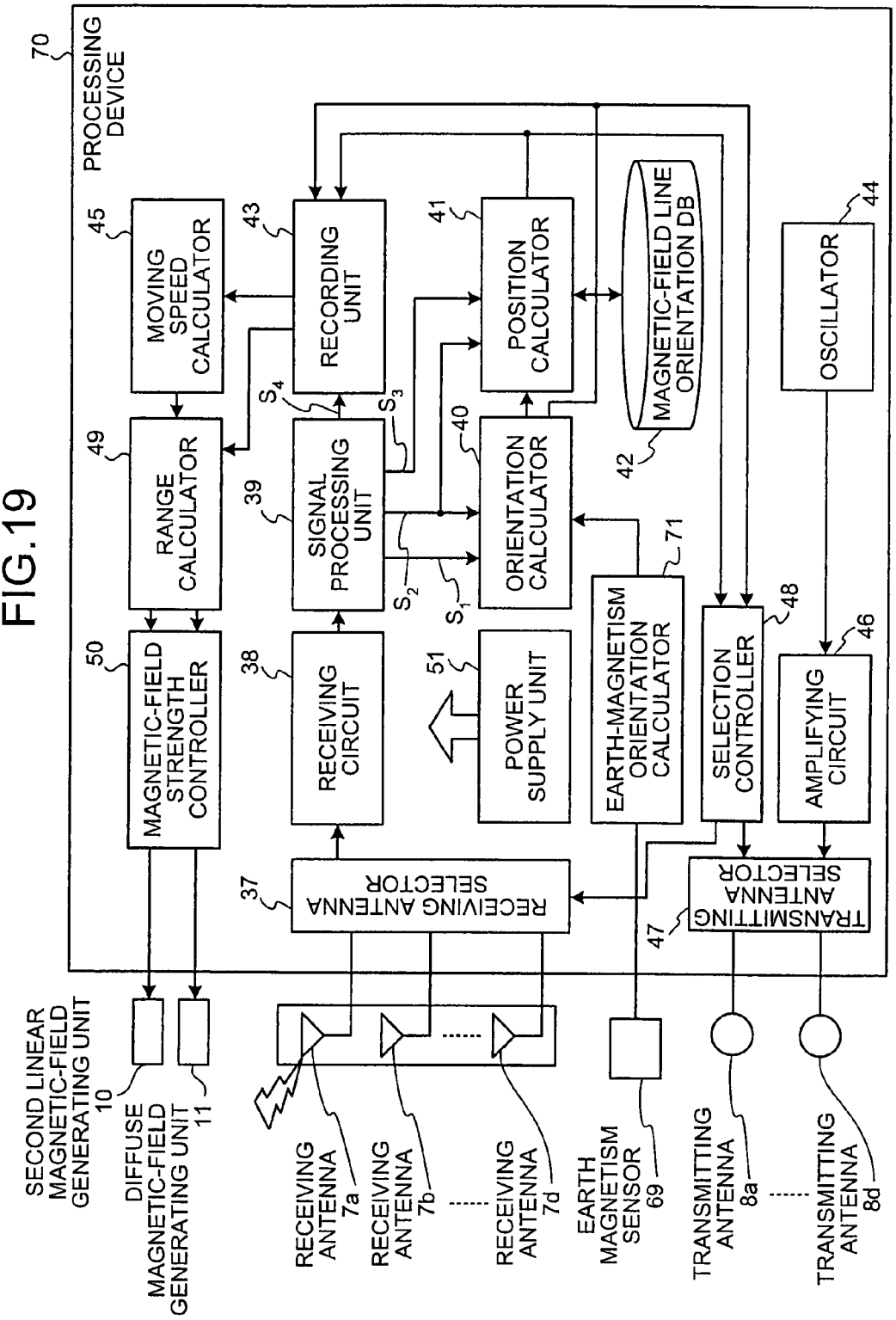
FIG. 19 is a schematic block diagram of a configuration of the processing device included in the body-insertable apparatus system.

The processing device 70 according to the fourth embodiment is explained next. FIG. 19 is a block diagram of a configuration of the processing device 70. As shown in FIG. 19, the processing device 70 basically has the same configuration as that of the processing device 12 in the first embodiment. On the other hand, the processing device 70 includes an earth-magnetism orientation calculator 71 that calculates the moving direction of the earth magnetism on the reference coordinate axis based on the electric signal input from the earth magnetism sensor 69, and outputs the calculation result to the orientation calculator 40.

There is a problem in calculation of the moving direction of the earth magnetism on the reference coordinate axis fixed to the subject 1, when the earth magnetism is used as the first linear magnetic field. That is, since the subject 1 can freely move while the capsule endoscope 2 is moving in the body, it is predicted that the position relationship between the reference coordinate axis fixed to the subject 1 and the earth magnetism changes with the movement of the subject 1. On the other hand, from a standpoint of calculating the position of the target coordinate axis relative to the reference coordinate axis, when the moving direction of the first linear magnetic field on the reference coordinate axis becomes unclear, there is a problem in that the correspondence between the reference coordinate axis and the target coordinate axis cannot be clarified relating to the moving direction of the first linear magnetic field.

Accordingly, in the fourth embodiment, the earth magnetism sensor 69 and the earth-magnetism orientation calculator 71 are provided for monitoring the moving direction of the earth magnetism, which will change on the reference coordinate axis due to movement or the like of the subject 1. In other words, the earth-magnetism orientation calculator 71 calculates the moving direction of the earth magnetism on the reference coordinate axis based on the detection result of the earth magnetism sensor 69, and outputs the calculation result to the orientation calculator 40. On the other hand, the orientation calculator 40 can calculate the correspondence between the reference coordinate axis and the target coordinate axis relating to the moving direction of the earth magnetism, by using the input moving direction of the earth magnetism to calculate orientation information together with the correspondence in the second linear magnetic field.

The moving directions of the earth magnetism and the second linear magnetic field generated by the second linear magnetic-field generating unit 10 can be parallel to each other, depending on the direction of the subject 1. In this case, the position relationship can be detected by also using data relating to the orientation of the target coordinate axis at the time immediately before and the origin. Further, to avoid that the moving directions of the earth magnetism and the second linear magnetic field become parallel to each other, it is also effective to have such a configuration that the extending direction of the coil 32 constituting the second linear magnetic-field generating unit 10 is not set to the y-axis direction in the reference coordinate axis, as shown in FIG. 4, but for example, set to the z-axis direction. Alternatively, the position detecting apparatus 68 may further include a sub-linear magnetic-field generating unit and a magnetic-field controller so that the moving directions of the earth magnetism and linear magnetic field which are generated in the region inside the subject 1 are not parallel to each other. The sub-linear magnetic-field generating unit generates a linear magnetic field different from the second linear magnetic field in moving direction (magnetic-field direction), in the region inside the subject 1 including the position of the capsule endoscope 2; the magnetic-field controller drives one of the second linear magnetic-field generating unit 10 and the sub-linear magnetic-field generating unit, based on a geometric relation between the linear magnetic field generated in the region inside the subject 1 and the earth magnetism. In this configuration, the magnetic-field controller determines whether the moving direction of the linear magnetic field generated by the second linear magnetic-field generating unit 10 and the moving direction of the earth magnetism calculated by the earth-magnetism orientation calculator 71 are parallel to each other or not, and drives one of the second linear magnetic-field generating unit 10 and the sub-linear magnetic-field generating unit based on the result of determination. Specifically, the magnetic-field controller causes the second linear magnetic-field generating unit 10 to generate a linear magnetic field if the moving direction of the linear magnetic field generated by the second linear magnetic-field generating unit 10 is not parallel to the moving direction of the earth magnetism. On the other hand, the magnetic-field controller causes the sub-linear magnetic-field generating unit, in place of the second linear magnetic-field generating unit 10, to generate a linear magnetic field if the moving direction of the linear magnetic field generated by the second linear magnetic-field generating unit 10 is parallel to the moving direction of the earth magnetism. As a result, the position detecting apparatus 68 can reliably generate the linear magnetic field different from the second linear magnetic field in moving direction (i.e., the linear magnetic field having a magnetic field component magnetic-field in a direction not parallel to the moving direction of the earth magnetism), in the region inside the subject 1 including the position of the capsule endoscope 2.

An advantage of a position detecting system according to the fourth embodiment is explained. The position detecting system according to the fourth embodiment has an advantage by using the earth magnetism in addition to the advantage of the first embodiment. That is, the mechanism for generating the first linear magnetic field can be omitted by adopting the configuration using the earth magnetism as the first linear magnetic field. Therefore, while the burden on the subject 1 at the time of introducing the capsule endoscope 2 can be reduced, the position of the target coordinate axis relative to the reference coordinate axis can be calculated. Since the earth magnetism sensor 69 can be formed by using an MI sensor or the like, the earth magnetism sensor 69 can have a small size, and the burden on the subject 1 does not increase by newly providing the earth magnetism sensor 69.

Further, there is a further advantage from a standpoint of reducing the power consumption, by adopting the configuration in which the earth magnetism is used as the first linear magnetic field. That is, when the first linear magnetic field is formed by using the coil or the like, the power consumption increases due to the electric current allowed to flow to the coil. However, such power consumption becomes unnecessary due to the earth magnetism, thereby enabling realization of a low power-consumption system.

Figure 20:
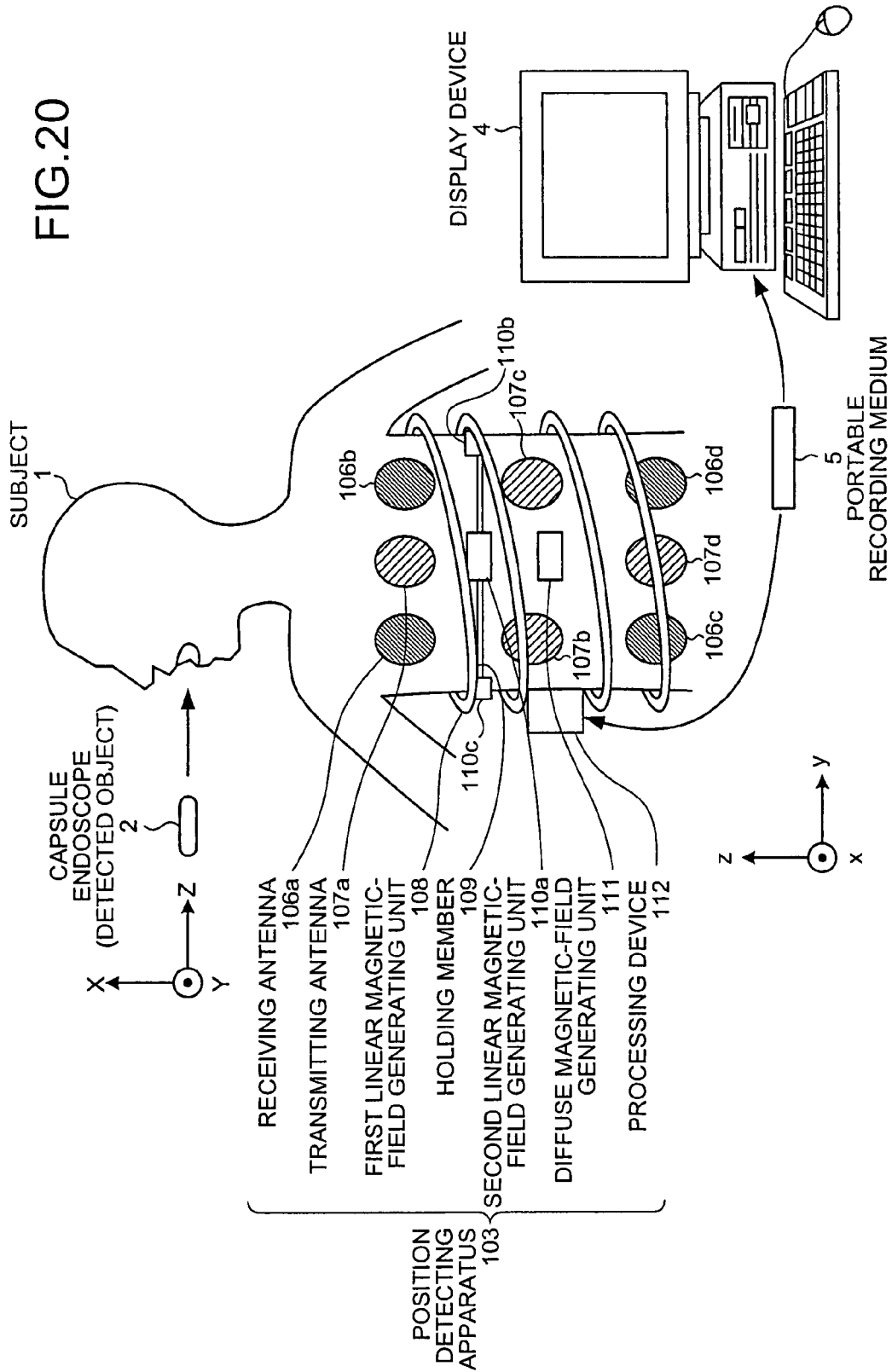
FIG. 20 is a schematic diagram of an overall configuration of a body-insertable apparatus system according to a fifth embodiment.

A body-insertable apparatus system according to a fifth embodiment is explained next. FIG. 20 is a schematic diagram of an overall configuration of the body-insertable apparatus system according to the fifth embodiment. In FIG. 20, since the capsule endoscope 2, the display device 4, and the portable recording medium 5 have the same configuration as those of the first embodiment, the explanation thereof is omitted. A different point from the first embodiment is the configuration of a position detecting apparatus 103.

The position detecting apparatus 103 is explained below. As shown in FIG. 20, the position detecting apparatus 103 includes receiving antennas 106a to 106d for receiving the radio signal transmitted from the capsule endoscope 2, transmitting antennas 107a to 107d for transmitting the radio signal for feeding power to the capsule endoscope 2, a first linear magnetic-field generating unit 108 that generates the first linear magnetic field, second linear magnetic-field generating units 110a to 110d that generate the second linear magnetic field, which are held by a holding member 109, a diffuse magnetic-field generating unit 111 that generates the diffuse magnetic field, and a processing device 112 that performs predetermined processing to the radio signal and the like received via the receiving antennas 106a to 106d.

Since the receiving antennas 106a to 106d, the transmitting antennas 107a to 107d, and the first linear magnetic-field generating unit 108 have the same configuration as those of the receiving antennas 7a to 7d, the transmitting antennas 8a to 8d, and the first linear magnetic-field generating unit 9 in the first embodiment, the explanation thereof is omitted.

The second linear magnetic-field generating units 110a to 110d are explained, which generate the second linear magnetic field functioning as an example of the position detecting magnetic field in the present invention, and function as an example of the magnetic field generator in the present invention. The second linear magnetic-field generating units 110a to 110d generate the second linear magnetic field, which is a linear magnetic field moving in a different direction from that of the first linear magnetic field, and has position dependency regarding the strength.

Figure 21:
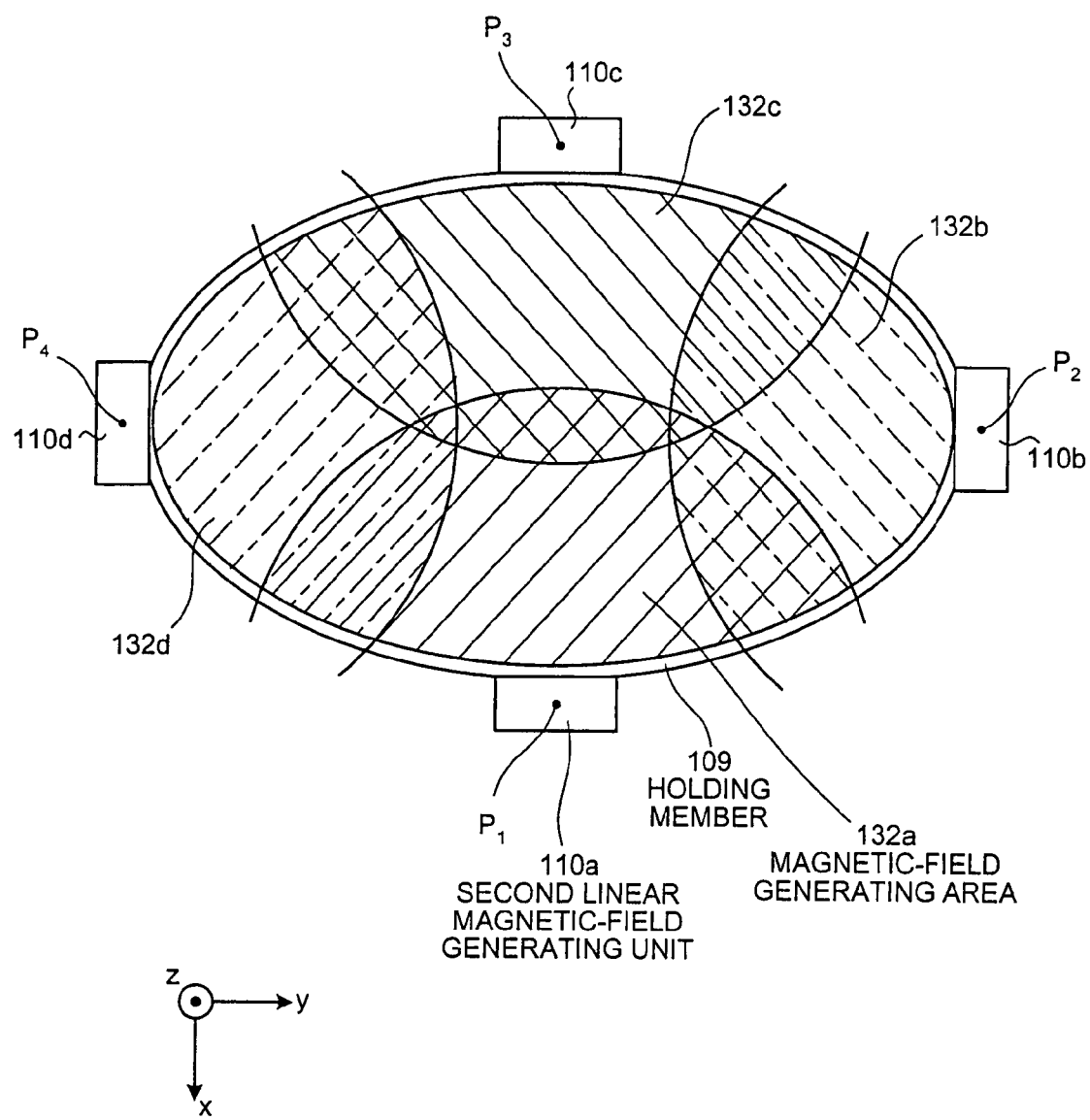
FIG. 21 is a schematic diagram of an arrangement pattern of the second linear magnetic field generating unit included in the position detecting apparatus.

FIG. 21 is a schematic diagram of position relationship between the second linear magnetic-field generating units 110a to 110d arranged in a plurality of numbers and the holding member 109 that fixes the second linear magnetic-field generating units 110a to 110d relative to the subject 1 in the fifth embodiment. As shown in FIG. 21, the respective second linear magnetic-field generating units 110a to 110d are arranged at points $P_1$ to $P_4$, which are points at the ends in the x-axis direction and the y-axis direction on the holding member 109 formed so as to cover the body of the subject 1, to generate the second linear magnetic field corresponding to magnetic-field generating areas 132a to 132d. The "magnetic-field generating area" stands for an area in which the magnetic field having strength usable at the time of position detection, and in the fifth embodiment, a magnetic field having the strength detectable by the magnetic field sensor 16 included in the capsule endoscope 2. As shown in FIG. 21, the respective magnetic-field generating areas 132a to 132d are formed so as to include a part of the area where the capsule endoscope 2 as the detected object can be positioned, that is, a part of the whole area of the subject 1, while an area obtained by adding respective magnetic-field generating areas includes the whole area where the capsule endoscope 2 can be positioned.

Figure 22:
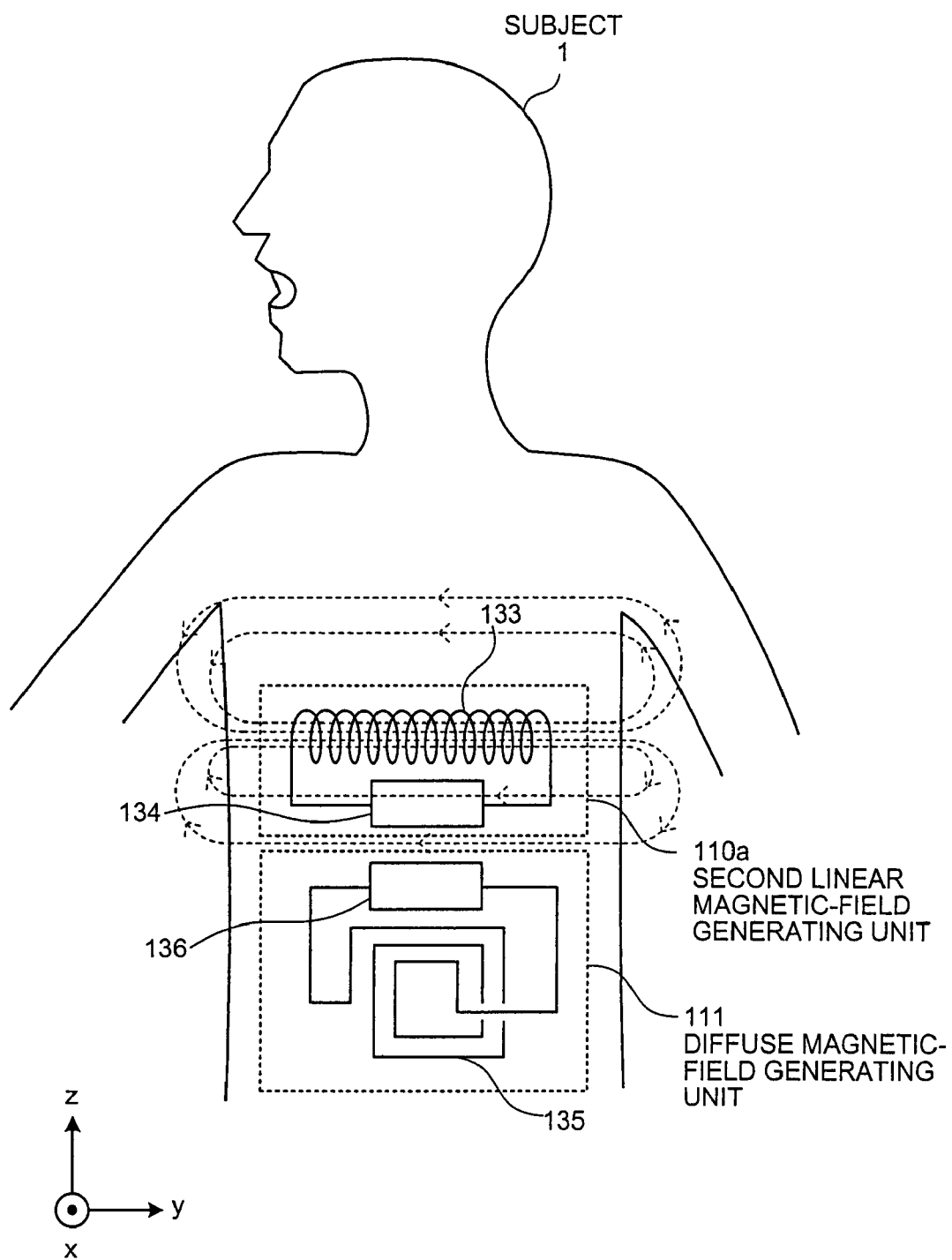
FIG. 22 is a schematic diagram of a configuration of the second linear magnetic field generating unit and the diffuse magnetic-field generating unit included in the position detecting apparatus, and a mode of the second linear magnetic field generated by the second linear magnetic field generating unit.

FIG. 22 is a schematic diagram of a configuration of the second linear magnetic-field generating unit 110a and the diffuse magnetic-field generating unit 111, and a mode of the second linear magnetic field generated by the second linear magnetic-field generating unit 110a. As shown in FIG. 22, the second linear magnetic-field generating unit 110a includes a coil 133 extending in the y-axis direction in the reference coordinate axis, and is formed so that a coil section becomes parallel to an xz-plane, and a current source 134 for supplying electric current to the coil 133. Therefore, the second linear magnetic field formed by the coil 133 becomes a linear magnetic field at least in the subject 1, as shown in FIG. 22, and has a characteristic such that the strength gradually attenuates as the second linear magnetic field is away from the coil 133, that is, the position dependency regarding the strength. Only the second linear magnetic-field generating unit 110a is shown in FIG. 22, however, the second linear magnetic-field generating units 110b to 110d have the same configuration as that of the second linear magnetic-field generating unit 110a, and generate the same linear magnetic field as that of the second linear magnetic-field generating unit 110a.

The diffuse magnetic-field generating unit 111 is explained next. The diffuse magnetic-field generating unit 111 generates the diffuse magnetic field having the position dependency regarding not only the magnetic field strength but also the magnetic field direction. Specifically, the diffuse magnetic-field generating unit 111 includes, as shown in FIG. 22, a coil 135 and a current source 136 for feeding power to the coil 135.

Figure 23:
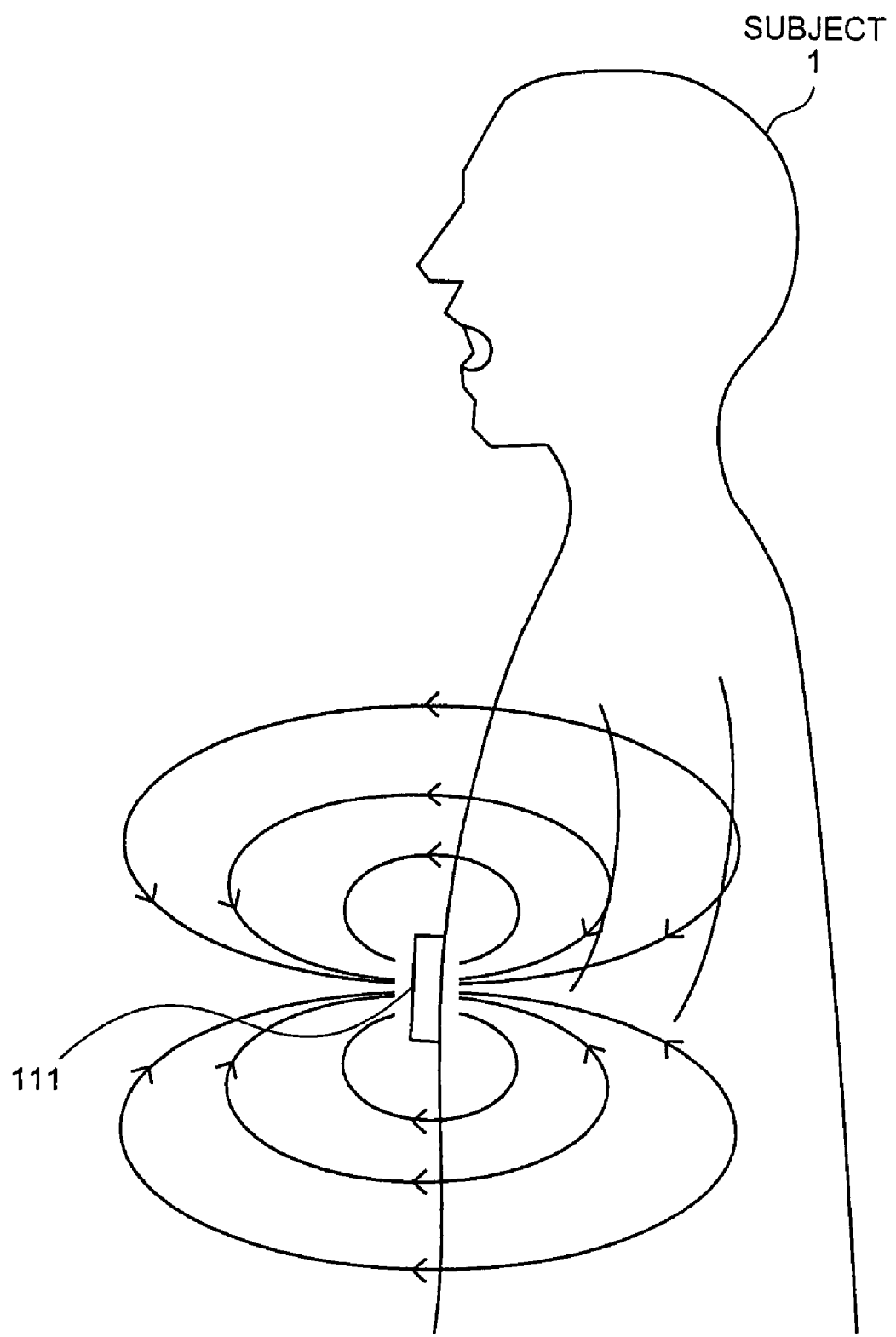
FIG. 23 is a schematic diagram of a mode of the diffuse magnetic field generated by the diffuse magnetic-field generating unit.

FIG. 23 is a schematic diagram of a mode of the diffuse magnetic field generated by the diffuse magnetic-field generating unit 111. As shown in FIG. 23, the coil 135 included in the diffuse magnetic-field generating unit 111 is formed in a coiled shape on the surface of the subject 1, and the diffuse magnetic field generated by the diffuse magnetic-field generating unit 111 is, as shown in FIG. 23, such that the magnetic-field line radially diffuses once and enters in the coil 135 again, in the magnetic field formed by the coil 135 (not shown in FIG. 23).

In the fifth embodiment, it is assumed that the first linear magnetic-field generating unit 108, the second linear magnetic-field generating unit 110, and the diffuse magnetic-field generating unit 111 generate the magnetic field at respectively different time instants. In other words, in the fifth embodiment, the first linear magnetic-field generating unit 108 and the like do not generate the magnetic field simultaneously, but generate the magnetic field according to a predetermined order, and the magnetic field sensor 16 included in the capsule endoscope 2 detects the first linear magnetic field, the second linear magnetic field, and the diffuse magnetic field separately and independently.

Figure 24:
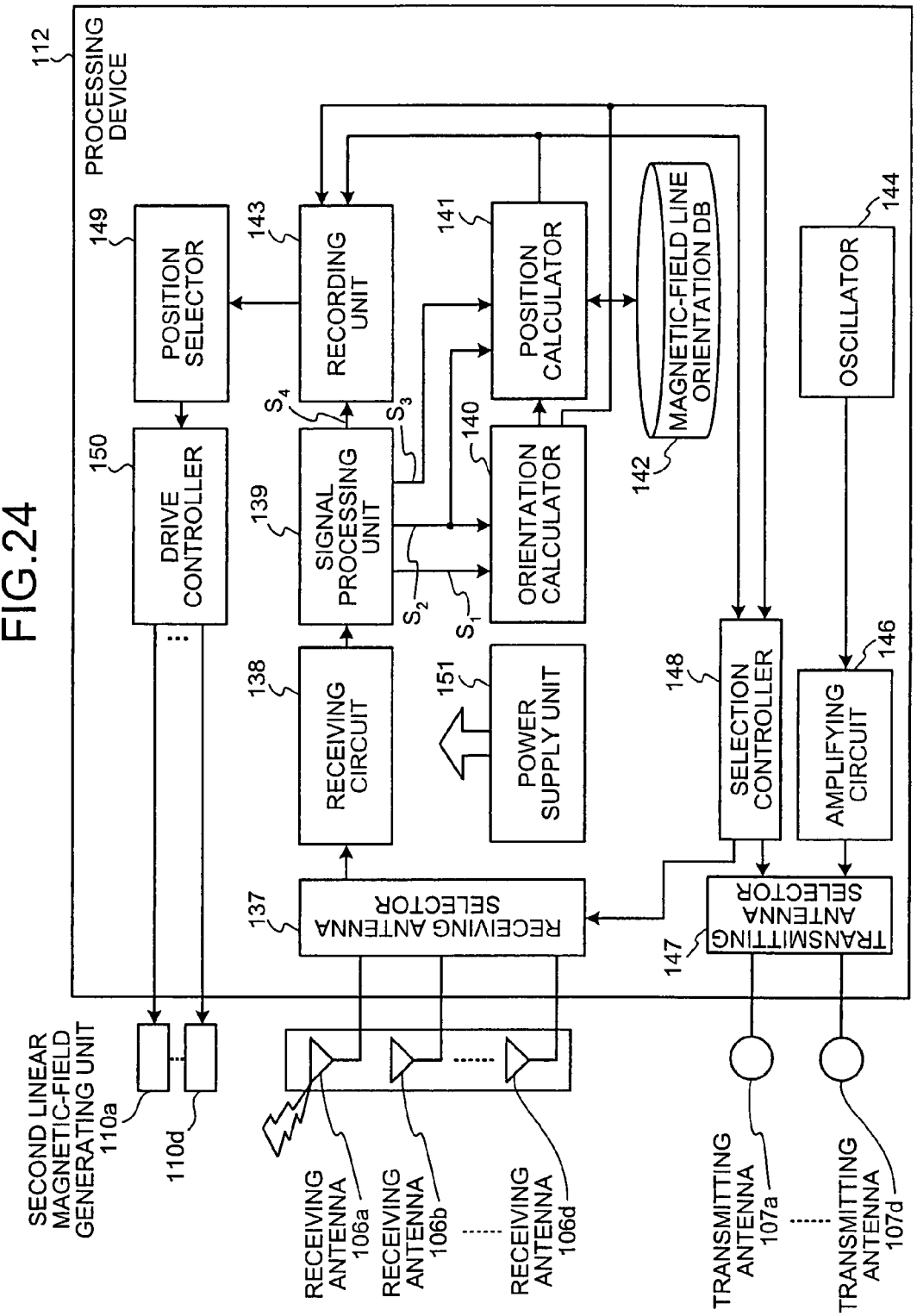
FIG. 24 is a schematic block diagram of a configuration of the processing device included in the position detecting apparatus.

The configuration of the processing device 112 is explained next. FIG. 24 is a schematic block diagram of a configuration of the processing device 112. The processing device 112 has a function of performing receiving processing of the radio signal transmitted by the capsule endoscope 2, and has a receiving antenna selector 137 that selects any one of the receiving antennas 106a to 106d, a receiving circuit 138 that performs demodulation or the like with respect to the radio signal received via the selected receiving antenna to extract an original signal included in the radio signal, and a signal processing unit 139 that reconstructs an image signal and the like by processing the extracted original signal, corresponding to the function.

Specifically, the signal processing unit 139 has a function of reconstructing magnetic field signals $S_1$ to $S_3$ and an image signal $S_4$ based on the extracted original signal, and outputting these signals to an appropriate component respectively. The magnetic field signals $S_1$ to $S_3$ correspond to the first linear magnetic field, the second magnetic field, and the diffusion magnetic field, respectively, detected by the magnetic field sensor 16. The image signal $S_4$ corresponds to the intra-subject image acquired by the intra-subject information acquiring unit 14. The specific mode of the magnetic field signals $S_1$ to $S_3$ is expressed by a direction vector corresponding to the detected magnetic field strength in the target coordinate axis fixed relative to the capsule endoscope 2, and includes information of the moving direction of the magnetic field and the magnetic field strength in the target coordinate axis. The image signal $S_4$ is output to a recording unit 143. The recording unit 143 outputs input data to the portable recording medium 5, and has a function of recording results of position detection and the like as well as the image signal $S_4$ on the portable recording medium 5.

The processing device 112 also has a function of detecting the position of the capsule endoscope 2 in the subject 1 based on the magnetic field strength or the like detected by the capsule endoscope 2, and a function of detecting an orientation of the target coordinate axis fixed to the capsule endoscope 2 relative to the reference coordinate axis fixed to the subject 1. Specifically, the processing device 112 includes an orientation calculator 140 that calculates the orientation of the target coordinate axis relative to the reference coordinate axis based on the magnetic field signals $S_1$ and $S_2$ corresponding to the detected strength of the first linear magnetic field and the second linear magnetic field, of the signals transmitted by the capsule endoscope 2 and output by the signal processing unit 139, a position calculator 141 that calculates the position of the capsule endoscope 2 by using the magnetic field signal $S_3$ corresponding to the detected strength of the diffuse magnetic field, the magnetic field signal $S_2$, and a calculation result of the orientation calculator 140, and the magnetic-field line orientation database 142 in which the correspondence between the moving direction and the position of the magnetic-field line constituting the diffuse magnetic field is recorded at the time of calculating the position by the position calculator 141. Orientation calculation and position calculation by these components will be explained later in detail.

The processing device 112 has a function of wirelessly transmitting driving power to the capsule endoscope 2, and includes an oscillator 144 that specifies the frequency of the transmitted radio signal, an amplifying circuit 146 that amplifies the strength of the radio signal output from the oscillator 144, and a transmitting antenna selector 147 that selects a transmitting antenna used for transmission of the radio signal. The radio signal is received by the receiving antenna 28 included in the capsule endoscope 2, and functions as the driving power of the capsule endoscope 2.

The processing device 112 includes a selection controller 148 that controls an antenna selection mode by the receiving antenna selector 137 and the transmitting antenna selector 147. The selection controller 148 has a function of selecting the transmitting antenna 107 and the receiving antenna 106 most suitable for the transfer with respect to the capsule endoscope 2, based on the orientation and position of the capsule endoscope 2, respectively, calculated by the orientation calculator 140 and the position calculator 141.

The processing device 112 also has a function of selecting any one of the second linear magnetic-field generating units 110a to 110d arranged in a plurality of numbers based on the position of the capsule endoscope 2, and controlling the selected second linear magnetic-field generating unit to generate the second linear magnetic field. Specifically, the processing device 112 includes a position selector 149 that selects an appropriate position from the positions of the second linear magnetic-field generating units 110a to 110d functioning as the magnetic-field generating area, a drive controller 150 that controls the second linear magnetic-field generating unit 110 corresponding to the position selected by the position selector 149, and a power supply unit 151 that supplies driving power to respective components in the processing device 112.

The position selector 149 selects a position at which the magnetic-field generating area that generates the position detecting magnetic field at the time of position detection at the second time instant when a predetermined time has passed since the first time instant should be present. In the fifth embodiment, the configuration including the second linear magnetic-field generating units 110a to 110d is adopted as an example of the magnetic-field generator in the claims, and the position selector 149 selects the position at which the second linear magnetic-field generating unit 110 that generates the second linear magnetic field at the second time instant should be present, from positions $P_1$ to $P_4$ where the second linear magnetic-field generating units 110a to 110d are arranged.

Specifically, the position selector 149 ascertains the positions $P_1$ to $P_4$ of the second linear magnetic-field generating units 110a to 110d and the range of the magnetic-field generating areas 132a to 132d beforehand. The position selector 149 then selects the most appropriate position from the positions $P_1$ to $P_4$ as the position of the magnetic-field generating area for generating the second linear magnetic field at the second time instant, and outputs information of the selected position to the drive controller 150.

The drive controller 150 has a function of driving the second linear magnetic-field generating unit 110 corresponding to the position selected by the position selector 149. Specifically, drive controller 150 has a function of controlling the drive of the current source 134 included respectively in the second linear magnetic-field generating units 110a to 110d, and ascertaining the correspondence between the positions $P_1$ to $P_4$ and the second linear magnetic-field generating units 110a to 110d beforehand. Based on such functions, the drive controller 150 controls the second linear magnetic-field generating unit 110 corresponding to the information of the selected position output from the position selector 149 to form a predetermined magnetic-field generating area 132, and controls the second linear magnetic-field generating units 110, which do not correspond to the selected position to suspend magnetic field generation.

An operation of the body-insertable apparatus system according to the fifth embodiment is explained next. A position detection mechanism for detecting the position of the capsule endoscope 2 as the detected object is explained below, taking an example in which the second linear magnetic-field generating unit 110a is selected from the second linear magnetic-field generating units 110a to 110d. Thereafter, a selection mechanism for selecting the optimum second linear magnetic-field generating unit from the second linear magnetic-field generating units 110a to 110d used for position detection and the like is explained.

Position detection of the capsule endoscope 2 performed by the position detecting apparatus 103 is explained first. The body-insertable apparatus system according to the fifth embodiment has a configuration such that position relationship is calculated between the reference coordinate axis fixed to the subject 1 and the target coordinate axis fixed to the capsule endoscope 2. Specifically, the orientation of the target coordinate axis relative to the reference coordinate axis is calculated, and the position of the origin of the target coordinate axis on the reference coordinate axis, that is, the position of the capsule endoscope 2 inside the subject 1 is then calculated by using the calculated orientation. Therefore, the orientation calculation mechanism is first explained below, and the position calculation mechanism using the calculated orientation is explained next. However, of course, an application of the present invention is not limited to the system having the position detection mechanism.

The orientation calculation mechanism performed by the orientation calculator 140 is explained. Since the orientation calculation mechanism is the same as the one performed by the orientation calculator 40 explained with reference to FIG. 7, FIG. 7 is referred for the explanation. The capsule endoscope 2 is rotating by a predetermined angle, designating the moving direction as an axis, while moving along the passage route in the subject 1. Accordingly, the target coordinate axis fixed to the capsule endoscope 2 generates a deviation of the orientation as shown in FIG. 7, relative to the reference coordinate axis fixed to the subject 1.

On the other hand, the first linear magnetic-field generating unit 108 and the second linear magnetic-field generating unit 110a are fixed, respectively, relative to the subject 1. Therefore, the first and the second linear magnetic fields generated by the first linear magnetic-field generating unit 108 and the second linear magnetic-field generating unit 110a travel in a fixed direction relative to the reference coordinate axis, more specifically, the first linear magnetic field travels in the z-axis direction, and the second linear magnetic field at the time of using the second linear magnetic-field generating unit 110a travels in the y-axis direction in the reference coordinate axis.

Orientation calculation in the fifth embodiment is performed by using the first linear magnetic field and the second linear magnetic field. Specifically, the moving direction of the first linear magnetic field and the second linear magnetic field supplied in a time sharing manner is detected by the magnetic field sensor 16 included in the capsule endoscope 2. The magnetic field sensor 16 is configured so as to detect the magnetic field components in the X-axis direction, the Y-axis direction, and the Z-axis direction in the target coordinate axis, and information of the moving direction of the detected first and second linear magnetic fields in the target coordinate axis is transmitted to the position detecting apparatus 103 via the radio transmitting unit 19.

The radio signal transmitted by the capsule endoscope 2 is output as magnetic field signals $S_1$ and $S_2$ through the processing by the signal processing unit 139 and the like. For example, in the example shown in FIG. 7, the magnetic field signal $S_1$ includes information of a coordinate $(X_1, Y_1, Z_1)$ as the moving direction of the first linear magnetic field, and the magnetic field signal $S_2$ includes information of a coordinate $(X_2, Y_2, Z_2)$ as the moving direction of the second linear magnetic field. On the other hand, the orientation calculator 140 calculates the orientation of the target coordinate axis relative to the reference coordinate axis, upon reception of inputs of these magnetic field signals $S_1$ and $S_2$. Specifically, the orientation calculator 140 ascertains that a coordinate $(X_3, Y_3, Z_3)$ in which a value of an inner product with respect to both $(X_1, Y_1, Z_1)$ and $(X_2, Y_2, Z_2)$ in the target coordinate axis becomes zero corresponds to the direction of the z-axis in the reference coordinate axis. The orientation calculator 140 then performs predetermined coordinate conversion processing based on the above correspondence, to calculate the coordinate in the reference coordinate axis of the X-axis, the Y-axis, and the Z-axis in the target coordinate axis, and outputs such a coordinate as the orientation information.

The position calculation mechanism of the capsule endoscope 2 by the position calculator 141 using the calculated orientation is explained next. The position calculator 141 has a configuration such that magnetic field signals $S_2$ and $S_3$ are input from the signal processing unit 139, the orientation information is input from the orientation calculator 140, and information stored in the magnetic-field line orientation database 142 is input. The position calculator 141 calculates the position of the capsule endoscope 2 in the following manner, based on these pieces of input information.

Figure 25:
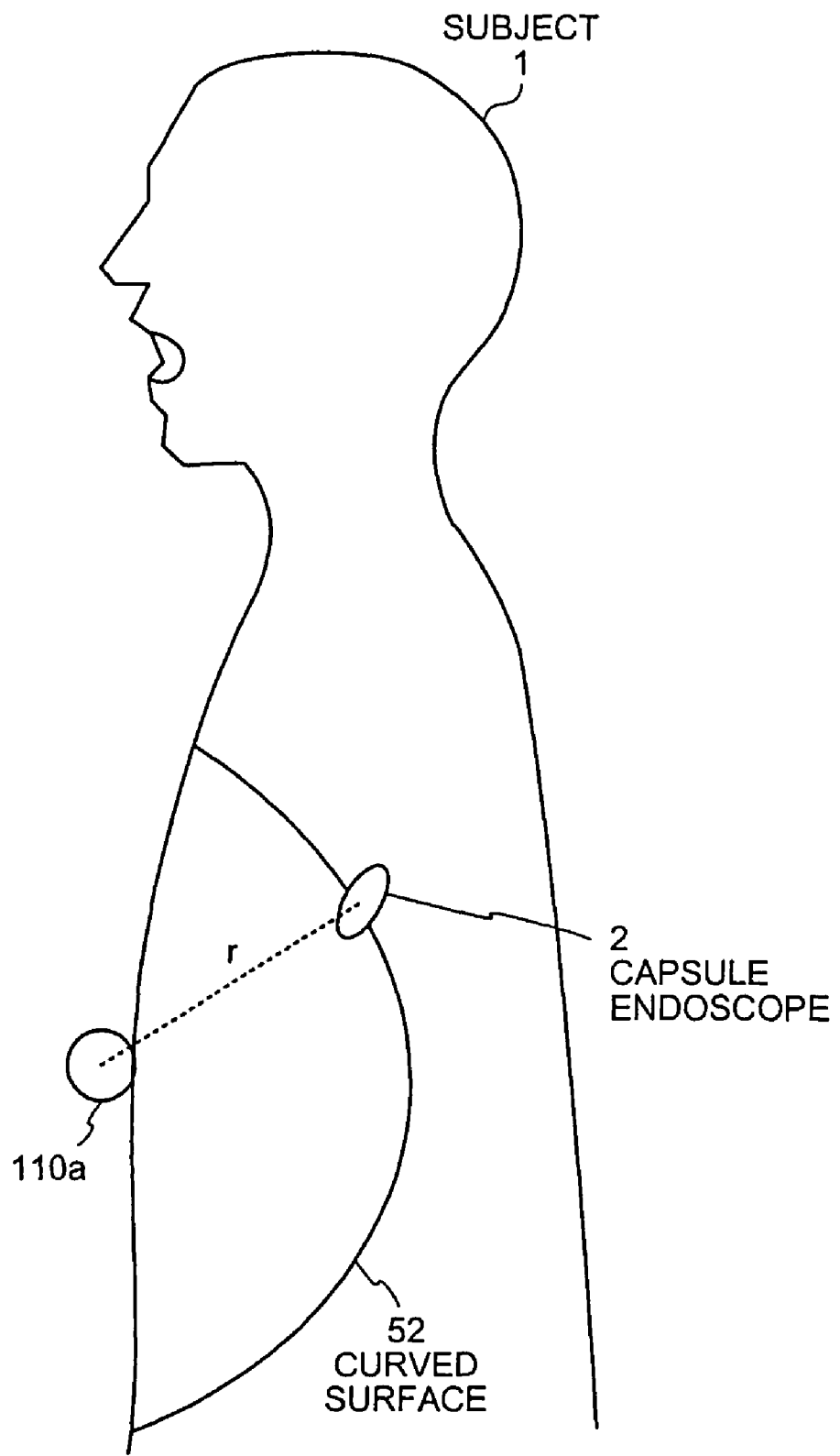
FIG. 25 is a schematic diagram of a use mode of the second linear magnetic field at the time of position calculation.

At first, the position calculator 141 calculates the distance between the second linear magnetic-field generating unit 110a and the capsule endoscope 2 by using the magnetic field signal $S_2$. The magnetic field signal $S_2$ corresponds to the detection result of the second linear magnetic field in the area where the capsule endoscope 2 is present. The second linear magnetic field has a such characteristic that the strength thereof gradually attenuates as the second linear magnetic field is away from the second linear magnetic-field generating unit 110a, corresponding to the second linear magnetic-field generating unit 110a being arranged outside of the subject 1. By using such a characteristic, the position calculator 141 compares the strength of the second linear magnetic field near the second linear magnetic-field generating unit 110a (obtained from a current value of the current allowed to flow to the second linear magnetic-field generating unit 110a) with the strength of the second linear magnetic field in the area where the capsule endoscope 2 is present obtained from the magnetic field signal $S_2$, to calculate a distance r between the second linear magnetic-field generating unit 110a and the capsule endoscope 2. As a result of calculation of the distance r, as shown in FIG. 25, it becomes obvious that the capsule endoscope 2 is positioned on a curved surface 52, which is an aggregate of points away from the second linear magnetic-field generating unit 110a by the distance r.

Figure 26:
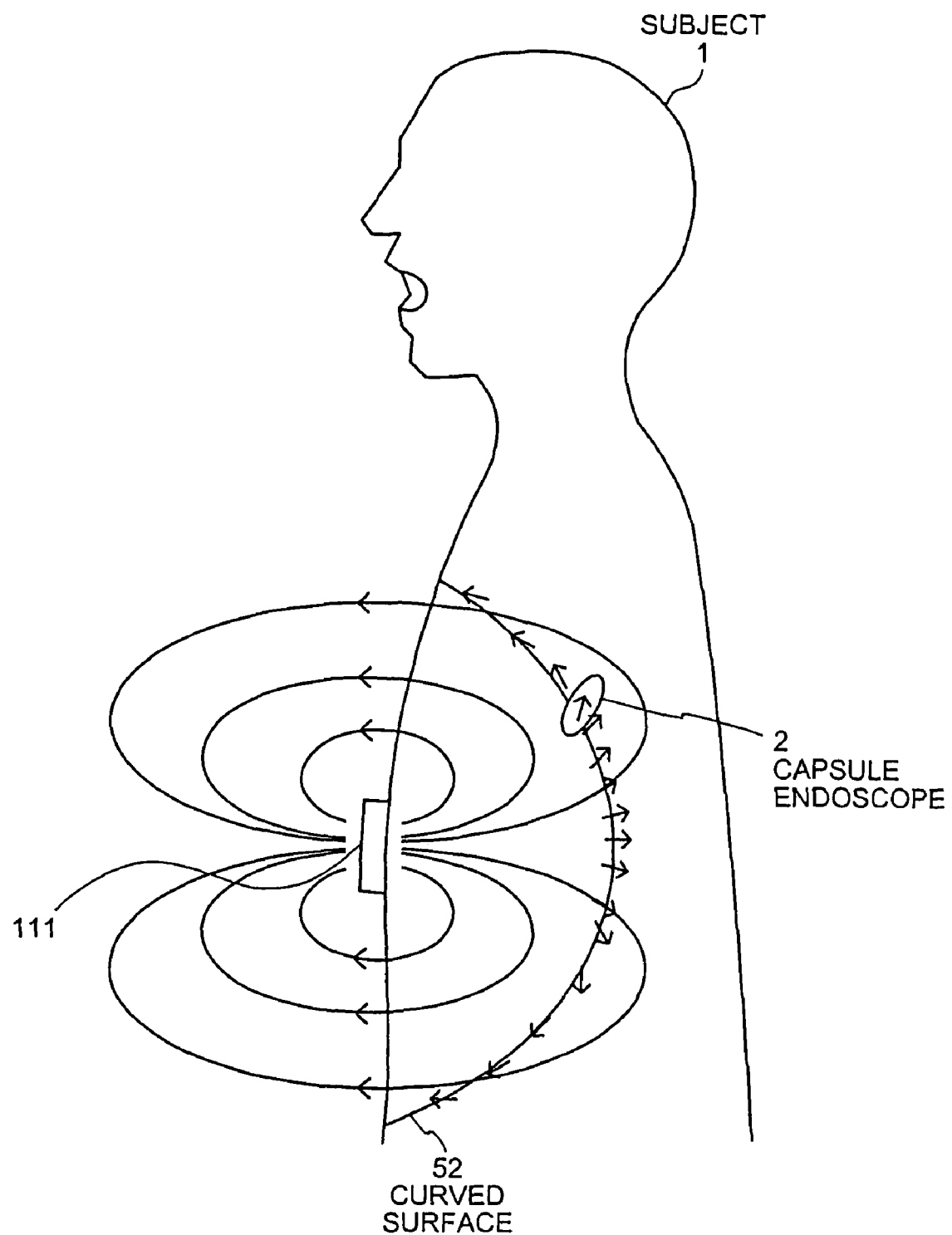
FIG. 26 is a schematic diagram of a use mode of the diffuse magnetic field at the time of position calculation.

The position calculator 141 then calculates the position of the capsule endoscope 2 on the curved surface 52 based on the magnetic field signal $S_3$, the orientation information calculated by the orientation calculator 140, and the information stored in the magnetic-field line orientation database 142. Specifically, the moving direction of the diffuse magnetic field at the present position of the capsule endoscope 2 is calculated based on the magnetic field signal $S_3$ and the orientation information. Since the magnetic field signal $S_3$ is a signal corresponding to the detection result of the diffuse magnetic field based on the target coordinate axis, the moving direction of the diffuse magnetic field in the reference coordinate axis at the present position of the capsule endoscope 2 is calculated, by applying the coordinate conversion processing from the target coordinate axis to the reference coordinate axis by using the orientation information, with respect to the moving direction of the diffuse magnetic field based on the magnetic field signal $S_3$. The magnetic-field line orientation database 142 stores the correspondence between the moving direction and the position of the diffuse magnetic field in the reference coordinate axis. Therefore, the position calculator 141 calculates, as shown in FIG. 26, the position corresponding to the moving direction of the diffuse magnetic field calculated by referring to the information stored in the magnetic-field line orientation database 142, and specifies the calculated position as the position of the capsule endoscope 2. This is the position calculation mechanism by the position calculator 141.

The selection mechanism of the second linear magnetic-field generating unit 110 used for position detection is explained next. In the body-insertable apparatus system according to the fifth embodiment, the magnetic-field generating areas 132a to 132d respectively generated by the second linear magnetic-field generating units 110a to 110d are formed so as to include only a part of the region inside the subject 1 where the capsule endoscope 2 can be positioned. In the fifth embodiment, therefore, a position where the second linear magnetic-field generating unit 110 should be present at the time of position detection is selected from the positions $P_1$ to $P_4$ by the position selector 149, and the drive controller 150 controls such that only the second linear magnetic-field generating unit 110 corresponding to the selected position is driven.

Figure 27:
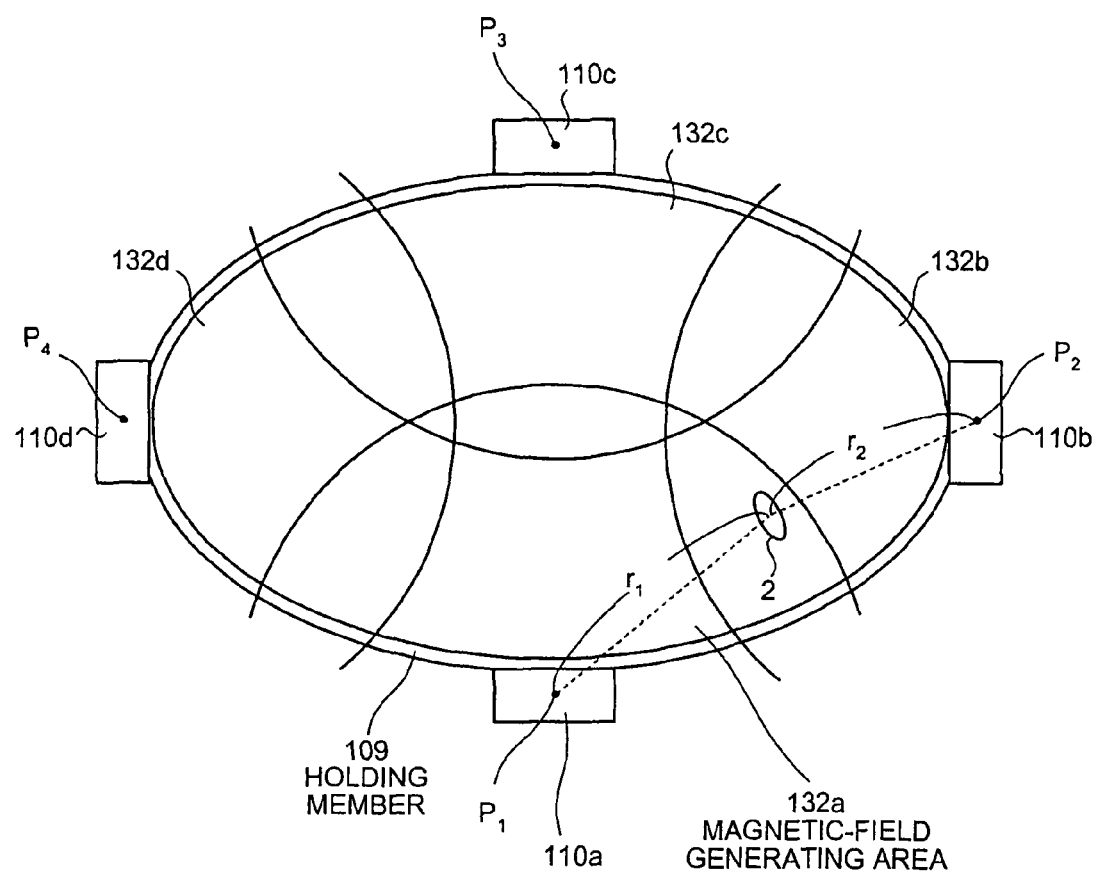
FIG. 27 is a schematic diagram for explaining a processing content of a position selector included in the processing device.

FIG. 27 is a schematic diagram of one example of the position where the capsule endoscope 2 is present at the first time instant. Position selection of the second linear magnetic-field generating unit 110 by the position selector 149 and drive control by the drive controller 150 are explained with reference to the example shown in FIG. 27.

The position selector 149 extracts information of the position of the capsule endoscope 2 at the past first time instant from the information recorded in the recording unit 143. The position selector 149 ascertains specific values of the positions $P_1$ to $P_4$, the range of the magnetic-field generating areas 132a to 132d, and the correspondence between the positions $P_1$ to $P_4$ and the magnetic-field generating areas 132a to 132d. As a result, the position selector 149 ascertains the position of the capsule endoscope 2 at the first time instant and the relationship between the position of the capsule endoscope 2 and the positions $P_1$ to $P_4$.

Based on the ascertainment of the position, the position selector 149 selects the most appropriate position of the magnetic-field generating area at the time of position detection to be performed at the second time instant, which is time after a predetermined time has passed since the first time instant. In the fifth embodiment, the position selector 149 selects a position closest to the position of the capsule endoscope 2 at the first time instant from the positions $P_1$ to $P_4$. Specifically, in the example in FIG. 27, the capsule endoscope 2 at the first time instant is positioned in an area away from position $P_1$ by a distance $r_1$, and away from position $P_2$ by a distance $r_2$ ($<r_1$). Accordingly, the position selector 149 selects position $P_2$ as the closest position, and outputs the selected position to the drive controller 150 as a position where the second linear magnetic-field generating unit 110 that generates the second magnetic field at the second time instant should be present.

On the other hand, the drive controller 150 drives the second linear magnetic-field generating unit 110 corresponding to the position selected by the position selector 149. Since the drive controller 150 ascertains beforehand the correspondence between the positions $P_1$ to $P_4$ and the second linear magnetic-field generating units 110a to 110d, the drive controller 150 performs predetermined control so that the second linear magnetic field is generated by the second linear magnetic-field generating unit 110b, for example, corresponding to an input of information indicating that the position $P_2$ is selected from the position selector 149 in the example shown in FIG. 27.

In the selection mechanism, the information of the position selected by the position selector 149 is also output to the orientation calculator 140 and the position calculator 141. In other words, for example, the moving direction and the strength distribution are different between the second linear magnetic field generated by the second linear magnetic-field generating unit 110a and the second linear magnetic field generated by the second linear magnetic-field generating unit 110b. Therefore, the orientation calculator 140 and the position calculator 141 need to ascertain which of the second linear magnetic-field generating units 110a to 110d is to generate the magnetic field, at the time of performing orientation calculation and position calculation, respectively.

An advantage of the body-insertable apparatus system according to the fifth embodiment is explained below. The body-insertable apparatus system according to the fifth embodiment adopts a configuration including a plurality of second linear magnetic-field generating units 110 functioning as the magnetic field generator that generates the second linear magnetic field, which has position dependency regarding the strength and functions as the position detecting magnetic field. Respective second linear magnetic-field generating units 110a to 110d do not cover the whole subject 1 singly, but covers the whole subject 1 as a whole, regarding any of the corresponding magnetic-field generating areas 132a to 132d. Therefore, the power consumption required for generating the magnetic field decreases in each of the second linear magnetic-field generating units 110a to 110d, as compared to a magnetic field generator that generates the magnetic-field generating area covering the whole subject 1 singly. Therefore, when only the one of the second linear magnetic-field generating units 110a to 110d corresponding to the selected position is driven, the electric energy required for generation of the position detecting magnetic field (the second linear magnetic field) can be reduced, as compared to the conventional body-insertable apparatus system.

On the other hand, in the fifth embodiment, since the range of the magnetic-field generating areas 132a to 132d generated by the individual second linear magnetic-field generating unit 110a to 110d is narrowed, such a problem does not occur that a significant magnetic field cannot be generated at a position where the capsule endoscope 2 as the detected object occupies at the time of position detection. In other words, in the fifth embodiment, the second linear magnetic field that covers the whole subject 1, at which the capsule endoscope 2 can be positioned, can be generated by the whole magnetic-field generating areas 132a to 132d. Therefore, by appropriately selecting the position of the second linear magnetic-field generating unit by the position selector 149, a significant magnetic field can be reliably generated at the time of position detection of the capsule endoscope 2, while reducing the electric energy required for generating the magnetic field.

Further, by narrowing the range of the magnetic-field generating areas 132a to 132d generated by the individual second linear magnetic-field generating unit 110a to 110d, the influence of the magnetic field on the electronic equipment present outside the subject 1 can be reduced. That is, by setting the magnetic-field generating area to be narrow, the strength of the magnetic field generated outside the sub 1 is reduced, thereby enabling a reduction of the influence of the magnetic field on the electronic equipment positioned outside the subject 1.

In the fifth embodiment, a position closest to the position of the capsule endoscope 2 at the first time instant is selected from the positions $P_1$ to $P_4$, as a reference at the time of selecting the position by the position selector 149. By adopting such a configuration, in the fifth embodiment, the second linear magnetic field having a detectable strength can be reliably generated relative to the area where the capsule endoscope 2 is present at the second time instant.

The magnetic field is generated by the second linear magnetic-field generating unit 110 corresponding to the selected position at the second time instant when a predetermined time has passed since the first time instant. When the capsule endoscope 2 moves between the first time instant and the second time instant, the position of the capsule endoscope 2 at the second time instant is different from the position at the first time instant by a predetermined distance. Therefore, when the position of the second linear magnetic-field generating unit 110 is selected based on the position at the first time instant, there is a possibility that the capsule endoscope 2 can be positioned in an area outside the corresponding magnetic-field generating area 132 at the second time instant.

On the other hand, in the fifth embodiment, by selecting the position closest to the position of the capsule endoscope 2 at the first time instant from the positions $P_1$ to $P_4$, the reliability of the capsule endoscope 2 being present within the range of the magnetic-field generating area 132 generated corresponding to the selected position P can be improved. In other words, referring to the position shown in FIG. 27, the capsule endoscope 2 at the first time instant has a distance from the margin of the magnetic-field generating area 132b larger than a distance from the margin of the magnetic-field generating area 132a by the portion approaching the position $P_2$. Therefore, the capsule endoscope 2 in the example shown in FIG. 27 has a lower possibility of deviating from the magnetic-field generating area 132b than the possibility of deviating from the magnetic-field generating area 132a at the second time instant. As a result, by selecting the closest position, the possibility of deviating from the corresponding magnetic-field generating area can be reduced, thereby enabling more reliable position detection at the second time instant.

A body-insertable apparatus system according to a sixth embodiment is explained next. In the body-insertable apparatus system according to the sixth embodiment, a single second linear magnetic field generating unit moves to a position selected by the position selector, thereby generating the second linear magnetic field.

Figure 28:
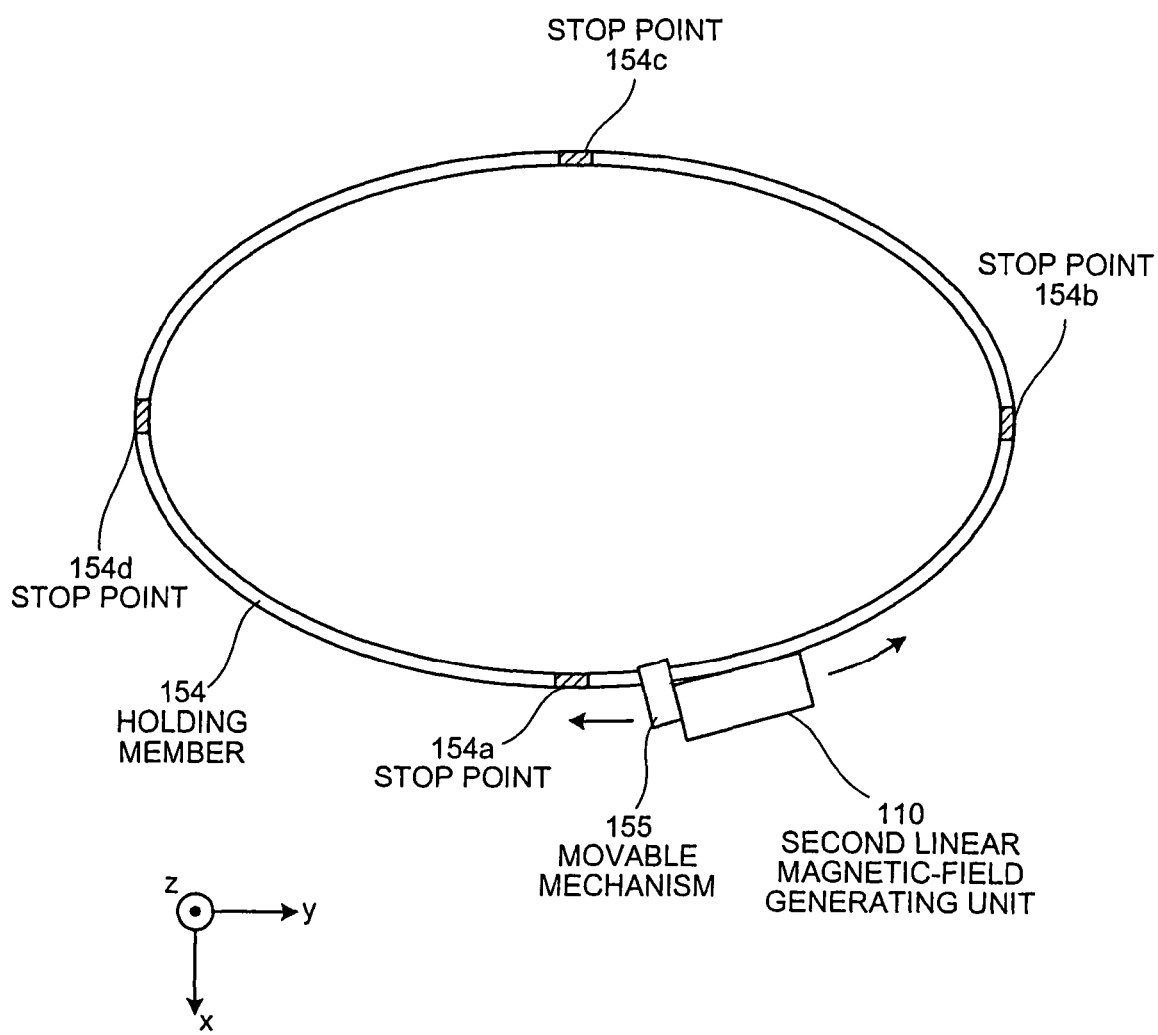
FIG. 28 is a schematic diagram of a configuration of a holding member and a second linear magnetic field generating unit included in a body-insertable apparatus system according to a sixth embodiment.

FIG. 28 is a schematic diagram of a relationship between the second linear magnetic field generating unit 110 and a holding member 154 included in the body-insertable apparatus system according to the sixth embodiment. The body-insertable apparatus system according to the sixth embodiment basically has the same configuration as that of the fifth embodiment, and includes the capsule endoscope 2, the display device 4, and the portable recording medium 5 as in the fifth embodiment, although not shown. The position detecting apparatus includes the receiving antennas 106a to 106d, the transmitting antennas 107a to 107d, the first linear magnetic-field generating unit 108, the second linear magnetic-field generating unit 110, and the diffuse magnetic-field generating unit 111 as in the fifth embodiment, other than the holding member 154 and a processing device 156 described below. In the sixth embodiment, parts denoted by like names or reference numerals as in the fifth embodiment have like structures and functions as in the fifth embodiment, unless otherwise specified.

As shown in FIG. 28, in the sixth embodiment, the second linear magnetic-field generating unit 110 has the same structures and functions as those of the respective second linear magnetic-field generating unit 110a to 110d in the fifth embodiment. On the other hand, the second linear magnetic-field generating unit 110 is not fixed to the holding member 154, but is held movably. Specifically, the holding member 154 functions as a guide member. On the other hand, the second linear magnetic-field generating unit 110 moves along the holding member 154 by a movable mechanism 155. Stop points 154a to 154d are formed on the holding member 154 at positions corresponding to the positions $P_1$ to $P_4$ in the fifth embodiment. The movable mechanism 155 has a function of detecting the respective stop points 154a to 154d, to move the second linear magnetic-field generating unit 110 relative to the respective positions $P_1$ to $P_4$.

Figure 29:
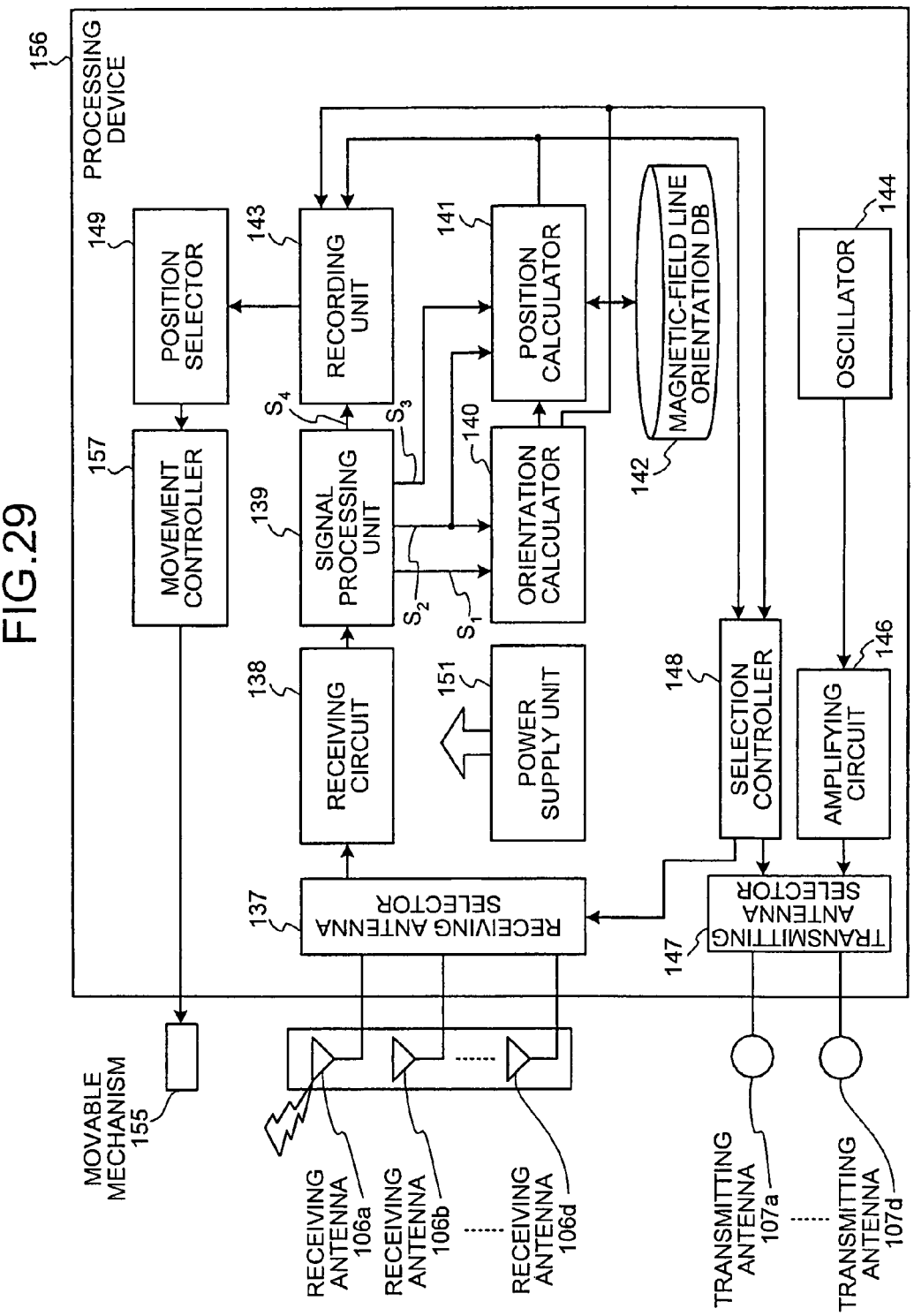
FIG. 29 is a schematic block diagram of a configuration of a processing device 12 that forms the position detecting apparatus included in the body-insertable apparatus system.

The processing device 156 included in the position detecting apparatus is explained next. FIG. 29 is a schematic block diagram of the configuration of the processing device 156. While the processing device 156 basically has a common configuration with the processing device 112 in the fifth embodiment, it newly includes a movement controller 157 that controls a moving state of the second linear magnetic-field generating unit 110 by the movable mechanism 155. Specifically, the movement controller 157 controls the movable mechanism 155 so that the second linear magnetic-field generating unit 110 is moved to the position selected from the positions $P_1$ to $P_4$ by the position selector 149.

Figure 30:
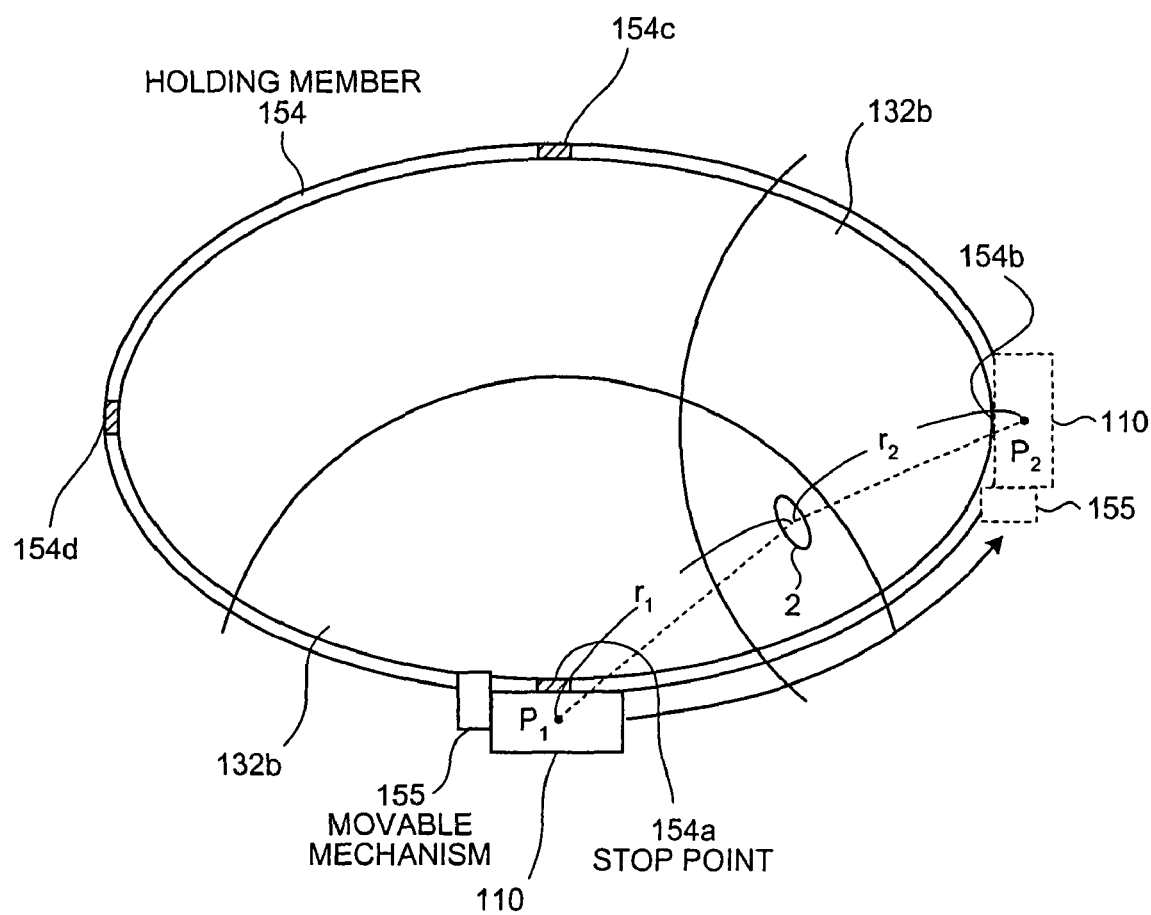
FIG. 30 is a schematic diagram for explaining an operation of the second linear-magnetic field generating unit generated by position selection.

FIG. 30 is a schematic diagram for explaining a moving mode of the second linear magnetic-field generating unit 110 based on the position selection performed by the position selector 149. The position selector 149 selects $P_2$, as in the example in FIG. 27, as a position where the second linear magnetic-field generating unit 110 that functions as the magnetic field generator at the time of position detection at the second time instant is to be arranged, from the positions $P_1$ to $P_4$ based on the position or the like of the capsule endoscope 2 at the first time instant as in the fifth embodiment. The position selector 149 outputs information of the selected position $P_2$ to the movement controller 157, and the movement controller 157 instructs the movable mechanism 155 to move the second linear magnetic-field generating unit 110 to the position $P_2$. Upon reception of this instruction, as shown in FIG. 30, the movable mechanism 155 moves the second linear magnetic-field generating unit 110 in a counterclockwise direction along the holding member 154, and the second linear magnetic-field generating unit 110 is arranged at position $P_2$ by detecting the stop point 154b. Therefore, the second linear magnetic-field generating unit 110 generates the second linear magnetic field in the state arranged at position $P_2$.

An advantage of the body-insertable apparatus system according to the sixth embodiment is explained next. In the body-insertable apparatus system according to the sixth embodiment, the second linear magnetic-field generating unit 110 that generates the second linear magnetic field functioning as the position detecting magnetic field generates the magnetic field so as to cover only a part of the subject 1, as in the second linear magnetic-field generating units 110a to 110d in the fifth embodiment. Accordingly, there is an advantage in that the power required at the time of generating the second linear magnetic field can be reduced as in the fifth embodiment.

Further, in the sixth embodiment, by adopting the configuration such that a plurality of second linear magnetic-field generating units 110 is not provided, but a single mechanism can move to a plurality of positions, the same function as that when a plurality of second linear magnetic-field generating units 110 is provided can be achieved. Accordingly, in the sixth embodiment, the number of the second linear magnetic-field generating unit 110 can be reduced as compared to the fifth embodiment, and hence there is an advantage in that the body-insertable apparatus system can be achieved with the configuration thereof being simplified, and production cost thereof being reduced, in addition to the advantage of the fifth embodiment.

A body-insertable apparatus system according to a seventh embodiment is explained next. In the body-insertable apparatus system according to the seventh embodiment, the magnetic field generator does not directly perform position selection based on the position of the capsule endoscope 2 at the first time instant, however, predicts the position of the capsule endoscope 2 at the second time instant based on the position at the first time instant and performs position selection based on the prediction result.

Figure 31:
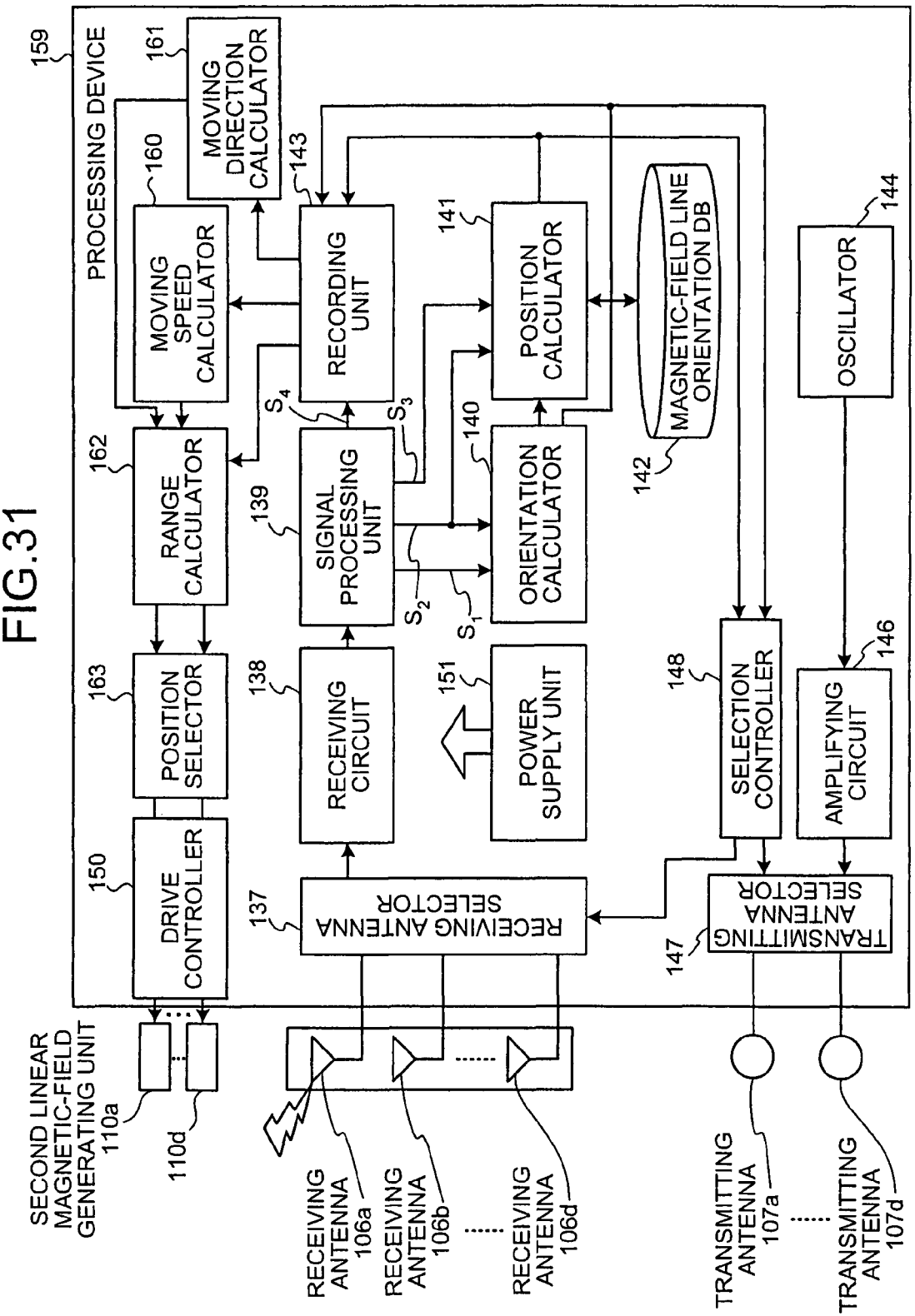
FIG. 31 is a schematic block diagram of a configuration of a processing device included in a body-insertable apparatus system according to a seventh embodiment.

FIG. 31 is a schematic block diagram of a configuration of a processing device 159 included in the body-insertable apparatus system according to the seventh embodiment. As shown in FIG. 31, the processing device 159 basically has the same configuration as the processing device 112 in the fifth embodiment. On the other hand, the processing device 159 includes a moving speed calculator 160 that calculates the moving speed of the capsule endoscope 2, a moving direction calculator 161 that calculates the moving direction of the capsule endoscope 2, and a range calculator 162 that calculates the possible existence range of the capsule endoscope 2 at the second time instant based on the position of the capsule endoscope 2 at the first time instant, and the calculated moving speed and moving direction of the capsule endoscope 2. The position selector 163 selects the position of the magnetic field generator that generates the second linear magnetic field at the time of position detection at the second time instant from positions $P_1$ to $P_4$ based on the possible existence range calculated by the range calculator 162.

The moving speed calculator 160 calculates the moving speed of the capsule endoscope 2 from the first time instant to the second time instant based on the information recorded in the recording unit 43. Specifically, the moving speed calculator 160 calculates an average speed, for example, based on the variation of the position of the capsule endoscope 2 detected at a plurality of past time instants to calculate the moving speed.

The moving direction calculator 161 calculates the moving direction of the capsule endoscope 2 from the first time instant to the second time instant based on the information recorded in the recording unit 143. The processing device 159 has a configuration including an orientation calculator 140 as in the fifth embodiment, and information of the orientation of the target coordinate axis relative to the reference coordinate axis calculated by the orientation calculator 140 at the first time instant, that is, information relating to which direction the capsule endoscope 2 is oriented relative to the reference coordinate axis is recorded in the recording unit 143. On the other hand, the moving direction calculator 161 extracts the orientation of the capsule endoscope 2 (generally, the longitudinal direction of the capsule endoscope 2) from the recording unit 143 based on the information of the orientation detected at the first time instant, to derive this direction as the moving direction.

Figure 32:
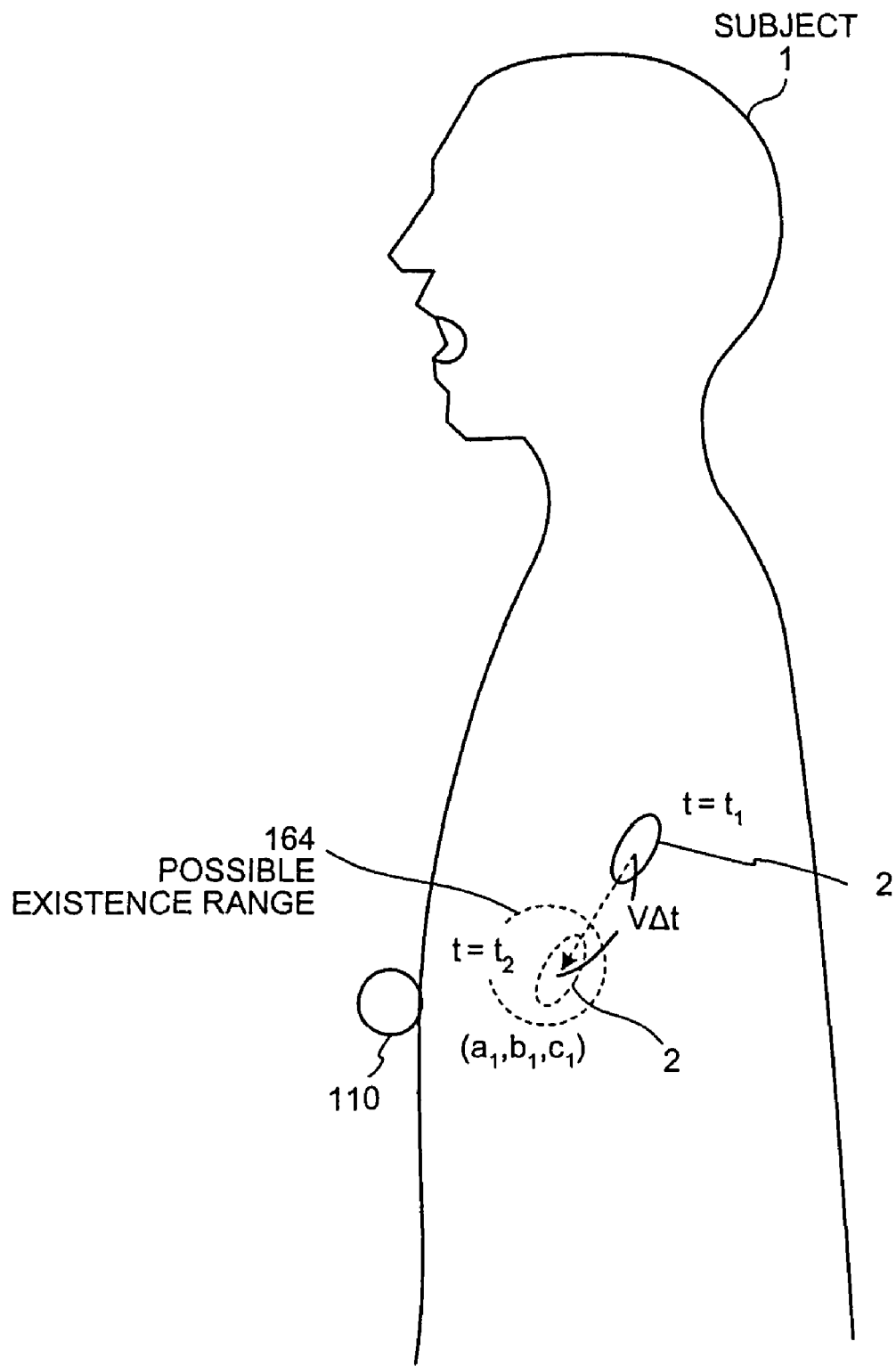
FIG. 32 is a schematic diagram for explaining the calculation mode of the possible existence range.

The range calculator 162 calculates the possible existence range, in which there is a high possibility that the capsule endoscope 2 is present at the second time instant, based on the calculation results by the moving speed calculator 160 and the moving direction calculator 161. FIG. 32 is a schematic diagram for explaining calculation of the possible existence range by the range calculator 162. As shown in FIG. 32, the range calculator 162 extracts the information relating to the position of the capsule endoscope 2 at the first time instant (time instant $t_1$ in FIG. 32) from the recording unit 143. The range calculator 162 then presumes an area extended from the extracted position toward moving direction vectors ($a_1, b_1, c_1$) by a product obtained by multiplying the moving speed v by a difference $\Delta t$ between the second time instant and the first time instant as a position where the capsule endoscope 2 will be present at the second time instant (time instant $t_2$ in FIG. 32), to calculate the possible existence range 164 including this area.

The position selector 163 selects the position based on the possible existence range calculated by the range calculator 162. That is, in the fifth embodiment and the like, the position of the second linear magnetic-field generating unit 110 is selected based on the position of the capsule endoscope 2 at the first time instant, for example, as shown in FIG. 27. However, in the seventh embodiment, the position selector 163 selects the position of the second linear magnetic-field generating unit 110 based on the position of the possible existence range, which is the predicted range of the position of the capsule endoscope 2 at the second time instant. Since the position selection mechanism is the same as that of the fifth and the sixth embodiments, and the operation of the drive controller 150 and the like based on the result of the position selection is the same as in the fifth embodiment, the explanation thereof is omitted.

An advantage of body-insertable apparatus system according to the seventh embodiment is explained. In the seventh embodiment, the range calculator 162 is newly provided to select the position of the second linear magnetic-field generating unit 110 based on the predicted position of the capsule endoscope 2 at the second time instant. Therefore, in the body-insertable apparatus system according to the seventh embodiment, the position detecting magnetic field can be generated more reliably at the position where the capsule endoscope 2 is present at the second time instant, in addition to the advantage of the fifth embodiment and the like. Accordingly, the body-insertable apparatus system according to the seventh embodiment can perform reliable position detection, while having an advantage in that the power consumption can be reduced, even in the position detection in an area, for example, in which the capsule endoscope 2 irregularly moves.

A body-insertable apparatus system according to an eighth embodiment is explained next. The body-insertable apparatus system according to the eighth embodiment has a function of performing the position detection by using the earth magnetism instead of the first linear magnetic field.

Figure 33:
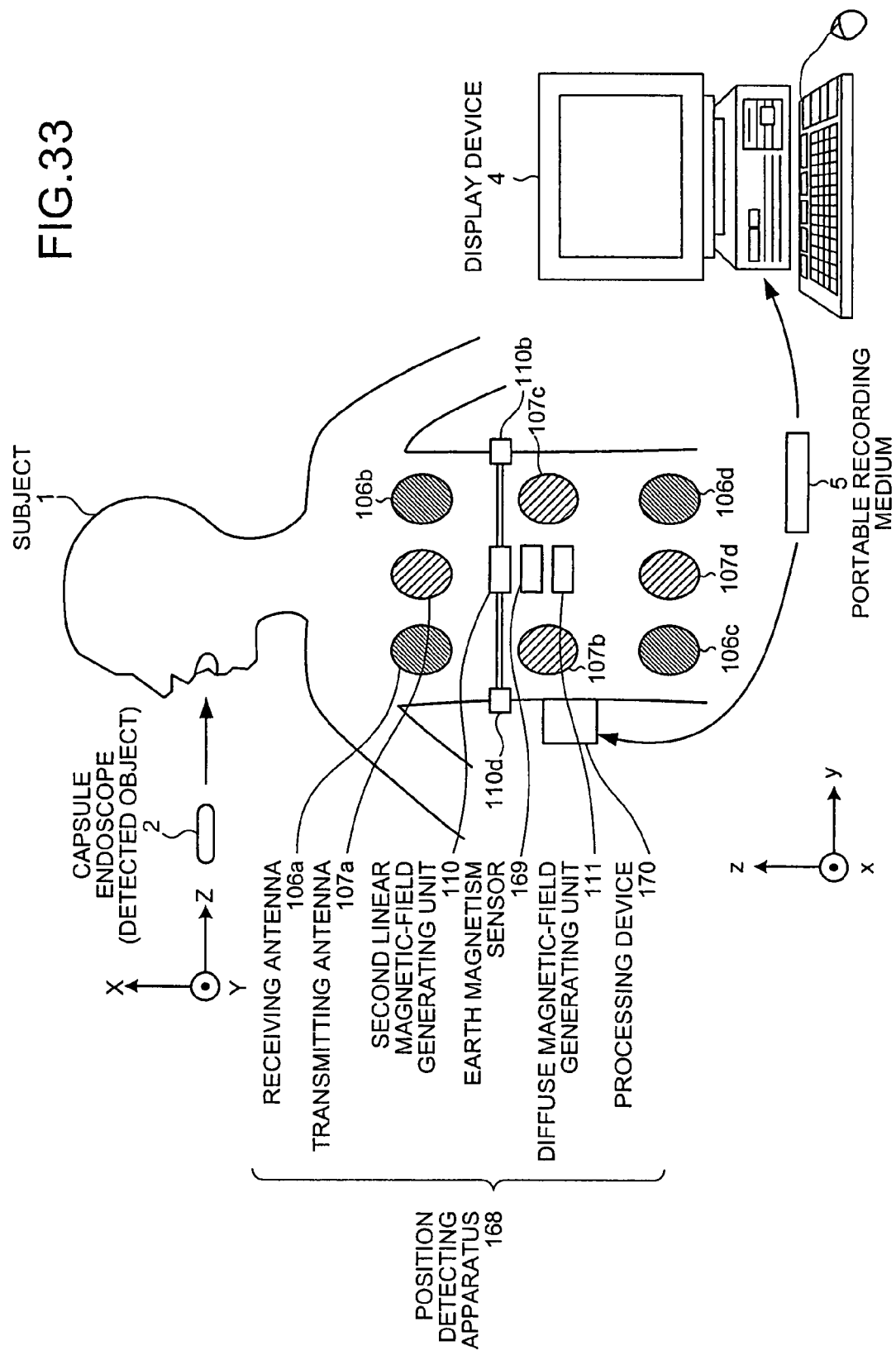
FIG. 33 is a schematic diagram of an overall configuration of a body-insertable apparatus system according to an eighth embodiment.

FIG. 33 is a schematic diagram of an overall configuration of the body-insertable apparatus system according to the eighth embodiment. As shown in FIG. 33, the body-insertable apparatus system according to the eighth embodiment includes the capsule endoscope 2, the display device 4, and the portable recording medium 5 as in the fifth to the seventh embodiments, while the configuration of the position detecting apparatus 168 is different. Specifically, the first linear magnetic-field generating unit 108 included in the position detecting apparatus in the fifth embodiment and the like is omitted, and an earth magnetism sensor 169 is newly included. The processing device 170 also has a different configuration from the fifth embodiment and the like.

The earth magnetism sensor 169 basically has the same configuration as that of the magnetic field sensor 16 included in the capsule endoscope 2. That is, the earth magnetism sensor 169 detects the strength of the magnetic field components in predetermined three axial directions in an area where it is arranged, and outputs an electric signal corresponding to the detected magnetic field strength. On the other hand, the earth magnetism sensor 169 is arranged on the body surface of the subject 1, which is different from the magnetic field sensor 16, and detects the strength of the magnetic field components respectively corresponding to the x-axis, y-axis, and z-axis directions in the reference coordinate axis fixed to the subject 1. In other words, the earth magnetism sensor 169 has a function of detecting the moving direction of the earth magnetism, and outputs the electric signal corresponding to the magnetic field strength detected for the x-axis direction, the y-axis direction, and the z-axis direction to the processing device 170.

Figure 34:
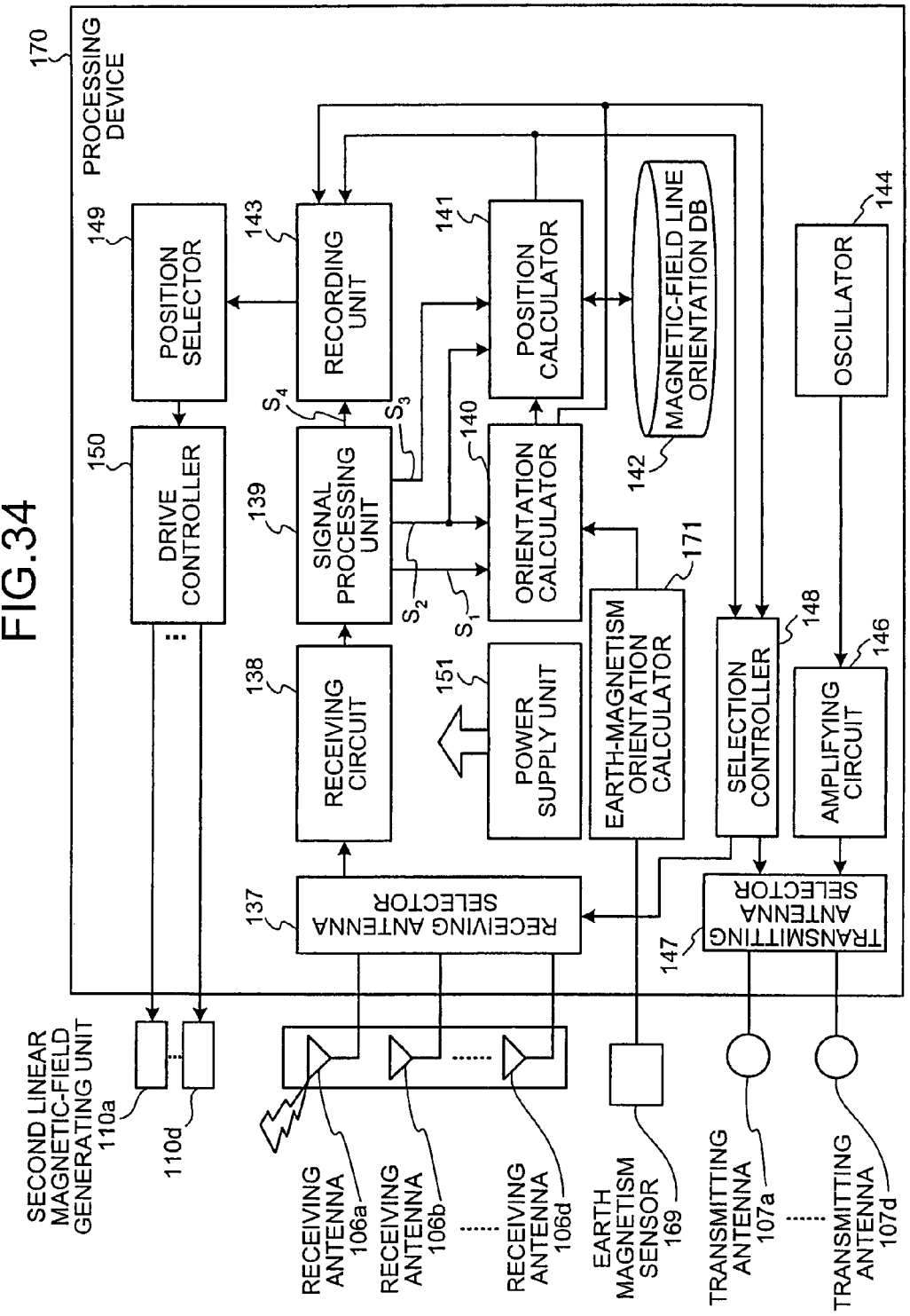
FIG. 34 is a schematic block diagram of a configuration of the processing device included in the body-insertable apparatus system.

The processing device 170 in the eighth embodiment is explained next. FIG. 34 is a block diagram of a configuration of the processing device 170. As shown in FIG. 34, the processing device 170 basically has the same configuration as that of the processing device 112 in the fifth embodiment. On the other hand, the processing device 170 includes an earth-magnetism orientation calculator 171 that calculates the moving direction of the earth magnetism on the reference coordinate axis based on the electric signal input from the earth magnetism sensor 169, and outputs the calculation result to the orientation calculator 140.

There is a problem in calculation of the moving direction of the earth magnetism on the reference coordinate axis fixed to the subject 1, when the earth magnetism is used as the first linear magnetic field. That is, since the subject 1 can freely move while the capsule endoscope 2 is moving in the body, it is predicted that the position relationship between the reference coordinate axis fixed to the subject 1 and the earth magnetism changes with the movement of the subject 1. On the other hand, from a standpoint of calculating the position of the target coordinate axis relative to the reference coordinate axis, when the moving direction of the first linear magnetic field on the reference coordinate axis becomes unclear, there is a problem in that the correspondence between the reference coordinate axis and the target coordinate axis cannot be clarified relating to the moving direction of the first linear magnetic field.

Accordingly, in the eighth embodiment, the earth magnetism sensor 169 and the earth-magnetism orientation calculator 171 are provided for monitoring the moving direction of the earth magnetism, which will change on the reference coordinate axis due to movement or the like of the subject 1. In other words, the earth-magnetism orientation calculator 171 calculates the moving direction of the earth magnetism on the reference coordinate axis based on the detection result of the earth magnetism sensor 169, and outputs the calculation result to the orientation calculator 140. On the other hand, the orientation calculator 140 can calculate the correspondence between the reference coordinate axis and the target coordinate axis relating to the moving direction of the earth magnetism, by using the input moving direction of the earth magnetism, and the calculated correspondence is used together with the correspondence in the second linear magnetic field to calculate the orientation information.

The moving directions of the earth magnetism and the second linear magnetic field generated by the second linear magnetic-field generating unit 110 can be parallel to each other, depending on the direction of the subject 1. In this case, the position relationship can be detected by also using data relating to the orientation of the target coordinate axis at the time immediately before and the position of the origin. Further, to avoid that the moving directions of the earth magnetism and the second linear magnetic field become parallel to each other, it is also effective to have such a configuration that the extending direction of the coil 134 constituting the second linear magnetic-field generating unit 110 is not set to the y-axis direction in the reference coordinate axis, as shown in FIG. 3, but for example, set to the z-axis direction. Alternatively, the position detecting apparatus 168 may further include a sub-linear magnetic-field generating unit and a magnetic-field controller so that the moving directions of the earth magnetism and linear magnetic field which are generated in the region inside the subject 1 are not parallel to each other. The sub-linear magnetic-field generating unit generates a linear magnetic field different from the second linear magnetic field in moving direction (magnetic-field direction), in the region inside the subject 1 including the position of the capsule endoscope 2; the magnetic-field controller drives one of the second linear magnetic-field generating unit 110 and the sub-linear magnetic-field generating unit, based on a geometric relation between the linear magnetic field generated in the region inside the subject 1 and the earth magnetism. In this configuration, the magnetic-field controller determines whether the moving direction of the linear magnetic field generated by the second linear magnetic-field generating unit 110 and the moving direction of the earth magnetism calculated by the earth-magnetism orientation calculator 171 are parallel to each other or not, and drives one of the second linear magnetic-field generating unit 110 and the sub-linear magnetic-field generating unit based on the result of determination. Specifically, the magnetic-field controller causes the second linear magnetic-field generating unit 110 to generate a linear magnetic field if the moving direction of the linear magnetic field generated by the second linear magnetic-field generating unit 110 is not parallel to the moving direction of the earth magnetism. On the other hand, the magnetic-field controller causes the sub-linear magnetic-field generating unit, in place of the second linear magnetic-field generating unit 110, to generate a linear magnetic field if the moving direction of the linear magnetic field generated by the second linear magnetic-field generating unit 110 is parallel to the moving direction of the earth magnetism. As a result, the position detecting apparatus 168 can reliably generate the linear magnetic field different from the second linear magnetic field in moving direction (i.e., the linear magnetic field having a magnetic field component magnetic-field in a direction not parallel to the moving direction of the earth magnetism), in the region inside the subject 1 including the position of the capsule endoscope 2.

An advantage of a position detecting system according to the eighth embodiment is explained next. The position detecting system according to the eighth embodiment has an advantage by using the earth magnetism in addition to the advantage of the fifth embodiment. That is, the mechanism for generating the first linear magnetic field can be omitted by adopting the configuration using the earth magnetism as the first linear magnetic field. Therefore, while the burden on the subject 1 at the time of introducing the capsule endoscope 2 can be reduced, the position of the target coordinate axis relative to the reference coordinate axis can be calculated. Since the earth magnetism sensor 169 can be formed by using the MI sensor or the like, the earth magnetism sensor 169 can have a small size, and the burden on the subject 1 does not increase by newly providing the earth magnetism sensor 169.

Further, there is a further advantage from a standpoint of reducing the power consumption, by adopting the configuration in which the earth magnetism is used as the first linear magnetic field. That is, when the first linear magnetic field is formed by using the coil or the like, the power consumption increases due to the electric current allowed to flow to the coil. However, such power consumption becomes unnecessary due to the earth magnetism, thereby enabling realization of a low power-consumption system.

While the present invention has been explained by the fifth to the eighth embodiments, the present invention is not limited thereto, and a person skilled in the art will be able to consider various embodiments and modifications. For example, in the fifth to the eighth embodiments, the second linear magnetic field is employed as an example of the position detecting magnetic field, and the second linear magnetic-field generating unit 110 is used as an example of the magnetic-field generator. However, the configuration need not be limited thereto, and the first linear magnetic field, the diffuse magnetic field, or other magnetic fields can be used as the position detecting magnetic field, and the first linear magnetic-field generating unit 108, the diffuse magnetic-field generating unit 111, or other magnetic-field generating units can be used as the magnetic-field generator. In other words, for example, such a configuration can be adopted that the inside of the subject 1 is divided into a plurality of regions, a plurality of first linear magnetic-field generating units 108 is provided for each of the divided regions, and positions corresponding to the first linear magnetic-field generating units 108 can be selected by the position selector. Further, as a position selection mode by the position selector, for example, a selection mode other than using the distance between positions $P_1$ to $P_4$ can be adopted, so long as an area where the capsule endoscope is positioned at the second time instant is selected based on the position of the capsule endoscope 2 at the first time instant, so as to be included in the magnetic-field generating area.

The present invention is not limited to the body-insertable apparatus system as an application object of the position detecting apparatus. As is obvious from the above explanation, the present invention is applicable to the general position detecting apparatus that detects positions by using the position detecting magnetic field, and the advantages of the present invention can be obtained for the general position detecting apparatuses.

Further, a configuration combining the fifth to the eighth embodiments with each other can be adopted. For example, the advantages of the present invention can be obtained for the mechanism that moves the single second linear magnetic-field generating unit 110 to the selected position as shown in the sixth embodiment, and the position detecting apparatus and the body-insertable apparatus system using a compatible combination like the mechanism such as the range calculator as shown in the seventh embodiment.

Figure 35:
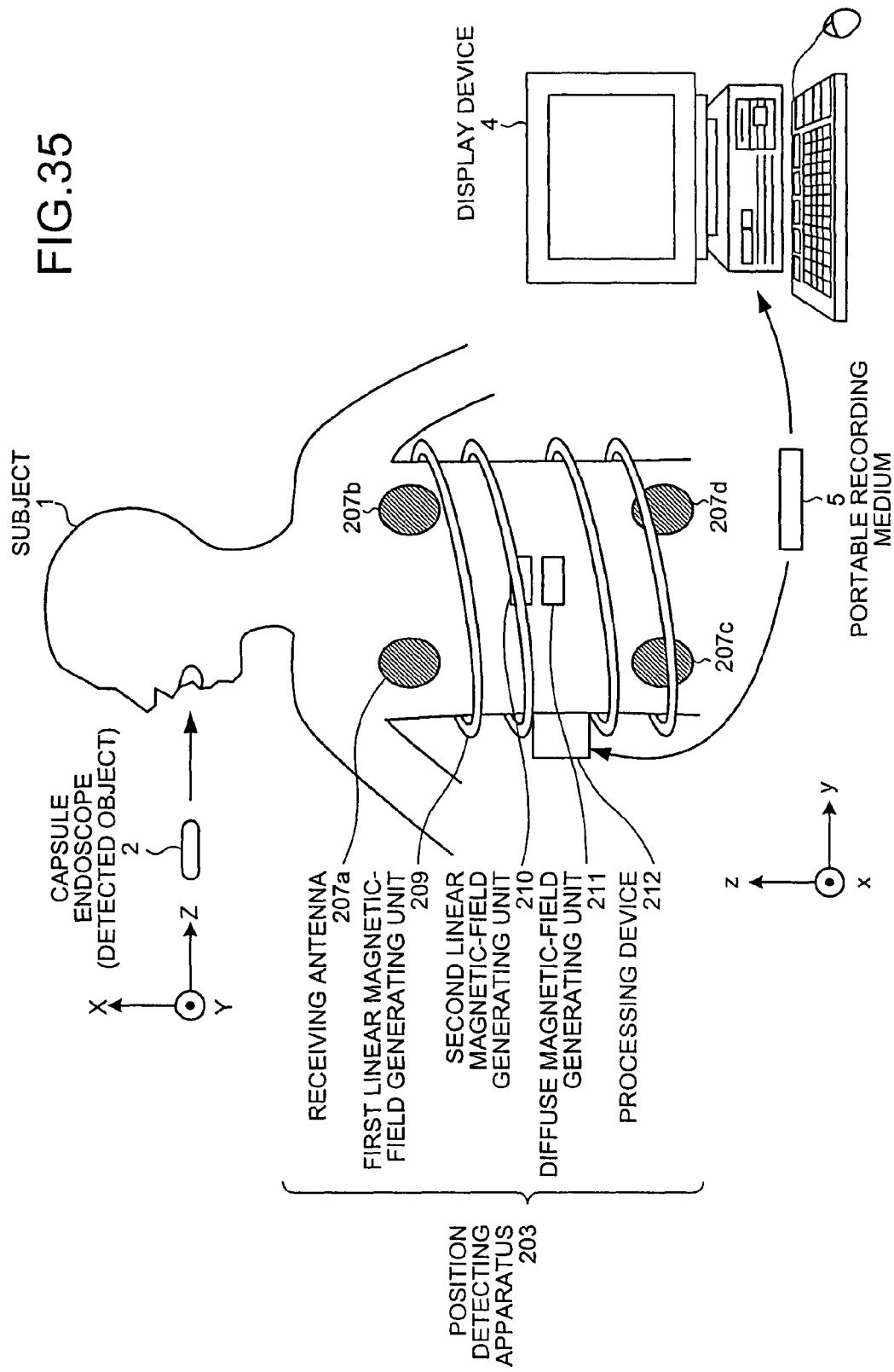
FIG. 35 is a schematic diagram of an overall configuration of a body-insertable apparatus system according to a ninth embodiment.

A body-insertable apparatus system according to a ninth embodiment is explained next. FIG. 35 is a schematic diagram of an overall configuration of the body-insertable apparatus system according to the ninth embodiment. In FIG. 35, since the display device 4 and the portable recording medium 5 have the same configuration as those of the first and the fifth embodiments, the explanation thereof is omitted. A different point from the first and the fifth embodiments is the configuration of the capsule endoscope 2 and a position detecting apparatus 203.

Figure 36:
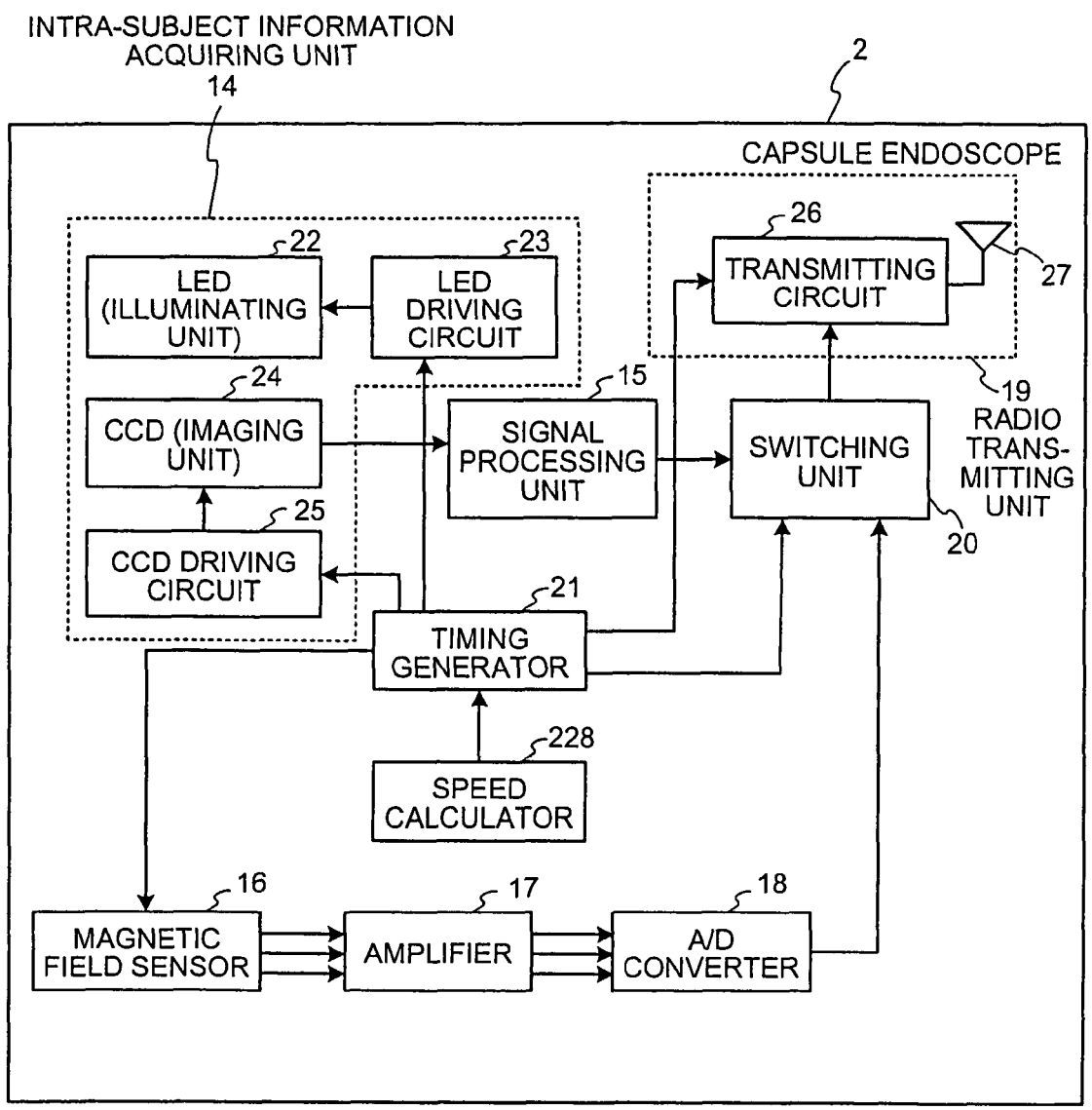
FIG. 36 is a schematic block diagram of a configuration of the capsule endoscope included in the body-insertable apparatus system.

A different point of the capsule endoscope 2 according to the ninth embodiment from that of the first and the fifth embodiment is that it includes, as shown in FIG. 36, a speed calculator 228 that calculates the moving speed of the capsule endoscope 2 in the subject 1, and a timing controller 21 that controls the drive timing of the intra-subject information acquiring unit 14, the magnetic field sensor 16, the radio transmitting unit 19, and the like based on the calculation result of the speed calculator 228.

The switching unit 20 appropriately switches the magnetic field signal output via the A/D converter 18, the image signal output via the signal processing unit 15, and a drive timing signal output from the timing controller 21 to output the signal to the radio transmitting unit 19. Accordingly, the magnetic field signal, the image signal, and the drive timing signal are included in the radio signal transmitted via the radio transmitting unit 19. In a processing device 212 (described later) included in the position detecting apparatus 203, the radio signal transmitted from the capsule endoscope 2 is respectively reconstructed as the magnetic field signals $S_1$ to $S_3$, the image signal $S_4$, and a drive timing signal $S_5$.

The speed calculator 228 calculates the moving speed as an example of the moving state of the capsule endoscope 2. A specific configuration of the speed calculator 228 includes, for example, an acceleration sensor such as a small gyroscope, and a mechanism for calculating time integration of the acceleration detected by the acceleration sensor, and has a function of outputting the calculated moving speed to the timing controller 21.

The timing controller 21 controls the drive timing of at least the magnetic field sensor 16 and the radio transmitting unit 19 of the components of the capsule endoscope 2. Specifically, the timing controller 21 sets a drive cycle of the magnetic field sensor 16 and the like based on the moving state of the capsule endoscope 2, the moving speed of the capsule endoscope 2 in the ninth embodiment, and drives the magnetic field sensor 16 and the like at the timing matched with the set drive cycle. That is, the intra-subject information acquiring unit 14 and the magnetic field sensor 16 respectively a repeat acquisition operation and a magnetic-field detection operation of the intra-subject information, with the movement of the capsule endoscope 2. The radio transmitting unit 19 repeats a predetermined radio transmission operation corresponding to such a repeated operation. In the ninth embodiment, the timing controller 21 specifies the cycle of the repeated operation, and setting of the drive cycle and the like is explained later in detail.

The timing controller 21 generates a drive timing signal as the information of the drive timing such as the set drive cycle, and the generated drive timing signal is transmitted to the position detecting apparatus 3 via the radio transmitting unit 19 together with other signals. The timing controller 21 also controls an operation content of the switching unit 20, and specifically, controls switching timing of the magnetic field signal, the image signal, and the drive timing signal input to the switching unit 20.

The position detecting apparatus 203 is explained below. As shown in FIG. 35, the position detecting apparatus 203 includes receiving antennas 207a to 207d for receiving the radio signal transmitted from the capsule endoscope 2, a first linear magnetic-field generating unit 209 that generates the first linear magnetic field, a second linear magnetic-field generating unit 210 that form the second linear magnetic field, a diffuse magnetic-field generating unit 211 that generates the diffuse magnetic field, and a processing device 212 that performs predetermined processing to the radio signal and the like received via the receiving antennas 207a to 207d. Since the receiving antennas 207a to 207d, the first linear magnetic-field generating unit 209, and the second linear magnetic-field generating unit 210 have the same configuration as those of the receiving antennas 7a to 7d, the first linear magnetic-field generating unit 9, and the second linear magnetic-field generating unit 10 in the first embodiment, the explanation thereof is omitted.

Figure 37:
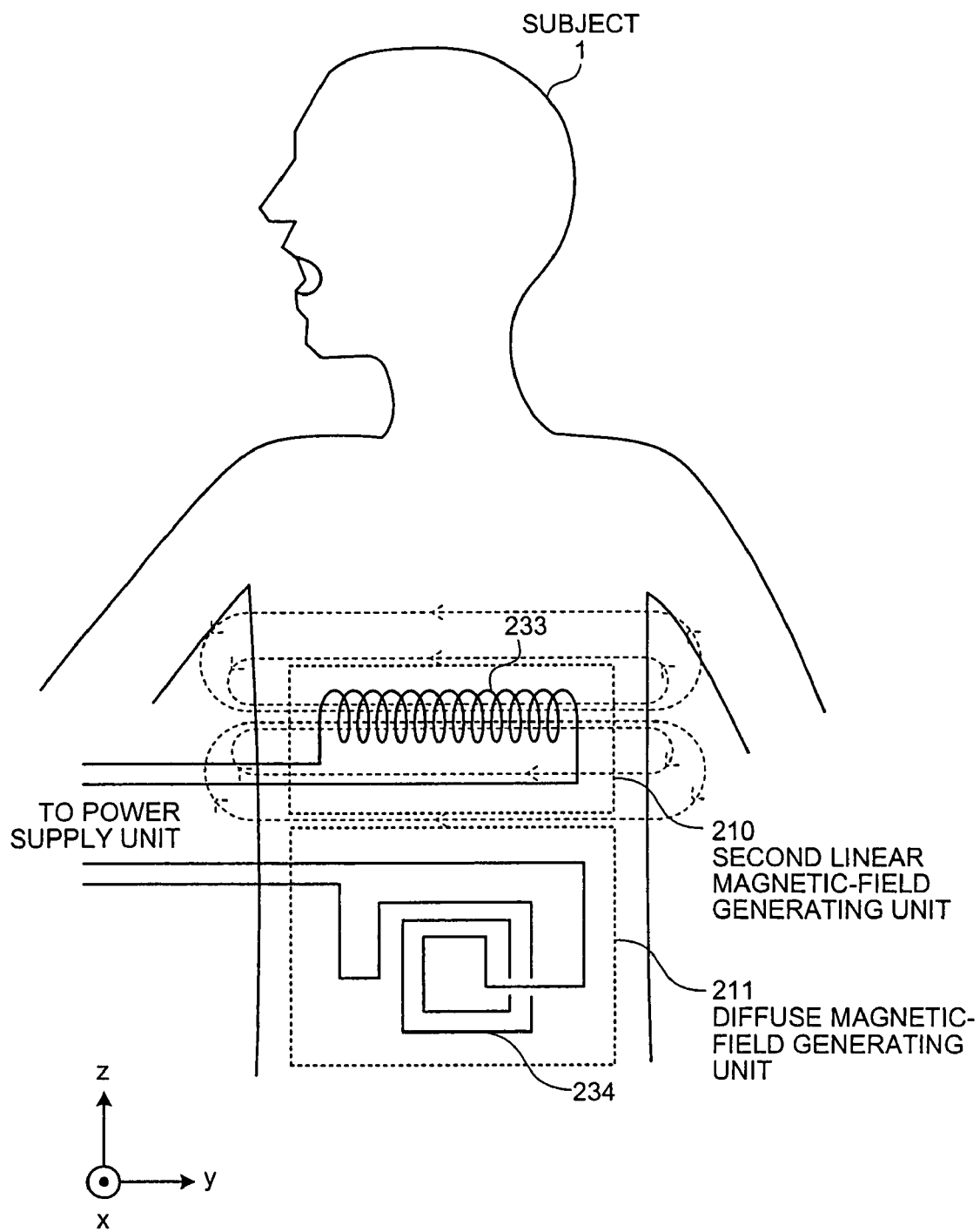
FIG. 37 is a schematic diagram of a configuration of the second linear magnetic field generating unit and the diffuse magnetic-field generating unit included in the position detecting apparatus, and a mode of the second linear magnetic field generated by the second linear magnetic field generating unit.

FIG. 37 is a schematic diagram of a configuration of the second linear magnetic field generating unit 210 and the diffuse magnetic-field generating unit 211, and a mode of the second linear magnetic field generated by the second linear magnetic field generating unit 210. As shown in FIG. 37, the second linear magnetic-field generating unit 210 includes a coil 233 extending in the y-axis direction in the reference coordinate axis, and formed so that a coil section becomes parallel to an xz-plane. Therefore, the second linear magnetic field formed by the coil 233 becomes a linear magnetic field at least in the subject 1, as shown in FIG. 37, and has a characteristic such that the strength gradually attenuates as the second linear magnetic field is away from the coil 233, that is, the position dependency regarding the strength.

The diffuse magnetic-field generating unit 211 includes a coil 234. The coil 233 is arranged so as to generate a magnetic field having a predetermined moving direction, and in the case of the ninth embodiment, the moving direction of the linear magnetic field generated by the coil 233 becomes the y-axis direction in the reference coordinate axis. The coil 234 is fixed at a position generating the same diffuse magnetic field as the magnetic field direction stored in a magnetic-field line orientation database 242.

Figure 38:
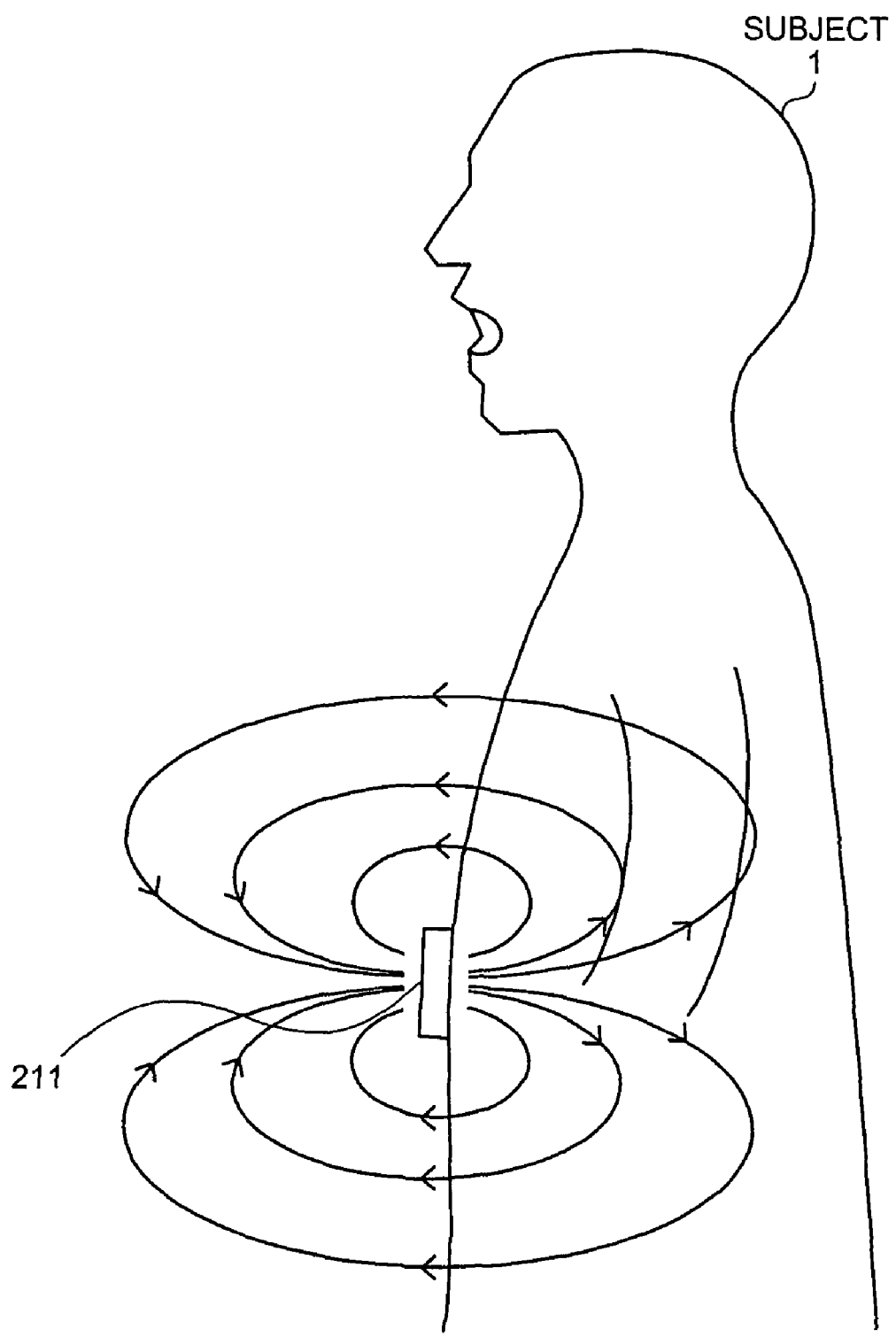
FIG. 38 is a schematic diagram of a mode of the diffuse magnetic field generated by the diffuse magnetic-field generating unit.

FIG. 38 is a schematic diagram of a mode of the diffuse magnetic field generated by the diffuse magnetic-field generating unit 211. As shown in FIG. 38, the coil 234 included in the diffuse magnetic-field generating unit 211 is formed in a coiled shape on the surface of the subject 1, and the diffuse magnetic field generated by the diffuse magnetic-field generating unit 211 is, as shown in FIG. 38, such that the magnetic-field line radially diffuses once and enters in the coil 234 again, in the magnetic field formed by the coil 34 (not shown in FIG. 38). The diffuse magnetic-field generating unit 211 is also arranged outside of the subject 1, to form a magnetic field radially. Accordingly, the formed diffuse magnetic field has a characteristic such that the strength gradually attenuates as the diffuse magnetic field is away from the coil 234.

Figure 39:
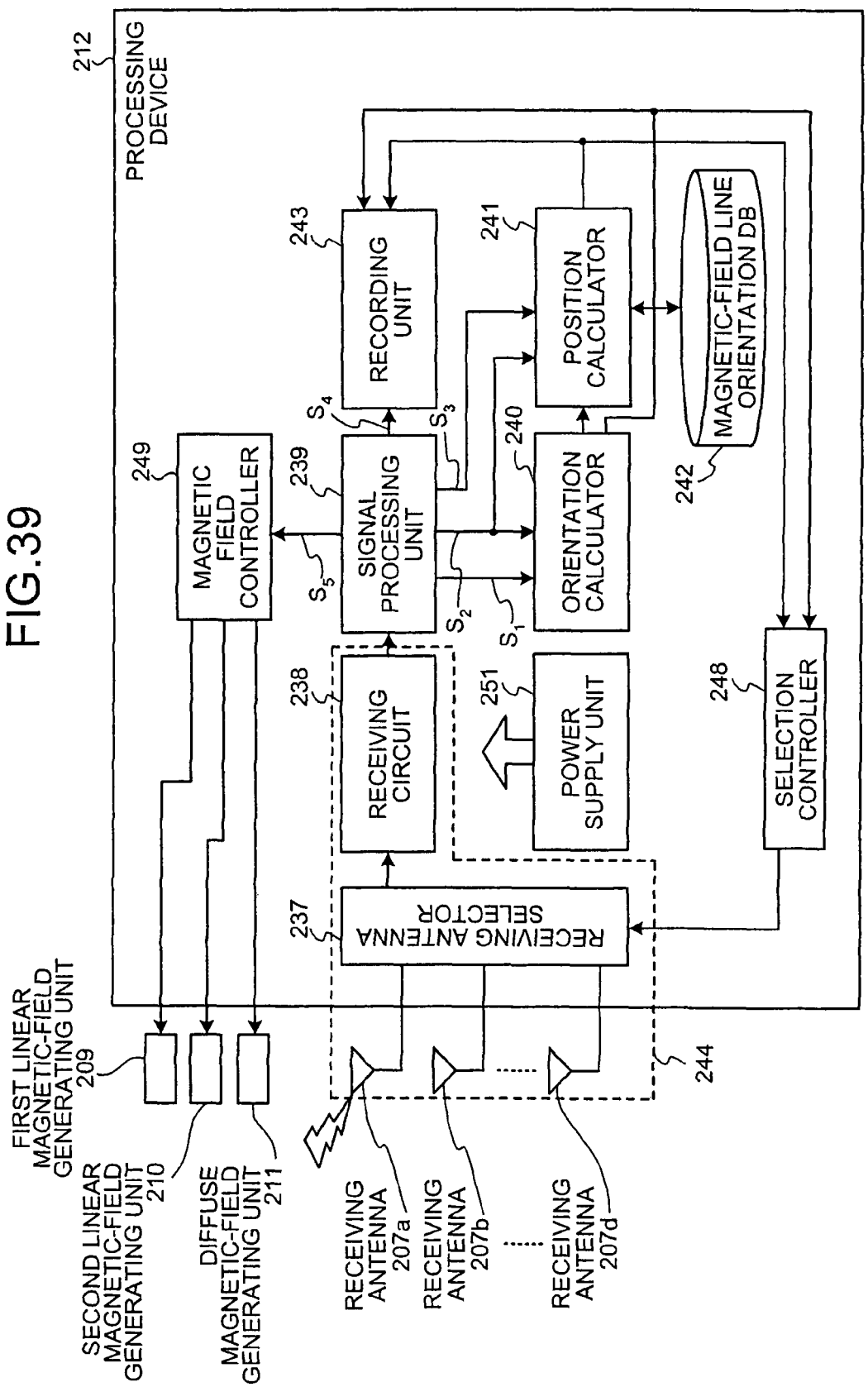
FIG. 39 is a schematic block diagram of a configuration of the processing device included in the position detecting apparatus.

The processing device 212 is explained next. FIG. 39 is a schematic block diagram of a configuration of the processing device 212. The processing device 212 has a function of performing receiving processing of the radio signal transmitted by the capsule endoscope 2. The processing device 212 has a receiving antenna selector 237 that selects any one of the receiving antennas 207a to 207d, a receiving circuit 238 that performs demodulation or the like with respect to the radio signal received via the selected receiving antenna to extract an original signal included in the radio signal, and a signal processing unit 239 that reconstructs an image signal and the like by processing the extracted original signal, corresponding to the function. Specifically, the signal processing unit 239 has a function of reconstructing the magnetic field signals $S_1$ to $S_3$, the image signal $S_4$, and the drive timing signal $S_5$ based on the extracted original signal, and outputting these signals to an appropriate component respectively. The magnetic field signals $S_1$ to $S_3$ correspond to the first linear magnetic field, the second magnetic field, and the diffusion magnetic field, respectively, detected by the magnetic field sensor 16. The image signal $S_4$ corresponds to the intra-subject image acquired by the intra-subject information acquiring unit 14, and the drive timing signal $S_5$ corresponds to the drive timing signal generated by the timing controller 21. Among these signals, the image signal $S_4$ reconstructed by the signal processing unit 239 is output to a recording unit 243. The recording unit 243 outputs input data to the portable recording medium 5, and has a function of recording results of position detection and the like (described later) as well as the image signal $S_4$ on the portable recording medium 5.

The processing device 212 also has a function of detecting the position of the capsule endoscope 2 in the subject 1 based on the magnetic field strength or the like detected by the capsule endoscope 2, and a function of detecting an orientation of the target coordinate axis fixed to the capsule endoscope 2 relative to the reference coordinate axis fixed to the subject 1. Specifically, the processing device 212 includes an orientation calculator 240 that calculates the orientation of the target coordinate axis relative to the reference coordinate axis based on the magnetic field signals $S_1$ and $S_2$ corresponding to the detected strength of the first linear magnetic field and the second linear magnetic field, of the signals transmitted by the capsule endoscope 2 and output by the signal processing unit 239, a position calculator 241 that calculates the position of the capsule endoscope 2 by using the magnetic field signal $S_3$ corresponding to the detected strength of the diffuse magnetic field, the magnetic field signal $S_2$, and a calculation result of the orientation calculator 240, and the magnetic-field line orientation database 242 in which the correspondence between the moving direction and the position of the magnetic-field line constituting the diffuse magnetic field is recorded at the time of calculating the position by the position calculator 241. Orientation calculation and position calculation by these components will be explained later in detail.

The processing device 212 includes a selection controller 248 that controls an antenna selection mode by the receiving antenna selector 237. The selection controller 248 has a function of selecting the receiving antenna 207 most suitable for the reception of the radio signal transmitted from the capsule endoscope 2, based on the orientation and position of the capsule endoscope 2, respectively, calculated by the orientation calculator 240 and the position calculator 241. The selection controller 248, the receiving circuit 238, and the receiving antennas 207a to 207d constitute a receiving unit 244, and the receiving unit 244 functions as an example of the receiver in the claims.

The processing device 212 has a function of controlling the drive timing of the first linear magnetic-field generating unit 209 and the like based on the driving timing signal extracted by the signal processing unit 239. Specifically, the processing device 212 includes a magnetic field controller 249 that controls the drive timing of the first linear magnetic-field generating unit 209, the second linear magnetic-field generating unit 210, and the diffuse magnetic-field generating unit 211 based on the drive timing signal $S_5$ output from the signal processing unit 239. The processing device 212 further includes a power supply unit 251 having a function of supplying drive power to the above components.

An operation of the body-insertable apparatus system according to the ninth embodiment is explained next. In the ninth embodiment, the processing device 212 performs predetermined processing with respect to an intermittently transmitted radio signal, corresponding to intermittent operations of acquisition of the intra-subject information, magnetic field detection, and radio transmission thereof repetitively performed by the capsule endoscope 2, while moving in the subject 1. Among these operations, a position detection operation using the magnetic field signal included in the radio signal repetitively transmitted from the capsule endoscope 2 is first explained, and thereafter, control processing of the drive timing of the radio transmitting unit 19 that transmits the radio signal, performed on the capsule endoscope 2 side will be explained.

The position detection operation is explained first. The body-insertable apparatus system according to the ninth embodiment has a configuration in which the position relationship between the reference coordinate axis fixed to the subject 1 and the target coordinate axis fixed to the capsule endoscope 2 is calculated. Specifically, the orientation of the target coordinate axis relative to the reference coordinate axis is calculated, and the position of the origin of the target coordinate axis on the reference coordinate axis, that is, the position of the capsule endoscope 2 inside the subject 1 is then calculated by using the calculated orientation. Therefore, the orientation calculation mechanism is first explained below, and the position calculation mechanism using the calculated orientation is explained next. However, of course, an application of the present invention is not limited to the system having the position detection mechanism.

The orientation calculation mechanism performed by the orientation calculator 240 is explained. Since the orientation calculation mechanism is the same as that performed by the orientation calculator 40 explained with reference to FIG. 7, explanation is made with reference to FIG. 7. As explained above, the capsule endoscope 2 is rotating by a predetermined angle, designating the moving direction as an axis, while moving along the passage route in the subject 1. Accordingly, the target coordinate axis fixed to the capsule endoscope 2 generates a deviation of the orientation as shown in FIG. 7, relative to the reference coordinate axis fixed to the subject 1.

On the other hand, the first linear magnetic-field generating unit 209 and the second linear magnetic-field generating unit 210 are fixed, respectively, relative to the subject 1. Therefore, the first and the second linear magnetic fields generated by the first linear magnetic-field generating unit 209 and the second linear magnetic-field generating unit 210 travel in a fixed direction relative to the reference coordinate axis, more specifically, the first linear magnetic field travels in the z-axis direction, and the second linear magnetic field when the second linear magnetic-field generating unit 210 is used travels in the y-axis direction in the reference coordinate axis.

Orientation calculation in the ninth embodiment is performed by using the first linear magnetic field and the second linear magnetic field. Specifically, the moving direction of the first linear magnetic field and the second linear magnetic field supplied in a time sharing manner is detected by the magnetic field sensor 16 included in the capsule endoscope 2. The magnetic field sensor 16 is configured so as to detect the magnetic field components in the X-axis direction, the Y-axis direction, and the Z-axis direction in the target coordinate axis, and information of the moving direction of the detected first and second linear magnetic fields in the target coordinate axis is transmitted to the position detecting apparatus 3 via the radio transmitting unit 19.

The radio signal transmitted by the capsule endoscope 2 is output as magnetic field signals $S_1$ and $S_2$ through the processing by the signal processing unit 239 and the like. For example, in the example shown in FIG. 7, the magnetic field signal $S_1$ includes information of the coordinate $(X_1, Y_1, Z_1)$ as the moving direction of the first linear magnetic field, and the magnetic field signal $S_2$ includes information of the coordinate $(X_2, Y_2, Z_2)$ as the moving direction of the second linear magnetic field. On the other hand, the orientation calculator 240 calculates the orientation of the target coordinate axis relative to the reference coordinate axis, upon reception of inputs of these magnetic field signals $S_1$ and $S_2$. Specifically, the orientation calculator 240 ascertains that a coordinate $(X_3, Y_3, Z_3)$ in which a value of an inner product with respect to both $(X_1, Y_1, Z_1)$ and $(X_2, Y_2, Z_2)$ in the target coordinate axis becomes zero corresponds to the direction of the z-axis in the reference coordinate axis. The orientation calculator 240 then performs predetermined coordinate conversion processing based on the above correspondence, to calculate the coordinate in the reference coordinate axis of the X-axis, the Y-axis, and the Z-axis in the target coordinate axis, and outputs such a coordinate as the orientation information. This is the orientation calculation mechanism by the orientation calculator 240.

The position calculation mechanism of the capsule endoscope 2 by the position calculator 241 using the calculated orientation information is explained next. The position calculator 241 has a configuration such that magnetic field signals $S_2$ and $S_3$ are input from the signal processing unit 239, the orientation information is input from the orientation calculator 240, and information stored in the magnetic-field line orientation database 242 is input. The position calculator 241 calculates the position of the capsule endoscope 2 in the following manner, based on these pieces of input information.

Figure 40:
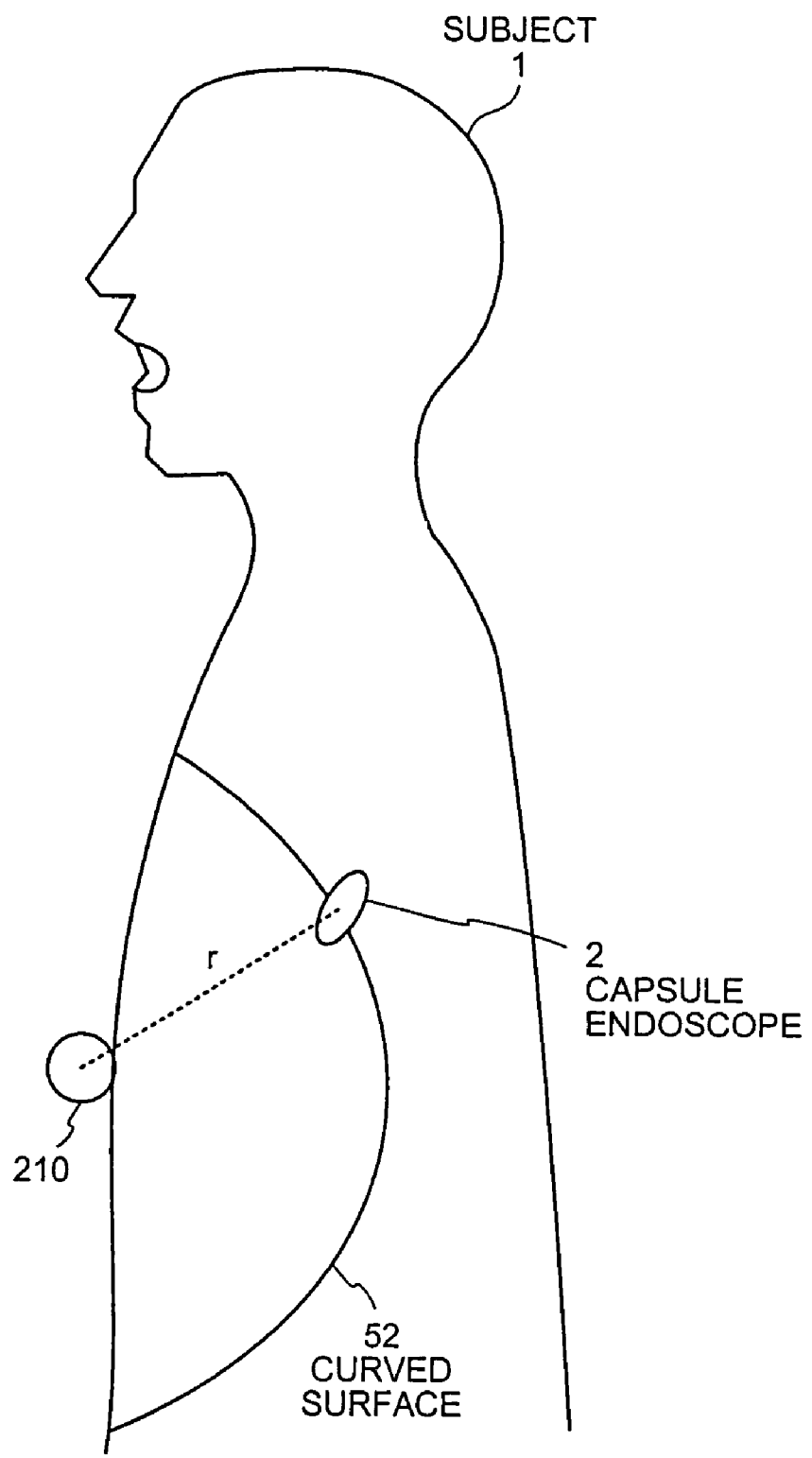
FIG. 40 is a schematic diagram of a use mode of the second linear magnetic field at the time of position calculation.

At first, the position calculator 241 calculates the distance between the second linear magnetic-field generating unit 210 and the capsule endoscope 2 by using the magnetic field signal $S_2$. The magnetic field signal $S_2$ corresponds to the detection result of the second linear magnetic field in the area where the capsule endoscope 2 is present. The second linear magnetic field has a such characteristic that the strength thereof gradually attenuates as the second linear magnetic field is away from the second linear magnetic-field generating unit 210, corresponding to the second linear magnetic-field generating unit 210 being arranged outside of the subject 1. By using such a characteristic, the position calculator 241 compares the strength of the second linear magnetic field near the second linear magnetic-field generating unit 210 (obtained from a current value of the current allowed to flow to the second linear magnetic-field generating unit 210) with the strength of the second linear magnetic field in the area where the capsule endoscope 2 is present obtained from the magnetic field signal $S_2$, to calculate a distance r between the second linear magnetic-field generating unit 210 and the capsule endoscope 2. As a result of calculation of the distance r, as shown in FIG. 40, it becomes obvious that the capsule endoscope 2 is positioned on a curved surface 52, which is an aggregate of points away from the second linear magnetic-field generating unit 210 by the distance r.

Figure 41:
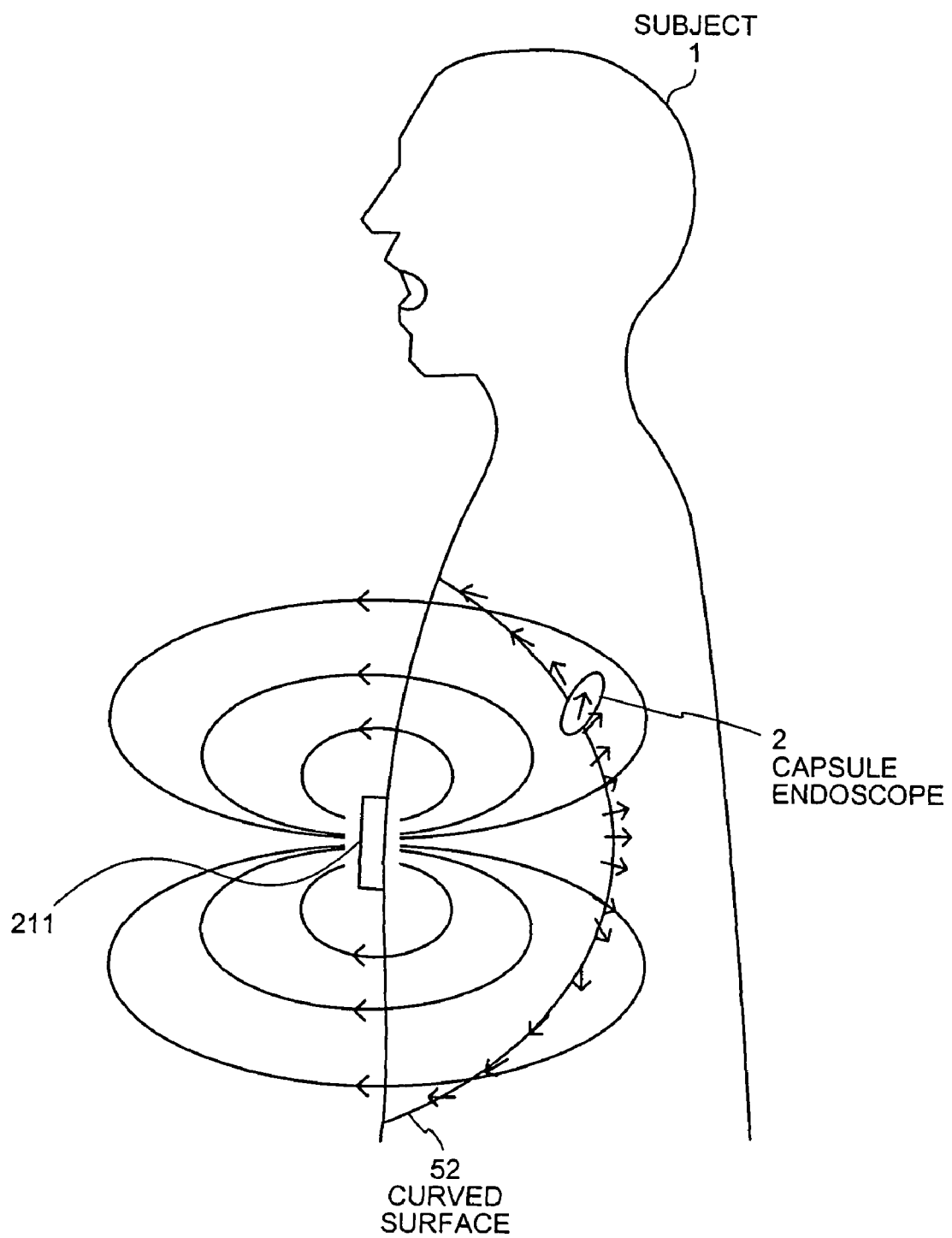
FIG. 41 is a schematic diagram of a use mode of the diffuse magnetic field at the time of position calculation.

The position calculator 241 then calculates the position of the capsule endoscope 2 on the curved surface 52 based on the magnetic field signal $S_3$, the orientation information calculated by the orientation calculator 240, and the information stored in the magnetic-field line orientation database 42. Specifically, the moving direction of the diffuse magnetic field at the present position of the capsule endoscope 2 is calculated based on the magnetic field signal $S_3$ and the orientation information. Since the magnetic field signal $S_3$ is a signal corresponding to the detection result of the diffuse magnetic field based on the target coordinate axis, the moving direction of the diffuse magnetic field in the reference coordinate axis at the present position of the capsule endoscope 2 is calculated, by applying the coordinate conversion processing from the target coordinate axis to the reference coordinate axis by using the orientation information, with respect to the moving direction of the diffuse magnetic field based on the magnetic field signal $S_3$. The magnetic-field line orientation database 242 stores the correspondence between the moving direction and the position of the diffuse magnetic field in the reference coordinate axis. Therefore, the position calculator 241 calculates, as shown in FIG. 41, the position corresponding to the moving direction of the diffuse magnetic field calculated by referring to the information stored in the magnetic-field line orientation database 242, and specifies the calculated position as the position of the capsule endoscope 2. By performing the above processing, the orientation and the position of the capsule endoscope 2 in the subject 1 are calculated, to complete the position detection.

The above position detection operation is repetitively performed accompanying the reception of the radio signal repetitively transmitted from the capsule endoscope 2. The detected orientation and position of the capsule endoscope 2 are recorded on the portable recording medium 5 via the recording unit 243, and used at the time of diagnosis by a doctor or the like, together with the recorded image data.

Figure 42:
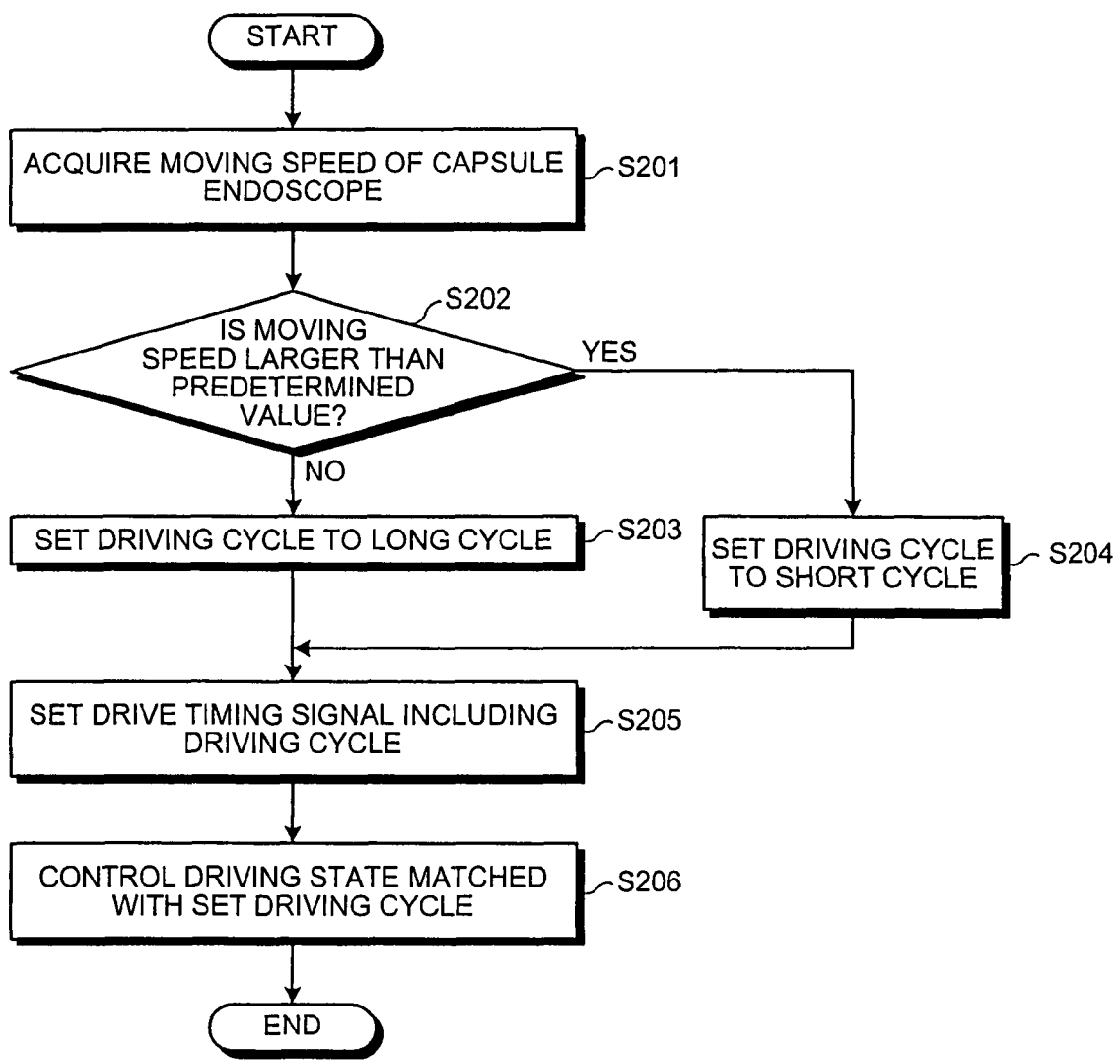
FIG. 42 is a flowchart for explaining processing in a timing controller included in the capsule endoscope.

Control processing of the drive timing of the radio transmitting unit 19 that transmits the radio signal, performed on the capsule endoscope 2 side, is explained next. FIG. 42 is a flowchart for explaining control processing of the drive timing performed by the timing controller 21 included in the capsule endoscope 2.

As shown in FIG. 42, the timing controller 21 acquires the moving speed of the capsule endoscope 2 calculated by the speed calculator 228 (step S201), and determines whether the acquired moving speed is larger than a predetermined threshold (step S202). When the acquired moving speed is smaller than the predetermined threshold (step S202, No), the timing controller 21 sets a driving cycle to a predetermined long cycle (step S203). On the other hand, when the acquired moving speed is larger than the predetermined threshold (step S202, Yes), the timing controller 21 sets a driving cycle to a predetermined short cycle shorter than the long cycle (step S204). Thereafter, the timing controller 21 generates a drive timing signal including at least information of the set driving cycle (step S205), and drives the intra-subject information acquiring unit 14, the magnetic field sensor 16, and the radio transmitting unit 19 at a drive timing according to the set driving cycle (step S206).

In the ninth embodiment, the magnetic field controller 249 controls the magnetic-field generation timing by the second linear magnetic-field generating unit 210 and the diffuse magnetic-field generating unit 211 so as to synchronize with the drive timing set by the timing controller 21. In other words, the magnetic field controller 249 calculates the driving cycle based on the drive timing signal generated by the timing controller 21 and reconstructed by the signal processing unit 239, and controls so that the first linear magnetic-field generating unit 209, the second linear magnetic-field generating unit 210, and the diffuse magnetic-field generating unit 211 are driven at the timing corresponding to the calculated driving cycle. Specifically, the magnetic field controller 249 controls the drive timing of the first linear magnetic-field generating unit 209 and the like by controlling the feed timing of the drive power held by the power supply unit 251.

An advantage of the body-insertable apparatus system according to the ninth embodiment is explained below. The body-insertable apparatus system according to the ninth embodiment has such a configuration that the drive timing of the radio transmitting unit 19, the magnetic field sensor 16, and the intra-subject information acquiring unit 14 are controlled based on the moving state of the capsule endoscope 2. In the ninth embodiment, therefore, there is an advantage in that the drive timing of the radio transmitting unit 19 and the like can be optimized relative to the moving state of the capsule endoscope 2.

For example, in the ninth embodiment, control by using the moving speed of the capsule endoscope 2 as the moving state is performed. Specifically, the timing controller 21 sets the driving cycle to a short cycle when the moving speed is high, and to a long cycle when the moving speed is low, and controls the radio transmitting unit 19 and the like so as to operate at the drive timing corresponding to the set driving cycle. Therefore, when the moving speed of the capsule endoscope 2 is low, the frequency of transmission and the like of the radio signal decreases, thereby providing an advantage in that useless operations of the capsule endoscope 2 can be reduced.

Generally, when the capsule endoscope 2 moves at a low speed, the moving distance of the capsule endoscope 2 per unit time decreases. Therefore, the first linear magnetic field and the like detected by the magnetic field sensor 16 have substantially the same direction and strength in the short cycle, and hence the necessity for driving the magnetic field sensor 16 and the like with a short cycle is little. In the ninth embodiment, therefore, when the moving speed of the capsule endoscope 2 is low, the driving cycle is set to the long cycle, so that detection of the similar magnetic field and transmission of the radio signal including the similar information of the magnetic field are repeated over a plurality of times can be avoided, thereby reducing useless operations of the capsule endoscope 2.

By adopting such a configuration, there are advantages in that complication of processing in the whole body-insertable apparatus system can be avoided, and the power consumption in the capsule endoscope 2 can be reduced. The capsule endoscope 2 generally has such a configuration that it is driven by limited power supplied by a small primary battery, since the battery is housed in the capsule. Accordingly, there is a limitation in the power usable by the capsule endoscope 2, and such an advantage that the power consumption generated by useless operations can be avoided by adopting the configuration of the ninth embodiment is remarkable.

In the flowchart shown in FIG. 42, the magnitude correlation with the predetermined threshold is calculated at step S202, and two cycles are set according to the magnitude correlation. However, an optional cycle-setting algorithm can be used, so long as the driving cycle is determined based on the moving speed. Specifically, when a product of the moving speed and the driving cycle is set substantially to a constant value, transmission or the like of the radio signal is performed every time the capsule endoscope 2 moves substantially the same distance, regardless of the moving speed. Accordingly, the power consumption of the capsule endoscope 2 can be reduced, while enabling effective detection of a change of the position of the capsule endoscope 2.

Further, in the ninth embodiment, there is an advantage in that the power consumption of the capsule endoscope 2 can be reduced. That is, the magnetic field controller 249 included in the processing device 212 constituting the position detecting apparatus 203 has a function of controlling the driving state of the first linear magnetic-field generating unit 209 and the like based on the drive timing signal. Specifically, the magnetic field controller 249 performs control based on the drive timing signal generated by the timing controller 21 included in the capsule endoscope 2, thereby enabling to drive the first linear magnetic-field generating unit 209, the second linear magnetic-field generating unit 210, and the diffuse magnetic-field generating unit 211 only at the timing when the magnetic field sensor 16 detects the magnetic field. As described above, the first linear magnetic-field generating unit 209 and the like have a function of generating the magnetic field based on the power supplied by the power supply unit 251 included in the processing device 212. Therefore, by optimizing the drive timing matched with the driving cycle of the magnetic field sensor 16, the power consumption of the power supply unit 251 can be reduced, as compared to a case in which the magnetic field is generated over all the periods as in the conventional system.

A modification of the body-insertable apparatus system according to the ninth embodiment is explained next. In the body-insertable apparatus system according to this modification, a vibrational state of the capsule endoscope is detected as the moving state of the capsule endoscope, to perform drive timing control based on the vibrational state.

Figure 43:
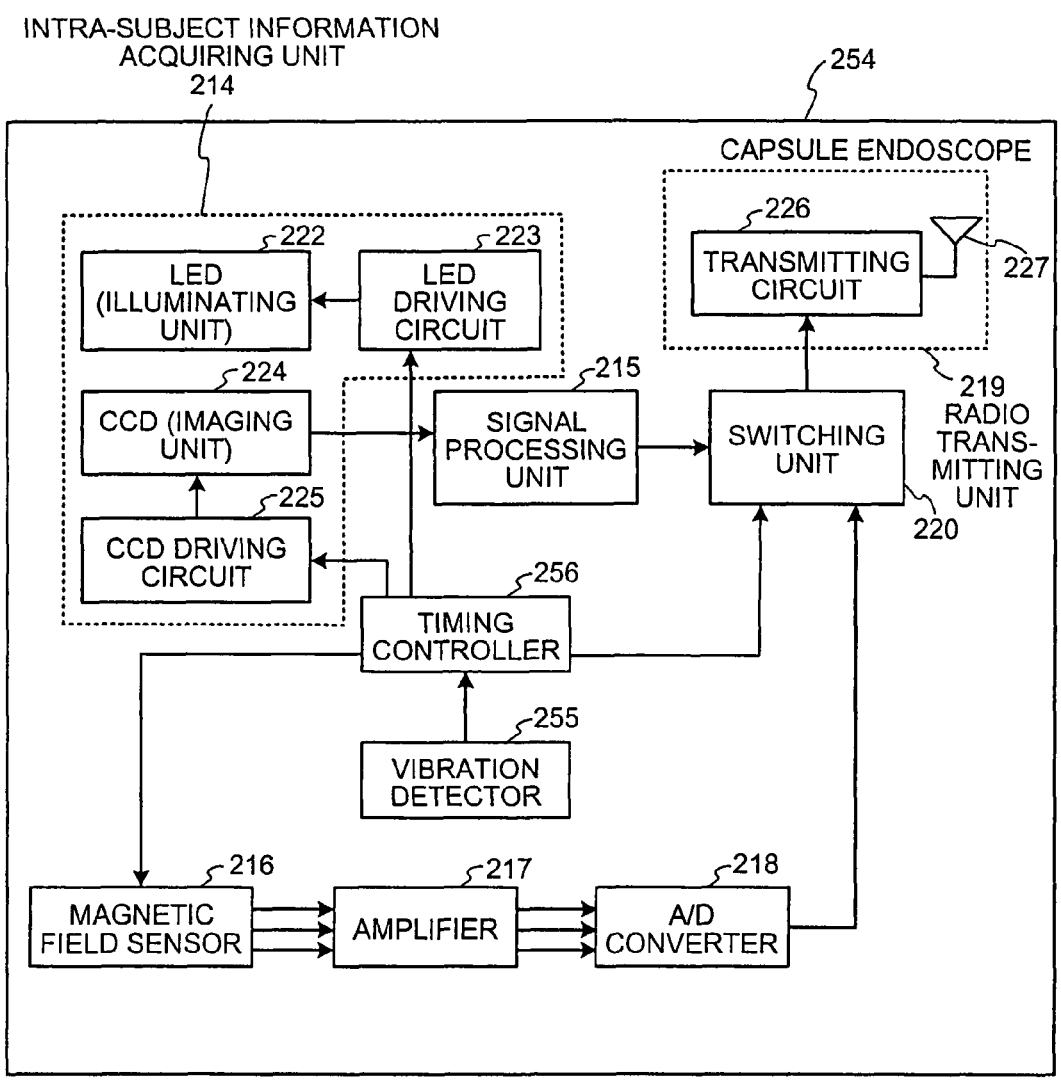
FIG. 43 is a schematic block diagram of a configuration of the capsule endoscope in a modification of the ninth embodiment.

FIG. 43 is a schematic block diagram of the configuration of a capsule endoscope 254 constituting the modification. As shown in FIG. 43, in the modification, a vibration detector 255 is newly provided instead of the speed detector, and a timing controller 256 controls the drive timing based on the detection result of the vibration detector 255.

The vibration detector 255 detects the moving state of the capsule endoscope 254 like the speed calculator 228 in the ninth embodiment, and detects the vibrational state of the capsule endoscope 254 as the moving state. Specifically, the vibration detector 255 is formed of an acceleration sensor, a cantilever, and the like and has a function of detecting the vibrational state of the capsule endoscope 254. The "vibrational state" is a wide concept indicating a state in which the capsule endoscope moves at an acceleration of a certain threshold or higher, and is not limited to a single vibratory motion.

An advantage of this modification is explained. In this modification, the vibrational state is used as the moving state of the capsule endoscope 254, and for example, when the capsule endoscope 254 stops in the subject 1, the timing controller 256 can set the driving cycle infinite (that is, the function of the magnetic field sensor 216 and the like is temporarily stopped). Therefore, it can be prevented that the magnetic field sensor 216 is uselessly driven at the time of stopping (that is, in the period when the position does not change). As a result, the power consumption can be reduced.

Further, in this modification, at the time of position detection, the orientation of the capsule endoscope 254 is calculated by the orientation calculator 240, as in the ninth embodiment, and there can be a case in which the capsule endoscope 254 changes the orientation while staying in a predetermined region (that is, in a state in which the moving speed is zero). In the modification, since the body-insertable apparatus system has a function of controlling the drive timing by detecting the vibration, when the capsule endoscope 254 changes the orientation while maintaining the zero moving speed, the capsule endoscope 254 can operate at predetermined driving timing. As a result, there is an advantage in that position detection (particularly, orientation detection) can be reliably performed also in such a case.

A body-insertable apparatus system according to a tenth embodiment is explained next. In the body-insertable apparatus system according to the tenth embodiment, the moving state of the capsule endoscope is calculated on the position detecting apparatus side, and information of the calculated moving state is wirelessly transmitted to the capsule endoscope. In the following explanation, parts denoted by like reference numerals or names as in the ninth embodiment have like structures and functions as in the ninth embodiment, unless otherwise specified.

Figure 44:
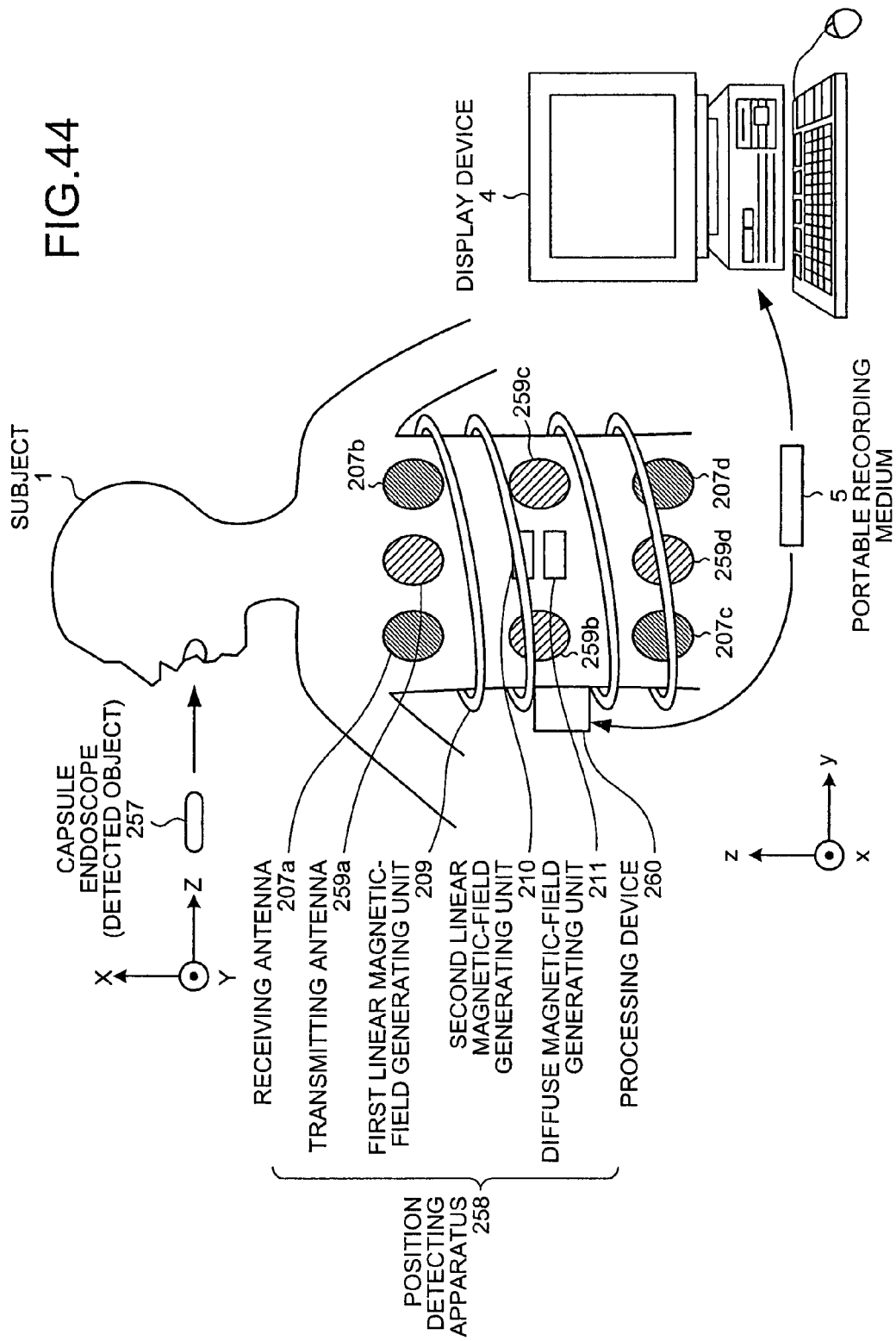
FIG. 44 is a schematic diagram of an overall configuration of a body-insertable apparatus system according to a tenth embodiment.

FIG. 44 is a schematic diagram of an overall configuration of the body-insertable apparatus system according to the tenth embodiment. As shown in FIG. 44, the body-insertable apparatus system according to the tenth embodiment basically has the same configuration as that of the ninth embodiment. On the other hand, the position detecting apparatus 258 newly includes receiving antennas 259a to 259d.

Figure 45:
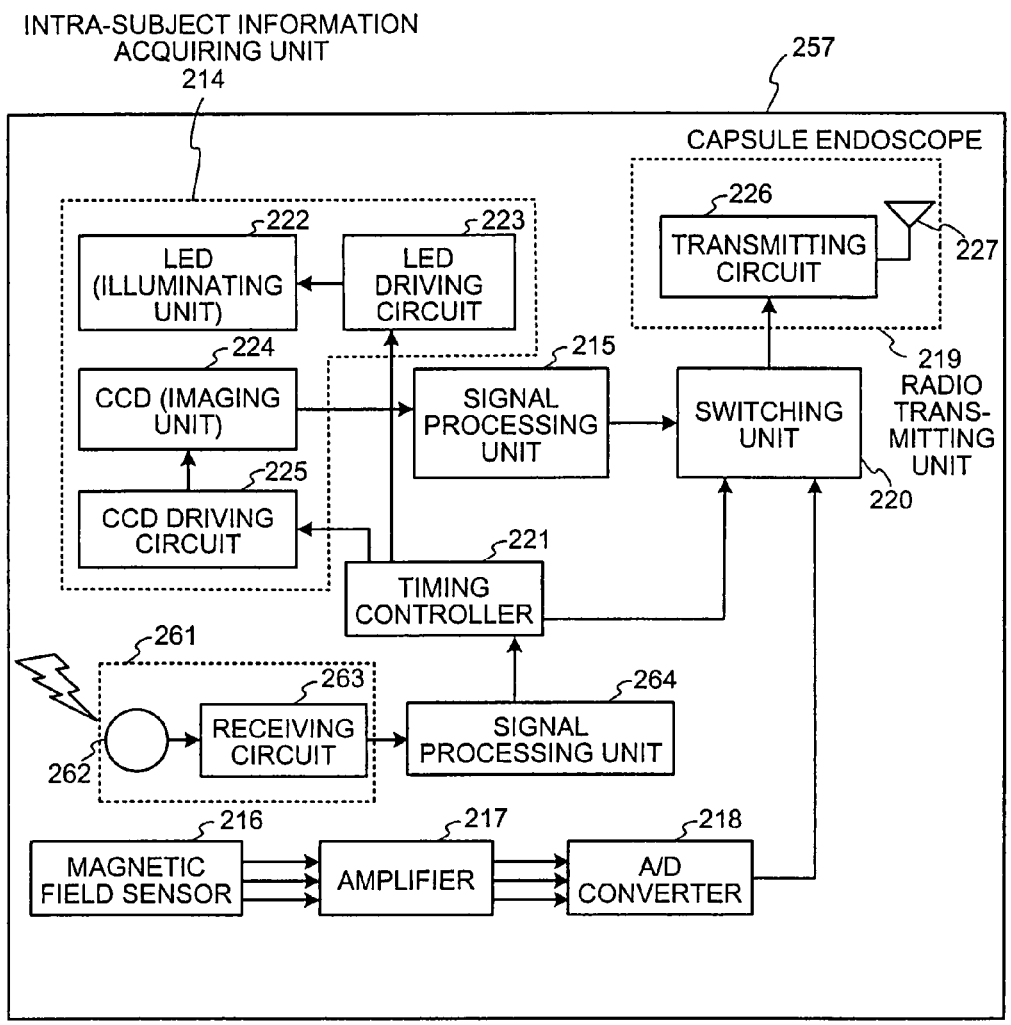
FIG. 45 is a schematic block diagram of a configuration of the capsule endoscope included in the body-insertable apparatus system.

A capsule endoscope 257 constituting the body-insertable apparatus system according to the tenth embodiment is explained. FIG. 45 is a schematic block diagram of a configuration of the capsule endoscope 257. As shown in FIG. 45, the capsule endoscope 257 basically has the same configuration as the capsule endoscope 2 in the ninth embodiment. On the other hand, the capsule endoscope 257 newly includes a radio receiving unit 261 that performs receiving processing of the radio signal transmitted from the position detecting apparatus 258 and a signal processing unit 264 for extracting the moving speed of the capsule endoscope 257 from the signal processed by the radio receiving unit 261.

The radio receiving unit 261 receives the radio signal transmitted from the position detecting apparatus 258, and performs the receiving processing for extracting a predetermined original signal by performing demodulation or the like. Specifically, the radio receiving unit 261 includes a receiving antenna 262 for receiving the radio signal and a receiving circuit 263 that performs the receiving processing such as demodulation with respect to the radio signal received via the receiving antenna 262.

The signal processing unit 264 reconstructs the information included in the radio signal based on the original signal extracted from the radio signal by the radio receiving unit 261. In the tenth embodiment, the information of the moving speed of the capsule endoscope 257 is included in the radio signal transmitted from the position detecting apparatus 258, and the signal processing unit 264 has a function of extracting the information of the moving speed of the capsule endoscope 257 and outputting the information to a timing controller 221.

Figure 46:
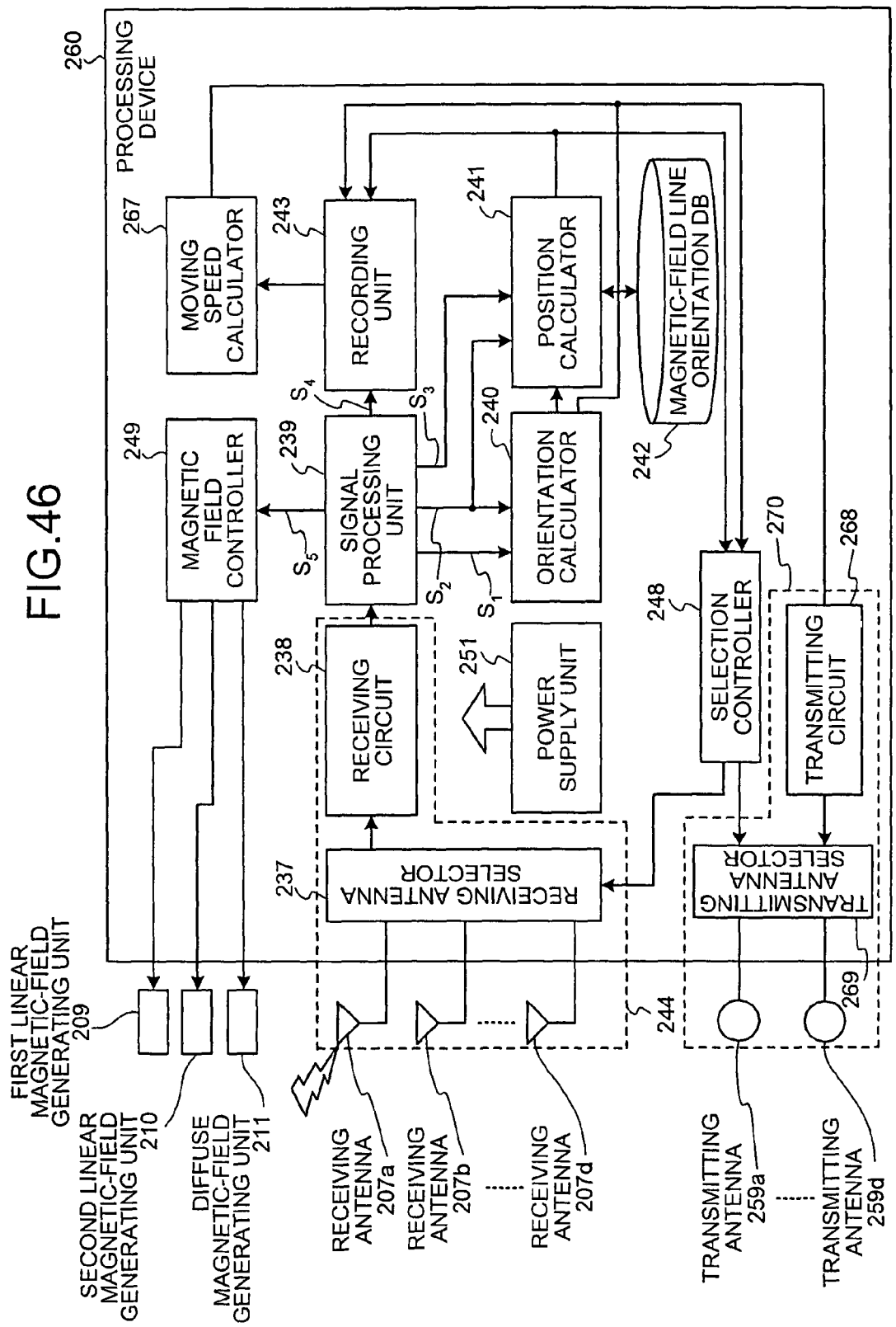
FIG. 46 is a schematic block diagram of a configuration of the processing device included in the body-insertable apparatus system.

A configuration of the processing device 260 included in the position detecting apparatus 258 is explained. FIG. 46 is a schematic block diagram of the configuration of the processing device 260. As shown in FIG. 46, the processing device 260 basically has the same configuration as the processing device 212 in the ninth embodiment. On the other hand, the processing device 260 further includes a moving speed calculator 267 that calculates the moving speed of the capsule endoscope 257 based on the information recorded in the recording unit 243, a transmitting circuit 268 that generates a radio signal including the information of the moving speed, and a transmitting antenna selector 269 that selects an antenna that transmits the radio signal generated by the transmitting circuit 268.

The moving speed calculator 267 calculates the moving speed of the capsule endoscope 257 based on past position detection results of the capsule endoscope 257. Specifically, the recording unit 243 has a function of recording the positions of the capsule endoscope 257 calculated by the position calculator 241 regarding a plurality of time instants, as is explained in the ninth embodiment. The moving speed calculator 267 acquires information relating to the positions of the capsule endoscope 257 at the past time instants recorded in the recording unit 243 and the time at which the position was calculated, thereby calculating the moving speed of the capsule endoscope 257. Specifically, for example, it is assumed here that the capsule endoscope 257 is positioned at a coordinate $(x_1, y_1, z_1)$ at time instant $t_1$, and positioned at a coordinate $(x_2, y_2, z_2)$ at time instant $t_2$ after time has passed by $\Delta t$ since time instant $t_1$. The moving speed v can be defined as follows by using these pieces of information:

$$v = \{(x_2-x_1)^2 + (y_2-y_1)^2 + (z_2-z_1)^2\}^{1/2}/\Delta t \qquad (2)$$

The transmitting circuit 268 generates the radio signal including the information of the moving speed calculated by the moving speed calculator 267. Specifically, the transmitting circuit 268 generates the radio signal by performing necessary processing such as modulation processing.

The transmitting antenna selector 269 selects a transmitting antenna most suitable for the transmission of the radio signal, from the transmitting antennas 259a to 259d arranged in a plurality of numbers. Specifically, like the receiving antenna selector 237, the transmitting antenna selector 269 has a function of selecting a transmitting antenna from the transmitting antennas 259a to 259d under the control of the selection controller 248. The transmitting circuit 268, the transmitting antenna selector 269, and the transmitting antennas 259a to 259d constitute a transmitting unit 270.

An advantage of the body-insertable apparatus system according to the tenth embodiment is explained next. The body-insertable apparatus system according to the tenth embodiment has such a configuration that the drive timing of the magnetic field sensor 216 included in the capsule endoscope 257 is controlled corresponding to the moving speed of the capsule endoscope 257 as in the ninth embodiment, and the magnetic field generation timing of the first linear magnetic-field generating unit 209 included in the position detecting apparatus 258. Therefore, as in the ninth embodiment, it is suppressed that useless operations are made in the capsule endoscope 257 or the like, thereby reducing the power consumption.

The tenth embodiment has a configuration such that the moving speed of the capsule endoscope 257 is detected by the moving speed calculator 267 included in the processing device 260, and by adopting such a configuration, a new advantage is provided. The tenth embodiment has an advantage such that the capsule endoscope 257 does not need to include a speed calculator inside thereof, thereby preventing the capsule endoscope 257 from being large-sized.

A body-insertable apparatus system according to an eleventh embodiment is explained next. The body-insertable apparatus system according to the eleventh embodiment has a function of performing position detection by using the earth magnetism, instead of the first linear magnetic field.

Figure 47:
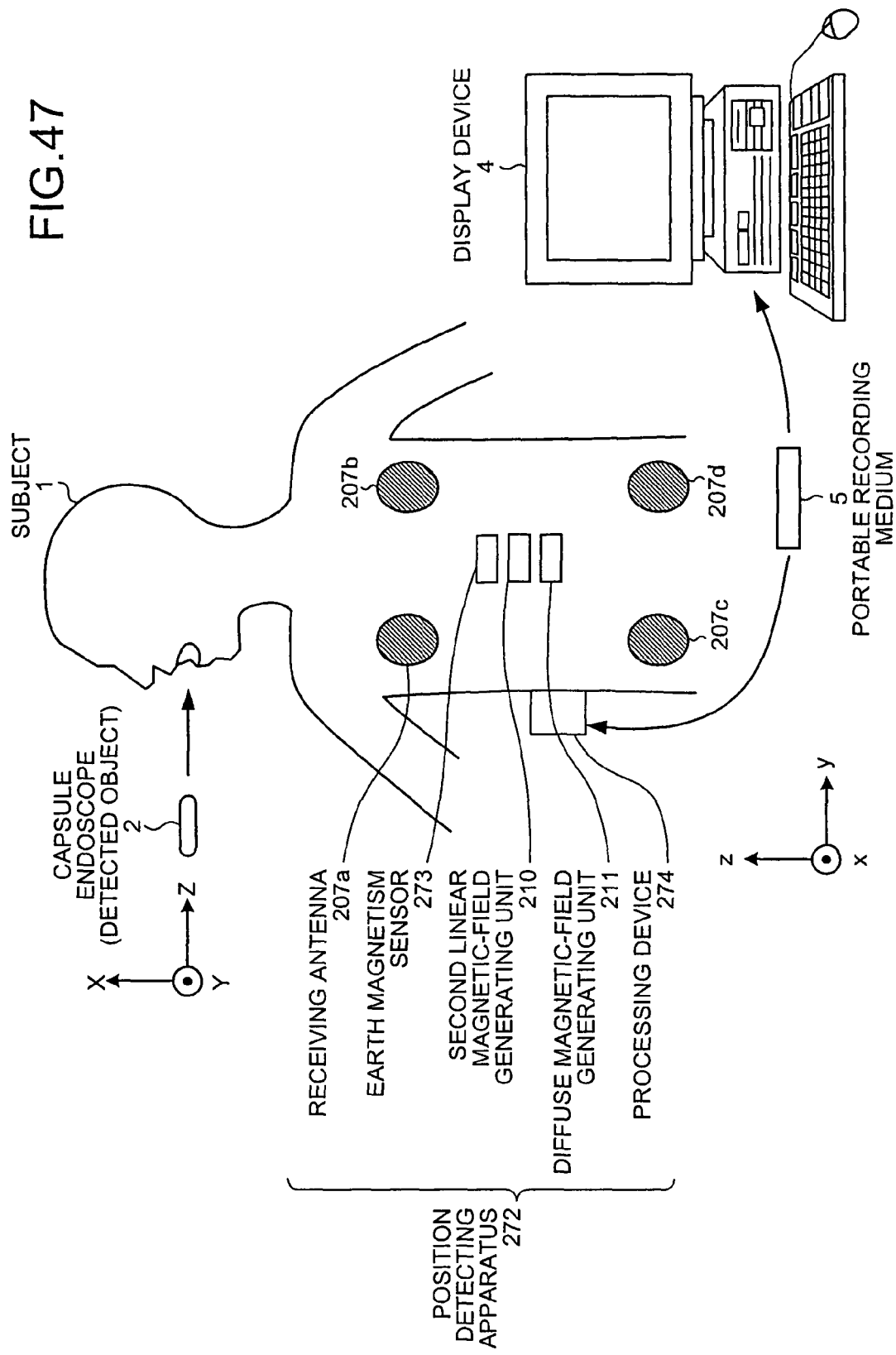
FIG. 47 is a schematic diagram of an overall configuration of a body-insertable apparatus system according to an eleventh embodiment.

FIG. 47 is a schematic diagram of an overall configuration of the body-insertable apparatus system according to the eleventh embodiment. As shown in FIG. 47, the body-insertable apparatus system according to the eleventh embodiment includes the capsule endoscope 2, the display device 4, and the portable recording medium 5 as in the ninth embodiment, while the configuration of the position detecting apparatus 272 is different. Specifically, the first linear magnetic-field generating unit 209 included in the position detecting apparatus in the ninth embodiment is omitted, and an earth magnetism sensor 273 is newly included. The processing device 274 also has a different configuration from the ninth embodiment.

The earth magnetism sensor 273 basically has the same configuration as that of the magnetic field sensor 16 included in the capsule endoscope 2. That is, the earth magnetism sensor 273 detects the strength of the magnetic field components in predetermined three axial directions in an area where it is arranged, and outputs an electric signal corresponding to the detected magnetic field strength. On the other hand, the earth magnetism sensor 273 is arranged on the body surface of the subject 1, which is different from the magnetic field sensor 16, and detects the strength of the magnetic field components respectively corresponding to the x-axis, y-axis, and z-axis directions in the reference coordinate axis fixed to the subject 1. In other words, the earth magnetism sensor 273 has a function of detecting the moving direction of the earth magnetism, and outputs the electric signal corresponding to the magnetic field strength detected for the x-axis direction, the y-axis direction, and the z-axis direction to the processing device 274.

Figure 48:
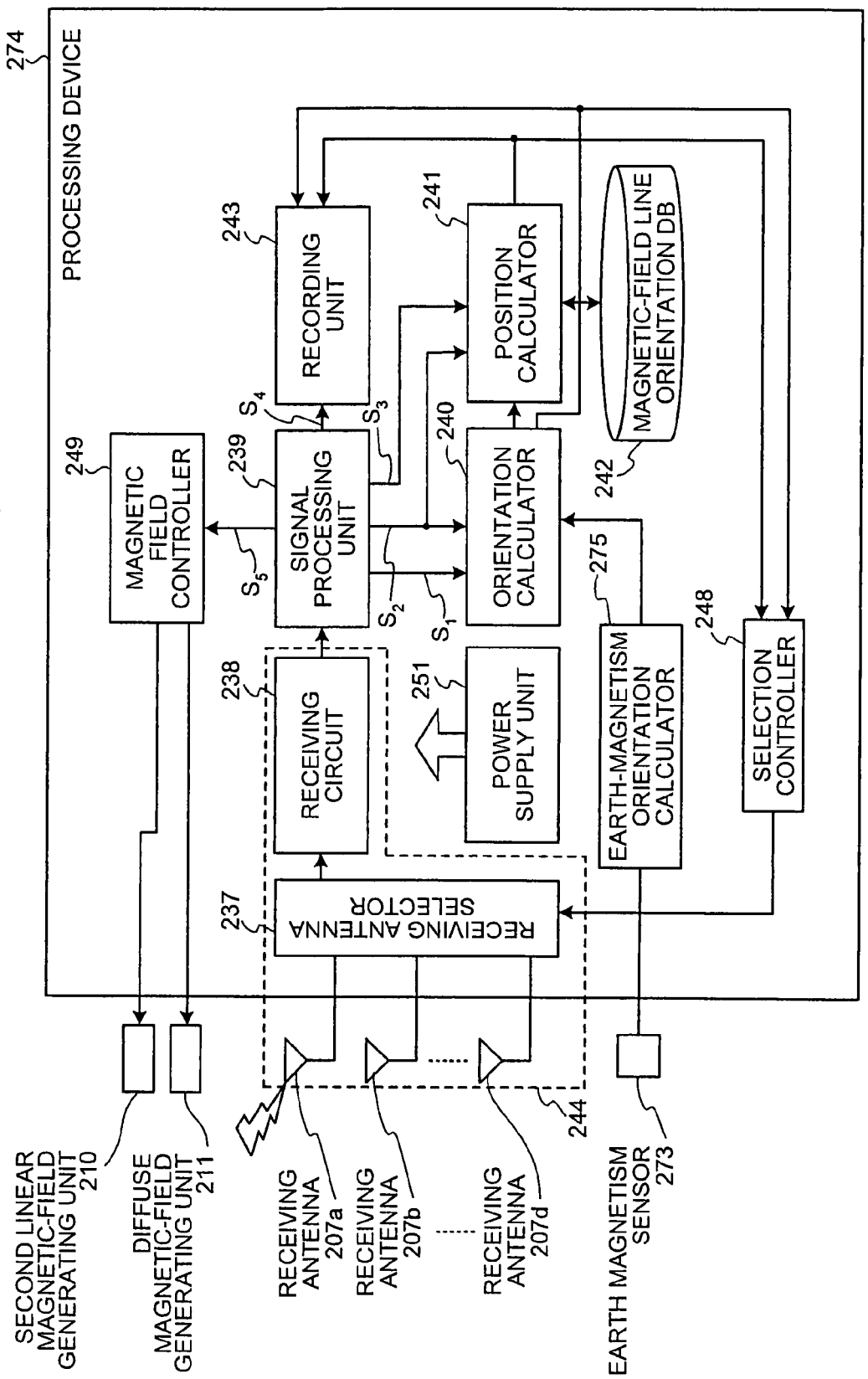
FIG. 48 is a schematic block diagram of a configuration of the processing device included in the body-insertable apparatus system.

The processing device 274 in the eleventh embodiment is explained. FIG. 48 is a block diagram of a configuration of the processing device 274. As shown in FIG. 48, the processing device 274 basically has the same configuration as that of the processing device 212 in the ninth embodiment. On the other hand, the processing device 274 includes an earth-magnetism orientation calculator 275 that calculates the moving direction of the earth magnetism on the reference coordinate axis based on the electric signal input from the earth magnetism sensor 273, and outputs the calculation result to the orientation calculator 240.

There is a problem in calculation of the moving direction of the earth magnetism on the reference coordinate axis fixed to the subject 1, when the earth magnetism is used as the first linear magnetic field. That is, since the subject 1 can freely move while the capsule endoscope 2 is moving in the body, it is predicted that the position relationship between the reference coordinate axis fixed to the subject 1 and the earth magnetism changes with the movement of the subject 1. On the other hand, from a standpoint of calculating the position of the target coordinate axis relative to the reference coordinate axis, when the moving direction of the first linear magnetic field on the reference coordinate axis becomes unclear, there is a problem in that the correspondence between the reference coordinate axis and the target coordinate axis cannot be clarified relating to the moving direction of the first linear magnetic field.

Accordingly, in the eleventh embodiment, the earth magnetism sensor 273 and the earth-magnetism orientation calculator 275 are provided for monitoring the moving direction of the earth magnetism, which will change on the reference coordinate axis due to movement or the like of the subject 1. In other words, the earth-magnetism orientation calculator 275 calculates the moving direction of the earth magnetism on the reference coordinate axis based on the detection result of the earth magnetism sensor 273, and outputs the calculation result to the orientation calculator 240. On the other hand, the orientation calculator 240 can calculate the correspondence between the reference coordinate axis and the target coordinate axis relating to the moving direction of the earth magnetism, by using the input moving direction of the earth magnetism, and the calculated correspondence is used together with the correspondence in the second linear magnetic field to calculate the orientation information.

The moving directions of the earth magnetism and the second linear magnetic field generated by the second linear magnetic-field generating unit 210 can be parallel to each other, depending on the direction of the subject 1. In this case, the position relationship can be detected by also using data relating to the orientation of the target coordinate axis at the time immediately before and the position of the origin. Further, to avoid that the moving directions of the earth magnetism and the second linear magnetic field become parallel to each other, it is also effective to have such a configuration that the extending direction of the coil 234 constituting the second linear magnetic-field generating unit 210 is not set to the y-axis direction in the reference coordinate axis, as shown in FIG. 3, but for example, set to the z-axis direction. Alternatively, the position detecting apparatus 272 may further include a sub-linear magnetic-field generating unit and a magnetic-field controller so that the moving directions of the earth magnetism and linear magnetic field which are generated in the region inside the subject 1 are not parallel to each other. The sub-linear magnetic-field generating unit generates a linear magnetic field different from the second linear magnetic field in moving direction (magnetic-field direction), in the region inside the subject 1 including the position of the capsule endoscope 2; the magnetic-field controller drives one of the second linear magnetic-field generating unit 210 and the sub-linear magnetic-field generating unit, based on a geometric relation between the linear magnetic field generated in the region inside the subject 1 and the earth magnetism. In this configuration, the magnetic-field controller determines whether the moving direction of the linear magnetic field generated by the second linear magnetic-field generating unit 210 and the moving direction of the earth magnetism calculated by the earth-magnetism orientation calculator 275 are parallel to each other or not, and drives one of the second linear magnetic-field generating unit 210 and the sub-linear magnetic-field generating unit based on the result of determination. Specifically, the magnetic-field controller causes the second linear magnetic-field generating unit 210 to generate a linear magnetic field if the moving direction of the linear magnetic field generated by the second linear magnetic-field generating unit 210 is not parallel to the moving direction of the earth magnetism. On the other hand, the magnetic-field controller causes the sub-linear magnetic-field generating unit, in place of the second linear magnetic-field generating unit 210, to generate a linear magnetic field if the moving direction of the linear magnetic field generated by the second linear magnetic-field generating unit 210 is parallel to the moving direction of the earth magnetism. As a result, the position detecting apparatus 272 can reliably generate the linear magnetic field different from the second linear magnetic field in moving direction (i.e., the linear magnetic field having a magnetic field component magnetic-field in a direction not parallel to the moving direction of the earth magnetism), in the region inside the subject 1 including the position of the capsule endoscope 2.

An advantage of the body-insertable apparatus system according to the eleventh embodiment is explained next. The body-insertable apparatus system according to the eleventh embodiment has an advantage by using the earth magnetism in addition to the advantage of the ninth embodiment. That is, the mechanism for generating the first linear magnetic field can be omitted by adopting the configuration using the earth magnetism as the first linear magnetic field. Therefore, while the burden on the subject 1 at the time of introducing the capsule endoscope 2 can be reduced, the position of the target coordinate axis relative to the reference coordinate axis can be calculated. Since the earth magnetism sensor 273 can be formed by using the MI sensor or the like, the earth magnetism sensor 273 can have a small size, and the burden on the subject 1 does not increase by newly providing the earth magnetism sensor 273.

Further, there is a further advantage from a standpoint of reducing the power consumption, by adopting the configuration in which the earth magnetism is used as the first linear magnetic field. That is, when the first linear magnetic field is formed by using the coil or the like, the power consumption increases due to the electric current allowed to flow to the coil. However, such power consumption becomes unnecessary due to the earth magnetism, thereby enabling realization of a low power-consumption system.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detecting apparatus that detects a position of a body-insertable device, the body-insertable device being introduced into a subject to acquire intra-subject information while moving inside the subject, the position detecting apparatus comprising:

a linear magnetic-field generator adapted to generate a linear magnetic field in an area inside the subject, the area including the position of the body-insertable device;

a diffuse magnetic-field generator adapted to generate a diffuse magnetic field having a magnetic field direction that is position dependent in the area inside the subject;

a magnetic-field line orientation database adapted to record a correspondence between a magnetic field direction of the diffuse magnetic field and a position of the diffuse magnetic field in the subject in a reference coordinate axis, the reference coordinate axis being fixed to the subject;

an earth magnetism sensor adapted to be arranged on the surface of the subject and adapted to detect strength of magnetic field components of earth magnetism in the reference coordinate axis;

an earth magnetism orientation calculator adapted to calculate the magnetic field direction of earth magnetism in the reference coordinate axis based on the strength of the magnetic field components detected by the earth magnetism sensor;

an orientation calculator adapted to acquire linear magnetic-field information relating to the magnetic field direction of the linear magnetic field and the magnetic field direction of earth magnetism calculated by the earth magnetism orientation calculator, and calculate correspondence between the reference coordinate axis and a target coordinate axis, which is fixed to the body-insertable device, as orientation information of the body-insertable apparatus based on the acquired linear magnetic-field information and the magnetic field direction of earth magnetism; and a position calculator adapted to
acquire information on the strength of the linear magnetic-field, the orientation information, and diffuse magnetic-field information relating to the magnetic field direction of the diffuse magnetic field at the position of the body-insertable device in the target coordinate axis,
calculate the magnetic field direction of the diffuse magnetic field at the position of the body-insertable device in the reference coordinate axis based on the information on the strength of the linear magnetic-field, the orientation information, and the diffuse magnetic-field information, and
calculate the position of the body-insertable device based on the calculated magnetic field direction and the correspondence recorded in the magnetic-field line orientation database.

2. The position detecting apparatus according to claim 1, wherein the position calculator calculates a distance between the linear magnetic-field generator and the body-insertable device based on a strength attenuation factor of the linear magnetic field corresponding to the acquired information on the strength, and designates a position corresponding to the magnetic field direction of the diffuse magnetic field of positions inside the subject at the calculated distance, as the position of the body-insertable device.

3. The position detecting apparatus according to claim 1, further comprising:

a sub-linear magnetic-field generator adapted to generate a linear magnetic field having a magnetic field direction that is different from the magnetic field direction of the linear magnetic field generated by the linear magnetic field generator, in the region inside the subject including the position of the body-insertable device; and a magnetic-field controller that determines whether a magnetic field direction of the linear magnetic field generated by the linear magnetic-field generator and a magnetic field direction of the earth magnetism calculated by the earth magnetism orientation calculator are parallel to each other or not, causes the linear magnetic-field generator to generate the linear magnetic field if the magnetic field directions are not parallel to each other, and causes the sub-linear magnetic-field generator, in place of the linear magnetic-field generator, to generate the linear magnetic field if the magnetic field directions are parallel to each other.

4. A position detecting apparatus that detects a position of a body-insertable device, the body-insertable device being introduced into a subject to acquire intra-subject information while moving inside the subject, the position detecting apparatus comprising:

a plurality of linear magnetic-field generators adapted to generate a plurality of linear magnetic fields each having a different magnetic field direction, in an area inside the subject, the area including the position of the body-insertable device;

a diffuse magnetic-field generator adapted to generate a diffuse magnetic field having a magnetic field direction that is position dependent in the area inside the subject;

a magnetic-field line orientation database adapted to record a correspondence between a magnetic field direction of the diffuse magnetic field and the position of the diffuse magnetic field in the subject in a reference coordinate axis is recorded, the reference coordinate axis being fixed to the subject;

an earth magnetism sensor adapted to be arranged on the surface of the subject and adapted to detect strength of magnetic field components of earth magnetism in the reference coordinate axis;

an earth magnetism orientation calculator adapted to calculate the magnetic field direction of earth magnetism in the reference coordinate axis based on the strength of the magnetic field components detected by the earth magnetism sensor;

an orientation calculator adapted to acquire linear magnetic-field information relating to the magnetic field direction of one of the linear magnetic fields and the magnetic field direction of earth magnetism calculated by the earth magnetism orientation calculator, calculate correspondence between the reference coordinate axis and a target coordinate axis, which is fixed to the body-insertable device, as orientation information of the body-insertable apparatus based on the acquired linear magnetic-field information and the magnetic field direction of earth magnetism; and a position calculator adapted to
acquire the orientation information, information on the strength of one of the linear magnetic fields generated by the linear magnetic field generators and diffuse magnetic-field information relating to the magnetic field direction of the diffuse magnetic field at the position of the body-insertable device in the target coordinate axis,
calculate the magnetic field direction of the diffuse magnetic field at the position of the body-insertable device in the reference coordinate axis based on the information on the strength of one of the magnetic fields, the orientation information, and the diffuse magnetic-field information, and calculate the position of the body-insertable device based on the calculated magnetic field direction and the correspondence recorded in the magnetic-field line orientation database, wherein when the acquired magnetic field direction of the one of the magnetic fields is approximately parallel to the magnetic field direction of the earth magnetism, the orientation calculator acquires the magnetic field direction of another one of the linear magnetic fields generated by the linear magnetic field generators and calculates the correspondence between the reference coordinate axis and the target coordinate axis based on the magnetic field direction of another one of the linear magnetic fields.

5. The position detecting apparatus according to claim 4, wherein the position calculator calculates a distance between the one of the linear magnetic-field generators and the body-insertable device based on a strength attenuation factor of the linear magnetic field corresponding to the acquired information on the strength, and designates a position corresponding to the calculated magnetic field direction of the diffuse magnetic field from positions inside the subject at the calculated distance, as the position of the body-insertable device.

\* \* \* \* \*